(12) United States Patent
Sladek et al.

(10) Patent No.: US 6,500,672 B1
(45) Date of Patent: Dec. 31, 2002

(54) LIVER ENRICHED TRANSCRIPTION FACTOR

(75) Inventors: Frances M. Sladek, Riverside, CA (US); Weimin Zhong, New York, NY (US); James E. Darnell, Jr., Larchmont, NY (US)

(73) Assignee: The Rockefeller University, New York, NY (US)

( * ) Notice: Subject to any disclaimer, the term of this patent is extended or adjusted under 35 U.S.C. 154(b) by 0 days.

(21) Appl. No.: 09/447,034

(22) Filed: Nov. 22, 1999

Related U.S. Application Data

(62) Division of application No. 09/038,217, filed on Mar. 11, 1998, now Pat. No. 6,025,196, which is a division of application No. 08/661,330, filed on Jun. 14, 1996, now Pat. No. 5,849,485, which is a division of application No. 08/078,222, filed as application No. PCT/US91/09733 on Dec. 23, 1991, now Pat. No. 5,604,115, which is a division of application No. 07/631,720, filed on Dec. 21, 1990, now abandoned.

(51) Int. Cl.[7] .......................... C01N 33/00; C01N 33/566
(52) U.S. Cl. .......................... 436/501; 436/86; 530/350; 530/358; 530/361; 530/387-3; 530/388.21; 530/387.9
(58) Field of Search ................................. 530/350, 358, 530/361, 387-3, 388.21, 387.9; 536/23-2; 436/501, 86

(56) References Cited

U.S. PATENT DOCUMENTS 4,394,443 A    7/1983   Weissman et al.

OTHER PUBLICATIONS

LeStourgeon et al. Rapid isolation, hihg–resolution electrophoretic characterization and purification of nuclear proteins. Methods in Cell Biol. vol. 16:387–406, 1977.*

Khalfan et al. Aminomethyl coumarin acetic: a new fluorescent labelling agent for proteins. Histochemical J. vol. 18:497–499, 1986.*

Ahe, von der D., Janich, S., Scheidereit, C., Renkawitz, R., Schutz, G., and Beato, M. (1985). Glucocorticoid and progesterone receptors bind to the same sites in two hormonally regulated promoters. *Nature*, 313, 706–709.

Baumhueter, S., Mendel, D. B., Conley, P. B., Kuo, C. J., Turk, C., Graves, M. K., Edwards, C. A., Courtois, G., and Crabtree, G. R. (1990). HNF–1 shares three sequence motifs with the POU domain proteins and is identical to LF–B1 and APF. *Genes and Development* 4, 372–379.

Beato, M. (1989). Gene regulation by steroid hormones. *Cell* 56, 335–344.

Bell, J. Ellis, 1988, Protein Purification: Affinity Chromatograpy. *Proteins and Enzymes* Prentice–Hall Inc.. 45–63.

Birkenmeier, E.H., Gwynn, B., Howard, S., Jerry, J., Gordon, J.I., Landschulz, W.H., and McKnight, S.L. (1989). Tissue–specific expression, developmental regulation and mapping of the gene encoding CCAAT/enhancer binding protein. *Genes and Development*, 3, 1146–1156.

Brand, N., Petkovich,M., Krust, A., Chambon, P., de The, H., Marchio, A., Tiollais, P., and Dejean, A. (1988). Identification of a second human retinoic acid receptor. *Nature*, 332, 850–853.

Briggs, M.R., Kadonaga, J.T., Bell, S.P., and Tjian, R. (1986) Purification and biochemical characterization of the promoter–specific transcription factor, Sp1. *Science, 234*, 47–52.

Breslow, J. (1988). Apolipoprotein genetic variation and human disease. *Physiol. Reviews*, 68, 85–132.

Capon, D. J. et al. (1989). Designing CF4 immunoadhesins for AIDS therapy. *Nature*, 337, 525–531.

Carlsson, R., and Glad, C. (Jun., 1989). Monoclonal antibodies into the '90s. *Bio/Technology*, 7, 567–573.

Cate, R. et al. (1986). Isolation of the bovine and human genes for Mullerian inhibiting substance and expression of the human gene in animal cells. *Cell*, 45, 685–598.

Cech, T. R. (1988). Ribozymes and their medical implications. *J. Amer. Med. Assn.*, 260, 3030–3044.

Chomezynski, P. and Sacchi, N. (1987). Single–step method of RNA isolation by acid guanidinium thiocyanate–phenol–chloroform extraction. *Anal. Biochem.*, 162, 156–159.

Costa, R. H., Lai, E., and Darnell, J. E., Jr. (1986). Transcriptional control of the mouse prealbumin (transthyretin) gene: both promoter sequences and a distinct enhancer are cell specific. *Mol. and Cell. Biol.*, 6, 4697–4708.

(List continued on next page.)

Primary Examiner—Rebecca E. Prouty
Assistant Examiner—Manjunath N. Rao
(74) Attorney, Agent, or Firm—Klauber & Jackson

(57) ABSTRACT

HNF-4 (hepatocyte nuclear factor 4) is a protein enriched in liver extracts that binds to sites required for the transcription of the transthyretin (TTR) and apolipoprotein CIII (apoCIII) genes (Costa et al., 1989; Costa et al., 1990; Leff et al., 1989). We have purified HNF-4 protein (54 kD) and isolated a cDNA clone encoding the protein. HNF-4 is a member of the steroid hormone receptor superfamily with an unusual amino acid in the conserved "knuckle" of the first zinc finger (DGCKG). This and the fact that HNF-4 does not bind significantly to estrogen, thyroid hormone or glucocorticoid response elements indicate that HNF-4 may represent a new subfamily. HNF-4 binds to its recognition site as a dimer and activates transcription in a sequence-specific fashion in nonhepatic (HeLa) cells. HNF-4 mRNA is present in kidney and intestine as well as liver but is absent in other tissues. DNA binding data suggest that HNF-4 could be identical to liver factor A1 (LF-A1), a factor previously shown to regulate the transcription of the α-1 antitrypsin, apolipoprotein A1 and pyruvate kinase genes.

5 Claims, 19 Drawing Sheets

OTHER PUBLICATIONS

Costa, R. H., Grayson, D. R., Xanthopoulos, K.G., and Darnell, J. E., Jr. (1988). A liver–specific DNA–binding protein recognizes multiple nucleotide sites in regulatory regions of transthyretin, a1–antitrypsin, albumin, and simian virus 40 genes. *Proc. Natl. Acad. Sci.*, 85, 3840–3844.

Costa, R. H., Grayson, D. R. and Darnell, J. E. Jr. (1989). Multiple hepatocyte–enriched nuclear factors function in the regulation of transthyretin and a1–antitrypsin genes. *Mol. and Cell. Biol.*, 9, 1415–1425.

Costa, R. H., Van Dyke, T. A., Yan, C., Kuo, F., and Darnell, J. E., Jr. (1990). Similarities in transthyretin gene expression and differences in transcription factors: liver and yolk sac compared to choroid plexus. *Proc. Natl. Acad. Sci. USA*, 87, 6589–6593.

Courtois, G., Morgau, J. G., Campbell, L. A., Fourel, G. and Crabtree, G. R. (1987). Interaction of a liver–specific nuclear factor with the fibrinogen and al–antitrypsin promoters. *Science*, 238, 688–692.

Danielsen, M. Hinck, L., and Ringold, G. M. (1989). Two amino acids within the knuckle of the first zinc finger specify DNA response element activation by the glucocorticoid receptor. *Cell*, 57, 1131–1138.

Davis, M. M. (1986). Subtractive cDNA hybridization and the T–cell receptor gene. *Handbook of Experimental Immunology in Four Volumes*, 4th ed. Blackwell Scientific Publications, Oxford, England, 76.1–76.13.

Davis, M. M. et al. (1984). Cell type–specific cDNA probes and the murine I region: The localization and orientation of ad. *Proc. Natl. Acad. Sci. USA*, 81, 2194–2198.

Derman, E., Krauter, K., Walling, L., Weinberger, C., Ray, M. and Darnell, J. E. Jr. (1981). Transcriptional control in the production of liver–specific mRNAs. *Cell*, 23, 731–739.

de The, H., Marchio, A., Tiollais, P., and Dejean, A. (1987). A novel steroid thyroid hormone receptor–related gene inappropriately expressed in human hepatocellular carcinoma. *Nature*, 330, 667–670.

Duguid, J. R. et al. (1988). Isolation of cDNAs of scrapie–modulated RNMAs by subtractive hybridization of a cDNA library. *Proc. Natl. Acad. Sci. USA*, 85, 5738–5742.

Evans, R.M. (1988). The steroid and thyroid hormone receptor superfamily. *Science*, 240, 889–895.

Fawell, S.E., Lees, J.A. White,R. and Parker, M.G. (1990). Characterization and colocalization of steroid binding and dimerization activities in the mouse estrogen receptor. *Cell*, 60, 953–962.

Feinberg, A.P., and Vogelstein, B. (1983). A technique for radiolabeling DNA restriction endonuclease fragments to high specific activity. *Anal. Biochem.*, 132, 6–13.

Fisher, R. A. et al. (1988). HIV infection is blocked in vitro by recombinant soluble CD4. *Nature*, 331, 76–78.

Forman, B. M., Yan, C. R., Au, M., Casanova, J., Ghysdael, J., and Samuels, H. H. (1989). A domain containing leucine–zipper–like motifs mediate novel in vivo interactions between the thyroid hormone and retinoic acid receptors. *Mol. End.*, 3, 1610–1626.

Forman, B. M. and Samuels, H. H. (1990). Interactions among a subfamily of nuclear hormone receptors: The regulatory zipper model. *Mol. End.* 4, 1293–1301.

Frain, M., Swart, G., Monaci, P., Nicosia, A., Stampfli, S., Frank, R., and Cortese, R. ( 1989). The liver–specific transcription factor LF–Bl contains a highly diverged homeobox DNA binding domain. *Cell*, 59, 145–157.

Fried, M. and Crothers, D. M. (1981). Equilibria and kinetics of lac repressor–operator interactions by polyacrylamide gel electrophoresis. *Nucleic Acids Res.*, 9, 6505–6525.

Giguere, V., Yang, N., Segui, P., and Evans, R. M. (1988). Identification of a new class of steroid hormone receptors. *Nature*, 331, 91–94.

Glass, C.K. Holloway, J.M. Devary, O.V., and Rosefeld, M. (1988) The thyroid hormone receptor binds with opposite transcription effects to a common sequence motif in thyroid hormone and estrogen response elements. *Cell*, 54:313–323.

Glass, C. K., Lipkin, S. M., Devary, O. V., and Rosenfeld, M. G. (1989). Positive and negative regulation of gene transcription by a retinoic acid–thyroid hormone receptor heterodimer. *Cell*, 59, 697–708.

Gorman, C. M., Moffat, L. F. and Howard, B. H. (1982). Recombinant genomes which express chloramphenicol acetyltransferase in mammalian cells. *Mol. Cell. Biol.*, 2, 1044–1051.

Gorman, C. M., Howard, B. H. and Reeves, R. (1983). Expression of recombinant plasmids in mammalian cells is enhanced by sodium butyrate. *Nucleic Acids Res.*, 11, 7631–7648.

Gorski, K., Carneiro, M. and Schibler, U. ( 1986). Tissue–specific in vitro transcription from the mouse albumin promoter. *Cell*, 47, 767–776.

Green, N., Alexander, H., Olson, A., Alexander, S., Shinnick, T.M., Sutcliffe, J.G., and Lerner, R.A. (1982). Immunogenic structure of the influenza virus hemagglutinin. *Cell*, 28, 477–487.

Green, S., Walter, P., Kumar, V., Krust, A., Bornert, J. M., Argos, P., and Chambon, P. (1986). Human oestrogen receptor cDNA: Sequence, expression and homology to c/epb. *Nature*, 320, 134–139.

Green, S. and Chambon, P. (1988). Nuclear receptors enhance our understanding of transcription regulation. *Trends Genet.*, 4, 309–314.

Gubler, U., and Hoffman, B. J. (1983). A simple and very efficient method for generating cDNA libraries. *Gene*, 25, 263–269.

Hamada, K., Gleason, S. L., Levi, B. Z., Hirschfeld, S., Appella, E., and Ozato, K. (1989). H–2RIIBP, a member of the nuclear hormone receptor superfamily that binds to both the regulatory element of major histocompatibility class I genes and the estrogen response element. *Proc. Natl. Acad. Sci. USA*, 86, 8289–8293.

Hambor, J. E. et al. (1988). Functional consequences of antisense RNA–mediate inhibition of CD8 surface expression in a human T cell clone. *J. Exp. Med.*, 168, 1237–1245.

Hardon, E. M., Frain, M., Paonessa, G. and Cortese, R. (1988). Two distinct factors interact with the promoter regions of several liver–specific genes. *The EMBO J.*, 7, 1711–1719.

Haseloff, J., and Gerlach, W. L. (1988). Simple RNA enzymes with new and highly specific endoribonuclease activities. *Nature*, 334, 585–591.

Hedrick, S. M. et al. (1984). Isolation of cDNA clones encoding T cell–specific membrane–associated proteins. *Nature*, 308, 149–153.

Ito, Y., Azrolan, N., O'Connell, A., Walsh, A., and Breslow, J.L. (1990) Hypertriglyceridemia as a result of human apoCIII gene expression in transgenic mice. *Science*, 249, 790–793.

Johnson, P. F., Landschulz, W. H., Graves, B. J., and McKnight, S. L. (1987). Identification of a rat liver nuclear protein that binds to the enhancer core element of three animal viruses. *Genes and Development*, 1, 133–146.

Johnson, P. F. (1990). Transcriptional activators in hepatocytes. In *Cell Growth and Differentiation*, 1, 47–52.

Kadonaga, J. T., and Tjian, R. (1986). Affinity purification of sequence–specific DNA binding proteins. *Proc. Natl. Acad. Sci. USA*, 83, 5889–5893.

Kennedy, R. C. et al. (Jul., 1986). Anti–idiotypes and immunity. *Sci. Am.*, 255, 48–56.

Klein–Hitpab, L., Schorpp, M., Wagner, U., and Ryffel, G.U., (1986). An estrogen–responsive element derived from the 5' flanking region of the Xenopus vitellogenin A2 gene functions in transfected human cells. *Cell*, 46, 1053–1061.

Kozak, M. (1987). An analysis of 5'–noncoding sequences from 699 vertebrate messenger RNA's. *Nucleic Acids Res.*, 15, 8125–8143.

Krebs, E., Eisenman, R., Kuenzel, E., Litchfield, D., Lozeman, F., Lischer, B. and Sommercorn, J. (1988). Casein kinase II as a potentially important enzyme concerned with signal transduction. In *Molecular Biology of Signal Transduction*. (Cold Spring Harbor, New York: Cold Spring Harbor Laboratory), p. 77–84.

Kumar, V., and Chambon, P. (1988). The estrogen receptor binds tightly to its responsive element as a ligand–induced homodimer. *Cell*, 55, 145–156.

Kuo, C. F., Xanthopoulos, K. G., and Darnell, J. E. Jr. (1990). Fetal and adult localization of C/EBP: evidence for combinatorial action of transcription factors in cell–specific gene expression. *Development*, 109, 473–481.

Kuwabara, M.D. and Sigman, D.S. (1987). Footprinting DNA–protein complexes in situ following gel retardation asays using 1, 10–phenathroline–copper ion: *Escherichia coli* RNA polymerase–lac promoter complexes. *Biochem.*, 26, 7234–7238.

Laemmli, U.K. (1970). cleavage of structural proteins during the assembly of the head of bacteriaphage T4. *Nature*, 227, 680–685.

Lai, E., Prezioso, V. R., Smith, E., Litvin, O., Costa, R. H., and Darnell, J. E., Jr. (1990). HNF–3A, a hepatocyte–enriched transcription factor of novel structure is regulated transcriptionally. *Genes and Development*, 4, 1427–1436.

Landschulz, W. H., Johnson, P. F., Adashi, E. Y., Graves, B. J., and McKnight, S. L. (1988). Isolation of a recombinant copy of the gene encoding C/EBP. *Genes and Development*, 2, 786–800.

Lathe, E. ( 1985). Synthetic oligonucleotide probes deduced from amino acid sequence data: Theoretical and practical considerations. *J. Mol. Biol.*, 183, 1–12.

Leff, T., Reue, K., Melian, A., Culver, H., and Breslow, J. L. (1989). A regulatory element in the ApoCIII promoter that directs hepatic specific transcription binds to proteins in expressing and nonexpressing cell types. *J. Biol. Chem.*, 264, 16132–16137.

Lew, D.J., Decker, T., Strehlow, I. and Darnell, J.E. (1990). Overlapping elements in the GBP gene promoter mediate transcriptional induction by alpha and gamma–interferon. *Mol. Cell Biol.*, in press.

Li, Y., Shen, R.–F., Tsai, S. Y., and Woo, S. L. C. (1988). Multiple hepatic trans–acting factors are required for in vitro transcription of the human alpha–1–antitrypsin gene. *Mol. and Cell. Biol.*, 8, 4362–4369.

MacGregor, G. R., and Caskey, C. T. (1989). Construction of plasmids that express *E. coli* b–galactosidase in mammalian cells. *Nucleic Acids Res.*, 17, 2365.

Mader, S., Kumar, V., de Verneuil, H., and Chambon, P. (1989). Three amino acids of the oestrogen receptor are essential to its ability to distinguish an oestrogen from a glucocorticoid–responsive element. *Nature*, 338, 271–274.

Mangelsdorf, D.J., Ong, E.S., Dyck, J.A. and Evans, R.M. (1990). Nuclear receptor that identifies a novel retinoic acid response pathway. *Nature*, 345, 224–229.

Marcus–Sekura, C. J. (1988). Techniques for using antisense oligonucleotides to study gene expression. *Anal. Biochem.*, 172, 289–295.

Matsudaira, P. (1987). Sequence from picomole quantities of proteins electroblotted onto polyvinylidene difluorid membranes. *J. Biol. Chem.*, 262, 10035–10038.

McKnight, G.S., and Palmiter, R.D. (1979). Transcriptional regulation of the ovalbumin and conalbumin genes by steroid hormones in chick oviduct. *J. Biol. Chem.*, 254, 9050–9058.

Mermod, N., O'Neill, E. A., Kelly, T. J. and Tjian, R. (1989). The proline–rich transcriptional activator of CTF/NF–1 is distinct from the replication and DNA binding domain. *Cell*, 58, 741–753.

Milstein, C., *Handbook of Experimental Immunology* Overview: monoclonal antibodies. Chapter 107. 1–12.

Miyajiima, N., Kadowaki, Y., Fukushige, Shiminizu, S., Semba, K., Yamanashi, Y. H., Matsubara, K., Toyoshima, K., and Yamanoto, T. (1988). Identification of two novel members of erbA superfamily by molecular cloning: The gene products of the two are highly related to each other. *Nucleic Acids Res.*, 16, 11057–11074.

Monaci, P., Nicosia, A., and Cortese, R. (1988). Two different liver–specific factors stimulate in vitro transcription from the human a1–antitrypsin promoter. *The EMBO J.*, 7, 2075–2087.

Mueller, C. R., Maire, P., and Schibler, U. (1990). DBP, a liver–enriched transcriptional activator, is expressed late in ontogeny and its tissue specificity is determined posttranscriptionally. *Cell*, 61, 279–291.

O'Malley, B.W., (1988). Molecular interactions of seroid hormone reeptor with its enhancer element: Evidene for receptor dimer formation. *Cell*, 55, 361–369.

Pearson, W. R., and Lipman, D. J. (1988). Improved tools for biological sequence comparison. *Proc. Natl. Acad. Sci. USA*, 85, 2444–2448.

Puissant, C., and Houdebine, L. M. (1990). An improvement of the single–step method of RNA isolation by acid guanidinium thiocyanate–phenol–chloroform extraction. *BioTechniques*, 8, 148–149.

Reue, K., Leff, T., and Breslow, J. L. (1988). Human apolipoprotein CIII gene expression is regulated by positive and negative Cis–acting elements and tissue–specific protein factors. *The J. of Biol. Chem.*, 263, 6857–6864.

Rosen, C.A., Sodroski, J. G. and Haseltine, W. A. (1985). The location of cis–acting regulatory sequences in the human T cell lymphotropic virus type III (HTLV–III/LAV) long terminal repeat. *Cell*, 41, 813–823.

Ruppert, S., Boshart, M., Bosch, F. X., Schmid, W., Fournier, R.E.K., and Shutz, G. (1990). Two genetically defined trans–acting loci coordinately regulate overlapping sets of liver–specific genes. *Cell*, 61, 895–904.

Ryseck, R. P., Macdonald–Bravo, H., Mattei, M. G., Ruppert, S., and Bravo, R. (1989). Structure, mapping and expression of a growth factor inducible gene encoding a putative nuclear hormonal receptor. *The EMBO J.*, 8, 3327–3335.

Saiki, R. K., Gelfand, D. H., Stoffel, S., Scharf, S. J., Higuchi, R., Horn, G. T., Mullis, K. B., and Erlich, H. A. (1988). Primer–directed enzymatic amplification of DNA with a thermostable DNA polymerase. *Science*, 239, 487–491.

Sanger, F., Nicklen, S., and Coulson, A. R. (1977). DNA sequencing with chain terminating inhibitors. *Proc. Natl. Acad. Sci. USA*, 74, 5463–5467.

Sambrook, J., Fritsch, E. F., and Maniatis, T. (1989). *Molecular cloning: A laboratory manual.* (Cold Spring Harbor, N.Y.: Cold Spring Harbor Laboratory).

Sargent, T. D. (1987). Isolation of differentially expressed genes. *Methods in Enzymol.*, 152, 423–447.

Schule, R., Umesono, K., Mangelsdorf, D. J., Bolado, J., Pike, J. W., and Evans, R. M. (1990). Jun–fos and receptors for vitamins A and D recognize a common response element in the human osteocalcin gene. *Cell*, 61, 497–504.

Seed, B. (1987). An LFA–3 cDNA encodes a phospholipid–linked membrane protein homologous to its receptor CD2. *Nature*, 329, 840–842.

Seed, B., and Aruffo, A. (1987). Molecular cloning of the CD2 entigen, the T–cell erythrocyte receptor, by a rapid immunoselection procedure. *Proc. Natl. Acad. Sci. USA*, 84, 3365–3369.

Sladek, Frances M. et al., (1990). Liver–enriched transcription factor HNF–4 is a novel member of the steroid hormone receptor superfamily. *Genes & Development, 4 No. 12b*, 2235–2438.

Stahle, U., Klock, G., and Schutz, G. (1987). A DNA sequence of 15 base pairs is sufficient to mediate both glucocorticoid and progesterone induction of gene expression. *Proc. Natl. Acad. Sci., 84*, 7871–7875.

Tsai, S. Y., Carlstedt–Duke, J., Weigel, N. L., Dahlman, K., Gustafsson, J. A., Tsai, M. J., and O'Malley, B. W. (1988). Molecular interactions of steroid hormone receptor with its enhancer element: Evidence for receptor dimer formation. *Cell*, 55, 361–369.

Umesono, K., Giguere, V., Glass, C. K., Rosenfeld, M. G., and Evans, R. M. (1988). Retinoic acid and thyroid hormone induce gene expression through a common responsive element. *Nature*, 336, 262–265.

Umesono, K. and Evans, R. M. (1989). Determinants of target gene specificity for steroid/thyroid hormone receptors. *Cell*, 57, 1139–1146.

Vaulont, S., Puzenat, N., Kahn, A., and Raymondjean, M. (1989). Analysis by cell–free transcription of the liver–specific pyruvate kinase gene promoter. *Mol. and Cell. Biol.*, 9, 4409–4415.

Wang, L. H., Tsai, S. Y., Cook, R. G., Beattie, W. G., Tsai, M. J. and O'Malley, B. W. (1989). COUP transaction factor is a member of the steroid receptor superfamily. *Nature*, 340, 163–166.

Weinberger, C., Thompson, C. C., Ong, E. S., Lebo, R., Gruo, D.J., and Evans, R.M. (1986). The c/epb gene encodes a thyroid hormone receptor. *Nature*, 243, 641–646.

Wingender, E. (1990). Transcription regulating proteins and their recognition sequences. *Critical Reviews in Eukaryotic Gene Expression*, 1, 11–48.

Wysocki, L. J., and Sato, V. L. (1978). Panning for lymphocytes: A method for cell selection. *Proc. Natl. Acad. Sci. USA*, 75, 2844–2848.

Xanthopoulos, K. G., Mirkovitch, J., Decker, T., Kuo, C. F., and Darnell, J. E., Jr. (1989). Cell–specific transcriptional control of the mouse DNA–binding protein mC/EBP. *Proc. Natl. Acad. Sci. USA* 86, 4117–4121.

Xanthopoulos, K. G. et al. (1991). The different tissue transcription patterns of genes for HNF–1, C/EBP, HNF–3 and HNF–4, protein factors that govern liver–specific transcription. *Proc. Natl. Acad. Sci. USA*, 88, 3807–3811.

Yamasaki, K. et al. (1988). Cloning and expression of the human interleukin–6 (BSF–2/IFNB2) receptor. *Science*, 241, 825–828.

Young, R. A. and Davis, R. W. (1983). Efficient isolation of genes by using antibody probes. *Proc. Natl. Acad. Sci. USA*, 80, 1194–1198.

\* cited by examiner

```
CGACAGGGGGCTGAGGGGTGGGTAGAGGAGAATGCGACTCTCTAAAACCCTCGCC              55

GAC ATG GAC ATG GCT GAC TAC AGT GCT GCC TTG GAC CCA GCC              97
    Met Asp Met Ala Asp Tyr Ser Ala Ala Leu Asp Pro Ala
    1           5                   10

TAC ACC ACC CTG GAG TTT GAA AAT GTG CAG GTG TTG ACC ATG              139
Tyr Thr Thr Leu Glu Phe Glu Asn Val Gln Val Leu Thr Met
    15              20                  25

GGC AAT GAC ACA TCC CCA TCT GAA GGT GCC AAC CTC AAC TCA              181
Gly Asn Asp Thr Ser Pro Ser Glu Gly Ala Asn Leu Asn Ser
        30              35                  40

TCC AAC AGC CTG GGT GTC AGT GCC CTG TGT GCC ATC TGT GGC              223
Ser Asn Ser Leu Gly Val Ser Ala Leu Cys Ala Ile Cys Gly
            45              50                  55

GAT CGG GCC ACT GGC AAA CAC TAC GGA GCC TCA AGC TGT GAC              265
Asp Arg Ala Thr Gly Lys His Tyr Gly Ala Ser Ser Cys Asp
                60              65

GGC TGC AAG GGA TTC TTC AGG AGG AGC GTG AGG AAG AAC CAC              307
Gly Cys Lys Gly Phe Phe Arg Arg Ser Val Arg Lys Asn His
70              75                  80

ATG TAC TCC TGC AGG TTT AGC AGG CAG TGC GTG GTA GAC AAA              349
Met Tyr Ser Cys Arg Phe Ser Arg Gln Cys Val Val Asp Lys
    85              90                  95

GAT AAG AGG AAC CAG TGT CGT TAC TGC AGG CTC AAG AAG TGC              391
Asp Lys Arg Asn Gln Cys Arg Tyr Cys Arg Leu Lys Lys Cys
        100             105                 110

TTC CGG GCT GGC ATG AAG AAA GAA GCC GTC CAA AAT GAG CGG              433
Phe Arg Ala Gly Met Lys Lys Glu Ala Val Gln Asn Glu Arg
            115             120                 125

GAT CGG ATC AGC ACG CGG AGG TCA AGC TAC GAG GAC ATC AGC              475
Asp Arg Ile Ser Thr Arg Arg Ser Ser Tyr Glu Asp Ile Ser
                130             135

CTA CCC TCC ATT AAT GCG CTC CTG CAG GCA GAG GTC CTG TCT              517
Leu Pro Ser Ile Asn Ala Leu Leu Gln Ala Glu Val Leu Ser
140             145                 150

CAG CAG ATC ACC TCC CCC ATC TCT GGG ATC AAT GGC GAC ATT              559
Gln Gln Ile Thr Ser Pro Ile Ser Gly Ile Asn Gly Asp Ile
    155             160                 165

CGG GCC AAG AGG ATT GCC AGC ATC ACG GAT GTG TGT GAG TCT              601
Arg Ala Lys Arg Ile Ala Ser Ile Thr Asp Val Cys Glu Ser
        170             175                 180

ATG AAG GAG CAG CTG CTG GTT CTG GTC GAA TGG GCC AAG TAC              643
Met Lys Glu Gln Leu Leu Val Leu Val Glu Trp Ala Lys Tyr
            185             190                 195
```

FIG.3B 1

```
ATC CCG GCC TTC TGT GAA CTT CTT CTG GAT GAC CAG GTG GCG   685
Ile Pro Ala Phe Cys Glu Leu Leu Leu Asp Asp Gln Val Ala
                200                 205

CTG CTC AGA GCC CAC GCT GGT GAG CAC CTG CTT CTG GGA GCC   727
Leu Leu Arg Ala His Ala Gly Glu His Leu Leu Leu Gly Ala
210                 215                 220

ACC AAG AGG TCC ATG GTG TTC AAG GAT GTG CTG CTC CTA GGC   769
Thr Lys Arg Ser Met Val Phe Lys Asp Val Leu Leu Leu Gly
    225                 230                 235

AAT GAC TAC ATC GTC CCT CGG CAC TGT CCA GAG CTA GCA GAG   811
Asn Asp Tyr Ile Val Pro Arg His Cys Pro Glu Leu Ala Glu
            240                 245                 250

ATG AGC CGT GTG TCC ATT CGC ATC CTC GAT GAG CTG GTC TTG   853
Met Ser Arg Val Ser Ile Arg Ile Leu Asp Glu Leu Val Leu
                255                 260                 265

CCC TTC CAA GAG CTG CAG ATC GAT GAT AAT GAA TAC GCC TGC   895
Pro Phe Gln Glu Leu Gln Ile Asp Asp Asn Glu Tyr Ala Cys
                    270                 275

CTC AAA GCC ATC ATC TTC TTT GAC CCA GAT GCC AAG GGG CTG   937
Leu Lys Ala Ile Ile Phe Phe Asp Pro Asp Ala Lys Gly Leu
280                 285                 290

AGT GAC CCA GGC AAG ATC AAG CGG CTG CGG TCA CAG GTG CAG   979
Ser Asp Pro Gly Lys Ile Lys Arg Leu Arg Ser Gln Val Gln
    295                 300                 305

GTG AGC CTG GAG GAT TAC ATC AAC GAC CGG CAG TAT GAC TCT  1021
Val Ser Leu Glu Asp Tyr Ile Asn Asp Arg Gln Tyr Asp Ser
        310                 315                 320

CGG GGT CGT TTT GGA GAG CTG CTG CTG CTC CTG CCC ACT CTG  1063
Arg Gly Arg Phe Gly Glu Leu Leu Leu Leu Leu Pro Thr Leu
                325                 330                 335

CAG AGC ATT ACC TGG CAG ATG ATC GAG CAG ATC CAG TTC ATC  1105
Gln Ser Ile Thr Trp Gln Met Ile Glu Gln Ile Gln Phe Ile
                    340                 345

AAG CTC TTT GGC ATG GCC AAG ATT GAC AAC CTG CTG CAG GAG  1147
Lys Leu Phe Gly Met Ala Lys Ile Asp Asn Leu Leu Gln Glu
350                 355                 360

ATG CTG CTT GGA GGG TCT GCC AGT GAC GCG CCC CAC GCC CAC  1189
Met Leu Leu Gly Gly Ser Ala Ser Asp Ala Pro His Ala His
    365                 370                 375
```

FIG.3B 2

```
CAC CCC CTG CAC CCT CAC CTG ATG CAA GAA CAC ATG GGC ACC 1231
His Pro Leu His Pro His Leu Met Gln Glu His Met Gly Thr
        380             385             390

AAT GTC ATA GTT GCC AAC ACG ATG CCC TCT CAC CTC ACG AAT 1273
Asn Val Ile Val Ala Asn Thr Met Pro Ser His Leu Thr Asn
        395             400             405

GGA CAG ATG TCC ACC CCT GAG ACT CCA CAG CCA TCA CCA CCA 1315
Gly Gln Met Ser Thr Pro Glu Thr Pro Gln Pro Ser Pro Pro
                410             415

AGT GGC TCT GGA TCT GAA TCC TAC AAG CTC CTG CCA GGA GCC 1357
Ser Gly Ser Gly Ser Glu Ser Tyr Lys Leu Leu Pro Gly Ala
420             425             430

ATC ACC ACC ATC GTC AAG CCT CCC TCT GCC ATC CCC CAG CCA 1399
Ile Thr Thr Ile Val Lys Pro Pro Ser Ala Ile Pro Gln Pro
        435             440             445

ACG ATC ACC AAG CAG GAA GCC ATC TAG  CAAGCCGCCGGGGGGTGG 1444
Thr Ile Thr Lys Gln Glu Ala Ile AM
        450             455

GGGTGAGGCTTCTGCTGGCTCACACCCTCAGAGAGCGCCTGGGTGTAACTTAGTC 1499

ACGGCAAAGAGGATGTGACAAGAGGGACCAGTCCCAGAGCAGCCACTGAAAGGGC 1554

TTGTAGGCCCAAAAACATGCGCTGAGGATCGCATGCATTGCCACCCCTGACCCCA 1609

CATCCGGAGGGCAGGGCTTTGCCTTGAGGAGACCCCGGCGGGGGGATGTCTTCCG 1664

CTGCCTGGACTCTTCTCAAGTTGAAGCTGCCGTCTTCATCTTCCCCTCATATCTT 1719

CCCTCAACTTCTTCACCCCTAAAGGACAACCATCTGCAG                 1758

Translated Mol. Weight = 50579.43
```

FIG.3B 3

SEQUENCE LISTING (1) GENERAL INFORMATION:

(iii) NUMBER OF SEQUENCES: 18

(2) INFORMATION FOR SEQ ID NO: 1:

(i) SEQUENCE CHARACTERISTICS:
      (A) LENGTH: 1758 base pairs
      (B) TYPE: nucleic acid
      (C) STRANDEDNESS: single
      (D) TOPOLOGY: linear (ii) MOLECULE TYPE: genomic DNA (iii) HYPOTHETICAL: yes (iv) ANTI-SENSE: no (v) FRAGMENT TYPE: polymerase chain reaction product (vi) ORIGINAL SOURCE:
      (A) ORGANISM: Rat liver nuclei (vii) IMMEDIATE SOURCE:
        (B) CLONE: pf7

(ix) FEATURE:
        (A) NAME/KEY:  partial coding sequence for mature
            factor
        (B) LOCATION:
        (C) IDENTIFICATION METHOD:  similarity to other
            members of the gene family
        (D) OTHER INFORMATION: Translated Mol. Weight =
            50579.43

(xi) SEQUENCE DESCRIPTION: SEQ ID NO: 1:

```
CGACAGGGGG CTGAGGGGTG GGTAGAGGAG AATGCGACTC TCTAAAACCC TCGCCGAC         58

ATG GAC ATG GCT GAC TAC AGT GCT GCC TTG GAC CCA GCC TAC ACC            103
Met Asp Met Ala Asp Tyr Ser Ala Ala Leu Asp Pro Ala Tyr Thr
 1               5                  10                  15

ACC CTG GAG TTT GAA AAT GTG CAG GTG TTG ACC ATG GGC AAT GAC            148
Thr Leu Glu Phe Glu Asn Val Gln Val Leu Thr Met Gly Asn Asp
                 20                  25                  30

ACA TCC CCA TCT GAA GGT GCC AAC CTC AAC TCA TCC AAC AGC CTG            193
Thr Ser Pro Ser Glu Gly Ala Asn Leu Asn Ser Ser Asn Ser Leu
                 35                  40                  45

GGT GTC AGT GCC CTG TGT GCC ATC TGT GGC GAT CGG GCC ACT GGC            238
Gly Val Ser Ala Leu Cys Ala Ile Cys Gly Asp Arg Ala Thr Gly
                 50                  55                  60

AAA CAC TAC GGA GCC TCA AGC TGT GAC GGC TGC AAG GGA TTC TTC            283
Lys His Tyr Gly Ala Ser Ser Cys Asp Gly Cys Lys Gly Phe Phe
                 65                  70                  75

AGG AGG AGC GTG AGG AAG AAC CAC ATG TAC TCC TGC AGG TTT AGC            328
Arg Arg Ser Val Arg Lys Asn His Met Tyr Ser Cys Arg Phe Ser
                 80                  85                  90

AGG CAG TGC GTG GTA GAC AAA GAT AAG AGG AAC CAG TGT CGT TAC            373
Arg Gln Cys Val Val Asp Lys Asp Lys Arg Asn Gln Cys Arg Tyr
                 95                 100                 105

TGC AGG CTC AAG AAG TGC TTC CGG GCT GGC ATG AAG AAA GAA GCC            418
Cys Arg Leu Lys Lys Cys Phe Arg Ala Gly Met Lys Lys Glu Ala
                110                 115                 120

GTC CAA AAT GAG CGG GAT CGG ATC AGC ACG CGG AGG TCA AGC TAC            463
Val Gln Asn Glu Arg Asp Arg Ile Ser Thr Arg Arg Ser Ser Tyr
                125                 130                 135

GAG GAC ATC AGC CTA CCC TCC ATT AAT GCG CTC CTG CAG GCA GAG            508
Glu Asp Ile Ser Leu Pro Ser Ile Asn Ala Leu Leu Gln Ala Glu
                140                 145                 150

GTC CTG TCT CAG CAG ATC ACC TCC CCC ATC TCT GGG ATC AAT GGC            553
Val Leu Ser Gln Gln Ile Thr Ser Pro Ile Ser Gly Ile Asn Gly
                155                 160                 165

GAC ATT CGG GCC AAG AGG ATT GCC AGC ATC ACG GAT GTG TGT GAG            598
Asp Ile Arg Ala Lys Arg Ile Ala Ser Ile Thr Asp Val Cys Glu
                170                 175                 180

TCT ATG AAG GAG CAG CTG CTG GTT CTG GTC GAA TGG GCC AAG TAC            643
Ser Met Lys Glu Gln Leu Leu Val Leu Val Glu Trp Ala Lys Tyr
                185                 190                 195

ATC CCG GCC TTC TGT GAA CTT CTT CTG GAT GAC CAG GTG GCG CTG            688
Ile Pro Ala Phe Cys Glu Leu Leu Leu Asp Asp Gln Val Ala Leu
                200                 205                 210

CTC AGA GCC CAC GCT GGT GAG CAC CTG CTT CTG GGA GCC ACC AAG            733
Leu Arg Ala His Ala Gly Glu His Leu Leu Leu Gly Ala Thr Lys
                215                 220                 225

AGG TCC ATG GTG TTC AAG GAT GTG CTG CTC CTA GGC AAT GAC TAC            778
Arg Ser Met Val Phe Lys Asp Val Leu Leu Leu Gly Asn Asp Tyr
```

```
                        230               235                240
ATC GTC CCT CGG CAC TGT CCA GAG CTA GCA GAG ATG AGC CGT GTG          823
Ile Val Pro Arg His Cys Pro Glu Leu Ala Glu Met Ser Arg Val
                245               250                255

TCC ATT CGC ATC CTC GAT GAG CTG GTC TTG CCC TTC CAA GAG CTG          868
Ser Ile Arg Ile Leu Asp Glu Leu Val Leu Pro Phe Gln Glu Leu
                260               265                270

CAG ATC GAT GAT AAT GAA TAC GCC TGC CTC AAA GCC ATC ATC TTC          913
Gln Ile Asp Asp Asn Glu Tyr Ala Cys Leu Lys Ala Ile Ile Phe
                275               280                285

TTT GAC CCA GAT GCC AAG GGG CTG AGT GAC CCA GGC AAG ATC AAG          958
Phe Asp Pro Asp Ala Lys Gly Leu Ser Asp Pro Gly Lys Ile Lys
                290               295                300

CGG CTG CGG TCA CAG GTG CAG GTG AGC CTG GAG GAT TAC ATC AAC         1003
Arg Leu Arg Ser Gln Val Gln Val Ser Leu Glu Asp Tyr Ile Asn
                305               310                315

GAC CGG CAG TAT GAC TCT CGG GGT CGT TTT GGA GAG CTG CTG CTG         1048
Asp Arg Gln Tyr Asp Ser Arg Gly Arg Phe Gly Glu Leu Leu Leu
                320               325                330

CTC CTG CCC ACT CTG CAG AGC ATT ACC TGG CAG ATG ATC GAG CAG         1093
Leu Leu Pro Thr Leu Gln Ser Ile Thr Trp Gln Met Ile Glu Gln
                335               340                345

ATC CAG TTC ATC AAG CTC TTT GGC ATG GCC AAG ATT GAC AAC CTG         1138
Ile Gln Phe Ile Lys Leu Phe Gly Met Ala Lys Ile Asp Asn Leu
                350               355                360

CTG CAG GAG ATG CTG CTT GGA GGG TCT GCC AGT GAC GCG CCC CAC         1183
Leu Gln Glu Met Leu Leu Gly Gly Ser Ala Ser Asp Ala Pro His
                365               370                375

GCC CAC CAC CCC CTG CAC CCT CAC CTG ATG CAA GAA CAC ATG GGC         1228
Ala His His Pro Leu His Pro His Leu Met Gln Glu His Met Gly
                380               385                390

ACC AAT GTC ATA GTT GCC AAC ACG ATG CCC TCT CAC CTC ACG AAT         1273
Thr Asn Val Ile Val Ala Asn Thr Met Pro Ser His Leu Thr Asn
                395               400                405

GGA CAG ATG TCC ACC CCT GAG ACT CCA CAG CCA TCA CCA CCA AGT         1318
Gly Gln Met Ser Thr Pro Glu Thr Pro Gln Pro Ser Pro Pro Ser
                410               415                420

GGC TCT GGA TCT GAA TCC TAC AAG CTC CTG CCA GGA GCC ATC ACC         1363
Gly Ser Gly Ser Glu Ser Tyr Lys Leu Leu Pro Gly Ala Ile Thr
                425               430                435

ACC ATC GTC AAG CCT CCC TCT GCC ATC CCC CAG CCA ACG ATC ACC         1408
Thr Ile Val Lys Pro Pro Ser Ala Ile Pro Gln Pro Thr Ile Thr
                440               445                450

AAG CAG GAA GCC ATC TAG CAAGCCGCCG GGGGGTGGGG GTGAGGCTTC            1456
Lys Gln Glu Ala Ile
                455

TGCTGGCTCA CACCCTCAGA GAGCGCCTGG GTGTAACTTA GTCACGGCAA AGAGGATGTG   1516

ACAAGAGGGA CCAGTCCCAG AGCAGCCACT GAAAGGGCTT GTAGGCCCAA AAACATGCGC   1576

TGAGGATCGC ATGCATTGCC ACCCCTGACC CCACATCCGG AGGGCAGGGC TTTGCCTTGA   1636

GGAGACCCCG GCGGGGGGAT GTCTTCCGCT GCCTGGACTC TTCTCAAGTT GAAGCTGCCG   1696

TCTTCATCTT CCCCTCATAT CTTCCCTCAA CTTCTTCACC CCTAAAGGAC AACCATCTGC   1756

AG                                                                 1758
```

(2) INFORMATION FOR SEQ ID NO: 2:

(i) SEQUENCE CHARACTERISTICS:
        (A) LENGTH: 23 base pairs

```
        (B) TYPE: nucleic acid
        (C) STRANDEDNESS: single
        (D) TOPOLOGY: linear (ii) MOLECULE TYPE: genomic DNA (iii) HYPOTHETICAL: yes (iv) ANTI-SENSE: no (v) FRAGMENT TYPE: polymerase chain reaction product (vi) ORIGINAL SOURCE:
        (A) ORGANISM: Rat liver nuclei (vii) IMMEDIATE SOURCE:
        (B) CLONE: cloned into polylinker region of
            Bluescript KS(+)

(ix) FEATURE:
        (A) NAME/KEY:  primer for pep 1S
        (B) LOCATION:  Near zinc finger
        (C) IDENTIFICATION METHOD:  synthesized to pep 1
        (D) OTHER INFORMATION:

(xi) SEQUENCE DESCRIPTION: SEQ ID NO: 2:

CCMTCCSANG GNGCNAAYYT NAA                                              23

(2) INFORMATION FOR SEQ ID NO: 3:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (ii) MOLECULE TYPE: genomic DNA (iii) HYPOTHETICAL: yes (iv) ANTI-SENSE: yes (v) FRAGMENT TYPE: polymerase chain reaction
            product (vi) ORIGINAL SOURCE:
        (A) ORGANISM: rat liver nuclei (vii) IMMEDIATE SOURCE:
        (B) CLONE: cloned into polylinker region of
            Bluescript KS(+)

(ix) FEATURE:
        (A) NAME/KEY:  antisense of primer for pep 1A
        (B) LOCATION:  near zinc finger
        (C) IDENTIFICATION METHOD:  synthesized to pep 2
        (D) OTHER INFORMATION:

(xi) SEQUENCE DESCRIPTION: SEQ ID NO: 3:

TTAGGTTNGC NCCYTSNSNN GG                                               22

(2) INFORMATION FOR SEQ ID NO: N at locations 20 and 29 can be Y or A (i) SEQUENCE CHARACTERISTICS:
        (A) LENGTH: 31 base pairs
        (B) TYPE: nucleic acid
        (C) STRANDEDNESS: single
        (D) TOPOLOGY: linear (ii) MOLECULE TYPE: genomic DNA (iii) HYPOTHETICAL: yes (iv) ANTI-SENSE: no
```

(v) FRAGMENT TYPE: polymerase chain reaction product (vi) ORIGINAL SOURCE:
            (A) ORGANISM: Rat liver nuclei (vii) IMMEDIATE SOURCE:
            (B) CLONE: polylinker region of Bluescript KS(+)

(ix) FEATURE:
            (A) NAME/KEY:  primer 2S
            (B) LOCATION:  entire sequence near zinc finger
                also at 20 and 29
            (C) IDENTIFICATION METHOD:

(xi) SEQUENCE DESCRIPTION: SEQ ID NO: 4:

CATCTAGAAT TGAGCAGATN CARTTYATNA A                                               31

(2) INFORMATION FOR SEQ ID NO: N at locations 14 and 23 can be T or
            unknown (i) SEQUENCE CHARACTERISTICS:
            (A) LENGTH: 31 base pairs
            (B) TYPE: nucleic acid
            (C) STRANDEDNESS: single
            (D) TOPOLOGY: linear (ii) MOLECULE TYPE: genomic DNA (iii) HYPOTHETICAL: yes (iv) ANTI-SENSE: yes (v) FRAGMENT TYPE: polymerase chain reaction product (vi) ORIGINAL SOURCE:
            (A) ORGANISM: Rat liver nuclei (vii) IMMEDIATE SOURCE:
            (B) CLONE: polylinker region of Bluescript KS(+)

(ix) FEATURE:
            (A) NAME/KEY:  antisense to pep 2
            (B) LOCATION:  entire sequence near zinc finger
                also at 14 and 23
            (C) IDENTIFICATION METHOD:

(xi) SEQUENCE DESCRIPTION: SEQ ID NO: 5:

AACGTCAGAG CTTNATRAAY TGNATYTGYT C                                               31

(2) INFORMATION FOR SEQ ID NO: 6:

(i) SEQUENCE CHARACTERISTICS:
            (A) LENGTH: 23 base pairs
            (B) TYPE: nucleic acid
            (C) STRANDEDNESS: single
            (D) TOPOLOGY: linear (ii) MOLECULE TYPE: genomic DNA (iii) HYPOTHETICAL: yes (iv) ANTI-SENSE: no (v) FRAGMENT TYPE: polymerase chain reaction product (vi) ORIGINAL SOURCE:
            (A) ORGANISM: Rat liver nuclei (vii) IMMEDIATE SOURCE:
            (B) CLONE: polylinker region of Bluescript KS(+)

(ix) FEATURE:
            (A) NAME/KEY:  sense of pep 3
            (B) LOCATION:  near zinc finger
            (C) IDENTIFICATION METHOD:

(D) OTHER INFORMATION:

(xi) SEQUENCE DESCRIPTION: SEQ ID NO: 6:

GAGGCTGTNC ANAAYGANMG NGA                                           23

(2) INFORMATION FOR SEQ ID NO: 7:

(i) SEQUENCE CHARACTERISTICS:
            (A) LENGTH: 23 base pairs
            (B) TYPE: nucleic acid
            (C) STRANDEDNESS: single
            (D) TOPOLOGY: linear (ii) MOLECULE TYPE: genomic DNA (iii) HYPOTHETICAL: yes (iv) ANTI-SENSE: yes (v) FRAGMENT TYPE: polymerase chain reaction product (vi) ORIGINAL SOURCE:
            (A) ORGANISM: Rat liver nuclei (vii) IMMEDIATE SOURCE:
            (B) CLONE: polylinker region of Bluescript KS(+)

(ix) FEATURE:
            (A) NAME/KEY: primer 3S
            (B) LOCATION: entire sequence near zinc finger
                also at 3 and 5
            (C) IDENTIFICATION METHOD:

(xi) SEQUENCE DESCRIPTION: SEQ ID NO: 7:

TCBCKCTCNT TYTGNACNGC YTC                                           23

(2) INFORMATION FOR SEQ ID NO: 8:

(i) SEQUENCE CHARACTERISTICS:
            (A) LENGTH: 33 base pairs
            (B) TYPE: nucleic acid
            (C) STRANDEDNESS: single
            (D) TOPOLOGY: linear (ii) MOLECULE TYPE: DNA (genomic)

(iv) ANTI-SENSE: NO (xi) SEQUENCE DESCRIPTION: SEQ ID NO: 8:

GATCCTCGGG AAAGGGAAAC CGAAACTGAA GCC                                33

(2) INFORMATION FOR SEQ ID NO: 9:

(i) SEQUENCE CHARACTERISTICS:
            (A) LENGTH: 26 base pairs
            (B) TYPE: nucleic acid
            (C) STRANDEDNESS: single
            (D) TOPOLOGY: linear (ii) MOLECULE TYPE: DNA (genomic)

(iv) ANTI-SENSE: NO (xi) SEQUENCE DESCRIPTION: SEQ ID NO: 9:

TCGAGGCAAG GTTCATATTT GTGTAG                                        26

(2) INFORMATION FOR SEQ ID NO: 10:

(i) SEQUENCE CHARACTERISTICS:
            (A) LENGTH: 27 base pairs
            (B) TYPE: nucleic acid (C) STRANDEDNESS: single
            (D) TOPOLOGY: linear (ii) MOLECULE TYPE: other nucleic acid
            (A) DESCRIPTION: /desc = "Oligonucleotides"

(iii) HYPOTHETICAL: NO (xi) SEQUENCE DESCRIPTION: SEQ ID NO: 10:

TCGACCCTAG GCAAGGTTCA TATGGCC                                                27

(2) INFORMATION FOR SEQ ID NO: 11:

(i) SEQUENCE CHARACTERISTICS:
            (A) LENGTH: 27 base pairs
            (B) TYPE: nucleic acid
            (C) STRANDEDNESS: single
            (D) TOPOLOGY: linear (ii) MOLECULE TYPE: other nucleic acid
            (A) DESCRIPTION: /desc = "Oligonucleotides"

(iii) HYPOTHETICAL: NO (xi) SEQUENCE DESCRIPTION: SEQ ID NO: 11:

TCGACTCTCT GCAAGGGTCA TCAGTAC                                                27

(2) INFORMATION FOR SEQ ID NO: 12:

(i) SEQUENCE CHARACTERISTICS:
            (A) LENGTH: 26 base pairs
            (B) TYPE: nucleic acid
            (C) STRANDEDNESS: single
            (D) TOPOLOGY: linear (ii) MOLECULE TYPE: other nucleic acid
            (A) DESCRIPTION: /desc = "Oligonucleotides"

(iii) HYPOTHETICAL: NO (xi) SEQUENCE DESCRIPTION: SEQ ID NO: 12:

TCGAGCGCTG GGCAAAGGTC ACCTGC                                                 26

(2) INFORMATION FOR SEQ ID NO: 13:

(i) SEQUENCE CHARACTERISTICS:
            (A) LENGTH: 28 base pairs
            (B) TYPE: nucleic acid
            (C) STRANDEDNESS: single
            (D) TOPOLOGY: linear (ii) MOLECULE TYPE: other nucleic acid
            (A) DESCRIPTION: /desc = "Oligonucleotides"

(iii) HYPOTHETICAL: NO (xi) SEQUENCE DESCRIPTION: SEQ ID NO: 13:

AGCAAACAGG GGCTAAGTCC ACTGGCTG                                               28

(2) INFORMATION FOR SEQ ID NO: 14:

(i) SEQUENCE CHARACTERISTICS:
            (A) LENGTH: 12 base pairs
            (B) TYPE: nucleic acid
            (C) STRANDEDNESS: single
            (D) TOPOLOGY: linear (ii) MOLECULE TYPE: other nucleic acid
            (A) DESCRIPTION: /desc = "HNF-4 Consensus"

(iii) HYPOTHETICAL: YES (xi) SEQUENCE DESCRIPTION: SEQ ID NO: 14:

KGCWARGKYC AY                                                                              12

(2) INFORMATION FOR SEQ ID NO: 15:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "Oligonucleotides"

(iii) HYPOTHETICAL: NO (xi) SEQUENCE DESCRIPTION: SEQ ID NO: 15:

AGCTCTCAGG TCACTGTGAC CTGA                                                                 24

(2) INFORMATION FOR SEQ ID NO: 16:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "Oligonucleotides"

(iii) HYPOTHETICAL: NO (xi) SEQUENCE DESCRIPTION: SEQ ID NO: 16:

AGCTCTCAGG TCATGACCTG A                                                                    21

(2) INFORMATION FOR SEQ ID NO: 17:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "Oligonucleotides"

(iii) HYPOTHETICAL: NO (xi) SEQUENCE DESCRIPTION: SEQ ID NO: 17:

AGCTCTCAGA ACACTGTGTT CTGA                                                                 24

(2) INFORMATION FOR SEQ ID NO: 18:

(i) SEQUENCE CHARACTERISTICS:
        (A) LENGTH: 455 amino acids
        (B) TYPE: amino acids
        (D) TOPOLOGY: linear (ii) MOLECULE TYPE: protein
        (A) DESCRIPTION: /desc = "Amino Acids"

(iii) HYPOTHETICAL: YES (xi) SEQUENCE DESCRIPTION: SEQ ID NO: 18:

Met Asp Met Ala Asp Tyr Ser Ala Ala Leu Asp Pro Ala Tyr Thr
 1               5                  10                  15

Thr Leu Glu Phe Glu Asn Val Gln Val Leu Thr Met Gly Asn Asp
                20                  25                  30

-continued

```
Thr Ser Pro Ser Glu Gly Ala Asn Leu Asn Ser Ser Asn Ser Leu
             35                  40                  45
Gly Val Ser Ala Leu Cys Ala Ile Cys Gly Asp Arg Ala Thr Gly
             50                  55                  60
Lys His Tyr Gly Ala Ser Ser Cys Asp Gly Cys Lys Gly Phe Phe
             65                  70                  75
Arg Arg Ser Val Arg Lys Asn His Met Tyr Ser Cys Arg Phe Ser
             80                  85                  90
Arg Gln Cys Val Val Asp Lys Asp Lys Arg Asn Gln Cys Arg Tyr
             95                 100                 105
Cys Arg Leu Lys Lys Cys Phe Arg Ala Gly Met Lys Lys Glu Ala
            110                 115                 120
Val Gln Asn Glu Arg Asp Arg Ile Ser Thr Arg Arg Ser Ser Tyr
            125                 130                 135
Glu Asp Ile Ser Leu Pro Ser Ile Asn Ala Leu Leu Gln Ala Glu
            140                 145                 150
Val Leu Ser Gln Gln Ile Thr Ser Pro Ile Ser Gly Ile Asn Gly
            155                 160                 165
Asp Ile Arg Ala Lys Arg Ile Ala Ser Ile Thr Asp Val Cys Glu
            170                 175                 180
Ser Met Lys Glu Gln Leu Leu Val Leu Val Glu Trp Ala Lys Tyr
            185                 190                 195
Ile Pro Ala Phe Cys Glu Leu Leu Leu Asp Asp Gln Val Ala Leu
            200                 205                 210
Leu Arg Ala His Ala Gly Glu His Leu Leu Leu Gly Ala Thr Lys
            215                 220                 225
Arg Ser Met Val Phe Lys Asp Val Leu Leu Leu Gly Asn Asp Tyr
            230                 235                 240
Ile Val Pro Arg His Cys Pro Glu Leu Ala Glu Met Ser Arg Val
            245                 250                 255
Ser Ile Arg Ile Leu Asp Glu Leu Val Leu Pro Phe Gln Glu Leu
            260                 265                 270
Gln Ile Asp Asp Asn Glu Tyr Ala Cys Leu Lys Ala Ile Ile Phe
            275                 280                 285
Phe Asp Pro Asp Ala Lys Gly Leu Ser Asp Pro Gly Lys Ile Lys
            290                 295                 300
Arg Leu Arg Ser Gln Val Gln Val Ser Leu Glu Asp Tyr Ile Asn
            305                 310                 315
Asp Arg Gln Tyr Asp Ser Arg Gly Arg Phe Gly Glu Leu Leu Leu
            320                 325                 330
Leu Leu Pro Thr Leu Gln Ser Ile Thr Trp Gln Met Ile Glu Gln
            335                 340                 345
Ile Gln Phe Ile Lys Leu Phe Gly Met Ala Lys Ile Asp Asn Leu
            350                 355                 360
Leu Gln Glu Met Leu Leu Gly Gly Ser Ala Ser Asp Ala Pro His
            365                 370                 375
Ala His His Pro Leu His Pro His Leu Met Gln Glu His Met Gly
            380                 385                 390
Thr Asn Val Ile Val Ala Asn Thr Met Pro Ser His Leu Thr Asn
            395                 400                 405
Gly Gln Met Ser Thr Pro Glu Thr Pro Gln Pro Ser Pro Pro Ser
            410                 415                 420
```

```
                                        -continued
Gly Ser Gly Ser Glu Ser Tyr Lys Leu Leu Pro Gly Ala Ile Thr
                425                 430             435

Thr Ile Val Lys Pro Pro Ser Ala Ile Pro Gln Pro Thr Ile Thr
                440             445             450

Lys Gln Glu Ala Ile
                455
```

LIVER ENRICHED TRANSCRIPTION FACTOR

CROSS-REFERENCE TO RELATED APPLICATIONS

The present Application is a Divisional Application of U.S. Ser. No. 09/038,217, filed on Mar. 11, 1998 now U.S. Pat. No. 6,025,196, Feb. 15, 2000 which is a Divisional Application of U.S. Ser. No. 08/661,330 filed on Jun. 14, 1996, now U.S. Ser. No. 5,849,485, issued Dec. 15, 1998 which is a Divisional Application of U.S. Ser. No. 08/078,222, filed Oct. 28, 1993, now U.S. Pat. No. 5,604,115, issued Feb. 18, 1997 which is a National filing of PCT/US91/09733, filed Dec. 23, 1991, which is a divisional of U.S. Ser. No. 07/631,720, filed Dec. 21, 1990, now abandoned, the disclosures of which are hereby incorporated by reference herein in their entireties. Applicants claim the benefits of these Applications under 35 U.S.C. §§120, and 371.

TECHNICAL FIELD OF THE INVENTION

The present invention relates to liver-related transcription factors and, in particular, to such factors as participate in the regulation of a variety of genes such as certain of the apolipoproteins involved in fat and cholesterol transport.

This invention also relates to antibodies which recognize the receptor HNF-4, and antiidiotype antibodies that recognize both antibodies-to HNF-4 and ligands which bind to HNF-4.

The invention also relates to antisense DNA and RNA molecules complementary to mRNA for HNF-4, and ribozymes which recognize the mRNA.

The invention also relates to methods of use of the aforementioned molecules, DNA sequences, antibodies, anti-idiotype antibodies, antisense molecules and ribozymes, for example in developing diagnostic and therapeutic agents to detect, inhibit or enhance binding to HNF-4.

It is a principal object of this invention to provide new means to study, diagnose, prevent and treat disease. More particularly, it is an object of this invention to provide molecules involved in binding to HNF-4, and to isolate other molecules which are themselves useful in inhibiting such binding.

This invention provides DNA sequences that code on expression for HNF-4, genomic DNA sequences for HNF-4, recombinant DNA molecules containing these DNA sequences, unicellular hosts transformed with these DNA molecules, processes for producing such receptors, and proteins essentially free of normally associated animal proteins.

The present invention also provides for antibody preparations reactive for HNF-4.

Monoclonal antibodies recognizing ligands to HNF-4 can inhibit ligand binding directly or by binding or otherwise interacting with a third molecule. Such molecules may act, for example, by changing the surface conformation of the ligand so that its affinity for the HNF-4 is reduced.

This invention also provides recombinant DNA molecules containing HNF-4DNA sequences and unicellular hosts transformed with them. It also provides for HNF-4 proteins essentially free of normally associated animal proteins, methods for producing HNF-4, and monoclonal antibodies that recognize HNF-4.

This invention further provides methods for using antisense nucleic acids and ribozymes to inhibit HNF-4 expression. The invention also relates to methods for identifying binding inhibitors by screening molecules for their ability to inhibit binding of HNF-4 to its ligand. It provides methods for identifying ligands. One such method involves using anti-idiotypic antibodies against antibodies that recognize HNF-4 or HNF-4 ligands.

BACKGROUND OF THE INVENTION

Cell type specificity is based on differential gene expression which is in turn determined, at least in part, by the particular set of transcription factors present and active in a given cell at a given time. Many such factors have been identified and characterized, particularly in the liver where there is a wide range of transcriptionally controlled genes (McKnight & Palmiter, 1979; Derman et al., 1981). Some transcription factors, such as AP-1 and Sp-1, seem to be present in all cells at all times but other factors have a more limited distribution. Whether there is a discernible logic that explains the distribution of the many factors has yet to be determined. Two aspects of this problem are particularly important. The first aspect is to determine whether the distribution of factors in different issues is controlled at the level of transcription. If so, then a cascade of transcriptional regulation that ultimately results in cell specificity is indicated. The second issue is whether any particular factor is central to the accomplishment of a particular metabolic or physiologic goal. Such a goal might be suggested by factors acting on an interrelated set of genes.

These issues have begun to be addressed by the dissection and analysis of the promoter/enhancer regions of genes expressed primarily in hepatocytes by the present applicants and others (Johnson, 1990). The DNA elements that confer cell specific expression have been defined by transient transfection into cultured cells (e.g., hepatoma vs. HeLa cells) and/or in vitro transcription assays, and the proteins that bind to these elements have been identified by DNA binding assays using crude liver nuclear extracts. In this way, at least four distinct protein factors that are abundant in liver have been found thus far: HNF1 (LF-B1) (Courtois et al., 1987; Monaci et al., 1988), C/EBP (Johnson et al., 1987), HNF-3 and HNF-4 (Costa et al., 1989). HNF1, a homeodomain protein (Frain et al., 1989; Baumhueter et al., 1990), C/EBP, the original leucine zipper protein (Landschulz et al., 1988), and most recently HNF-3A, a DNA binding protein that has no similarity to known transcription factor families (Lai et al., 1990) have all been purified and cloned so that distribution and regulation of each can be determined.

The following publications are cited in the body of the patent application. Each of the publications is incorporated herein by reference:

Ahe, von der D., Janich, S., Scheidereit, C., Renkawitz, R., Schutz, G., and Beato, M. (1985). Glucocorticoid and progesterone receptors bind to the same sites in two hormonally regulated promoters. *Nature*, 313, 706–709.

Baumhueter, S., Mendel, D. B., Conley, P. B., Kuo, C. J., Turk, C., Graves, M. K., Edwards, C. A., Courtois, G., and Crabtree, G. R. (1990). HNF-1 shares three sequence motifs with the POU domain proteins and is identical to LF-B1 and APF. *Genes and Development* 4, 372–379.

Beato, M. (1989). Gene regulation by steroid hormones. *Cell* 56, 335–344.

Birkenmeier, E. H., Gwynn, B., Howard, S., Jerry, J., Gordon, J. I., Landsdhulz, W. H., and McKnight, S. L. (1989). Tissue-specific expression, developmental regulation and mapping of the gene encoding CCAAT/enhancer binding protein. *Genes and Development*, 3, 1146–1156.

Brand, N., Petkovich, M., Krust, A., Chambon, P., de The, H., Marchio, A., Tiollais, P., and Dejean, A. (1988). Identification of a second human retinoic acid receptor. *Nature*, 332, 850–853.

Breslow, J. (1988). Apolipoprotein genetic variation and human disease. Physiol. Reviews, 68, 85–132.

Capon, D. J. et al. (1989). Designing CF4 immunoadhesins for AIDS therapy. Nature, 337, 525–531.

Carlsson, R., and Glad, C. (June, 1989). Monoclonal antibodies into the '90s. Bio/Techblogy, 7, 567–573.

Cate, R. et al. (1986). Isolation of the bovine and human genes for Mullerian inhibiting substance and expression of the human gene in animal cells. Cell, 45, 685–598.

Cech, T. R. (1988). Ribozymes and their medical implications. J. Amer. Med. Assn., 260, 3030–3044.

Chomezynski, P. and Sacchi, N. (1987). Single-step method of RNA isolation by acid guanidinium thiocyanate-phenol-chloroform extraction. Anal. Biochem., 162, 156–159.

Costa, R. H., Lai, E., and Darnell, J. E., Jr. (1986). Transcriptional control of the mouse prealbumin (transthyretin) gene: both promoter sequences and a distinct enhancer are cell specific. Mol. and Cell. Biol., 6, 4697–4708.

Costa, R. H., Grayson, D. R., Xanthopoulos, K. G., and Darnell, J. E., Jr. (1988). A liver-specific DNA-binding protein recognizes multiple nucleotide sites in regulatory regions of transthyretin, a1-antitrypsin, albumin, and simian virus 40 genes. Proc. Natl. Acad. Sci., 85, 3840–3844.

Costa, R. H., Grayson, D. R. and Darnell, J. E. Jr. (1989). Multiple hepatocyte-enriched nuclear factors function in the regulation of transthyretin and al-antitrypsin genes. Mol. and Cell. Biol., 9, 1415–1425.

Costa, R. H., Van Dyke, T. A., Yan, C., Kuo, F., and Darnell, J. E., Jr. (1990). Similarities in transthyretin gene expression and differences in transcription factors: liver and yolk sac compared to choroid plexus. Proc. Natl. Acad. Sci. USA, 87, 6589–6593.

Courtois, G., Morgan, J. G., Campbell, L. A., Fourel, G. and Crabtree, G. R. (1987). Interaction of a liver-specific nuclear factor with the fibrinogen and al-antitrypsin promoters. Science, 238, 688–692.

Danielsen, M., Hinck, L., and Ringold, G. M. (1989). Two amino acids within the knuckle of the first zinc finger specify DNA response element activation by the glucocorticoid receptor. Cell, 57, 1131–1138.

Davis, M. M. (1986). Subtractive cDNA hybridization and the T-cell receptor gene. Handbook of Experimental Immunology in Four Volumes, 4th ed. Blackwell Scientific Publications, Oxford, England, 76.1–76.13.

Davis, M. M. et al. (1984). Cell type-specific cDNA probes and the murine I region: The localization and orientation of ad. Proc. Natl. Acad. Sci. USA, 81, 2194–2198.

Derman, E., Krauter, K., Walling, L., Weinberger, C., Ray, M. and Darnell, J. E. Jr. (1981). Transcriptional control in the production of liver-specific mRNAs. Cell, 23, 731–739.

de The, H., Marchio, A., Tiollais, P., and Dejean, A. (1987). A novel steroid thyroid hormone receptor-related gene inappropriately expressed in human hepatocellular carcinoma. Nature, 330, 667–670.

Duguid, J. R. et al. (1988). Isolation of cDNAs of scrapie-modulated RNMAs by subtractive hybridization of a cDNA library. Proc. Natl. Acad. Sci. USA, 85, 5738–5742.

Evans, R. M. (1988). The steroid and thyroid hormone receptor superfamily. Science, 240, 889–895.

Fawell, S. E., Lees, J. A., White, R. and Parker, M. G. (1990). Characterization and colocalization of steroid binding and dimerization activities in the mouse estrogen receptor. Cell, 60, 953–962.

Feinberg, A. P., and Vogelstein, B. (1983). A technique for radiolabeling DNA restriction endonuclease fragments to high specific activity. Anal. Biochem., 132, 6–13.

Fisher, R. A. et al. (1988). HIV infection is blocked in vitro by recombinant soluble CD4. Nature, 331, 76–78.

Forman, B. M., Yan, C. R., Au, M., Casanova, J., Ghysdael, J., and Samuels, H. H. (1989). A domain containing leucine-zipper-like motifs mediate novel in vivo interactions between the thyroid hormone and retinoic acid receptors. Mol. End., 3, 1610–1626.

Forman, B. M. and Samuels, H. H. (1990). Interactions among a subfamily of nuclear hormone receptors: The regulatory zipper model. Mol. End. 4, 1293–1301.

Frain, M., Swart, G., Monaci, P., Nicosia, A., Stampfli, S., Frank, R., and Cortese, R. (1989). The liver-specific transcription factor LF-Bl contains a highly diverged homeobox DNA binding domain. Cell, 59, 145–157.

Fried, M. and Crothers, D. M. (1981). Equilibria and kinetics of lac repressor-operator interactions by polyacrylamide gel electrophoresis. Nucleic Acids Res., 9, 6505–6525.

Giguere, V., Yang, N., Segui, P., and Evans, R. M. (1988). Identification of a new class of steroid hormone receptors. Nature, 331, 91–94.

Glass, C. K., Lipkin, S. M., Devary, O. V., and Rosenfeld, M. G. (1989). Positive and negative regulation of gene transcription by a retinoic acid-thyroid hormone receptor heterodimer. Cell, 59, 697–708.

Gorman, C. M., Moffat, L. F. and Howard, B. H. (1982). Recombinant genomes which express chloramphenicol acetyltransferase in mammalian cells. Mol. Cell. Biol., 2, 1044–1051.

Gorman, C. M., Howard, B. H. and Reeves, R. (1983). Expression of recombinant plasmids in mammalian cells is enhanced by sodium butyrate. Nucleic Acids Res., 11, 7631–7648.

Gorski, K., Carneiro, M. and Schibler, U. (1986). Tissue-specific in vitro transcription from the mouse albumin promoter. Cell, 47, 767–776.

Green, N., Alexander, H., Olson, A., Alexander, S., Shinnick, T. M., Sutcliffe, J. G., and Lerner, R. A. (1982). Immunogenic structure of the influenza virus hemagglutinin. Cell, 28, 477–487.

Green, S., Walter, P., Kumar, V., Krust, A., Bornert, J. M., Argos, P., and Chambon, P. (1986). Human oestrogen receptor cDNA: Sequence, expression and homology to c/epb. Nature, 320, 134–139.

Green, S. and Chambon, P. (1988). Nuclear receptors enhance our understanding of transcription regulation. Trends Genet., 4, 309–314.

Gubler, U., and Hoffman, B. J. (1983). A simple and very efficient method for generating cDNA libraries. Gene, 25, 263–269.

Hamada, K., Gleason, S. L., Levi, B. Z., Hirschfeld, S., Appella, E., and Ozato, K. (1989). H-2 RIIBP, a member of the nuclear hormone receptor superfamily that binds to both the regulatory element of major histocompatibility class I genes and the estrogen response element. Proc. Natl. Acad. Sci. USA, 86, 8289–8293.

Hambor, J. E. et al. (1988). Functional consequences of antisense RNA-mediate inhibition of CD8 surface expression in a human T cell clone. J. Exp. Med., 168, 1237–1245.

Hardon, E. M., Frain, M., Paonessa, G. and Cortese, R. (1988). Two distinct factors interact with the promoter regions of several liver-specific genes. The EMBO J., 7, 1711–1719.

Harlow, E. and Lane, D. (1988). Antibodies: A laboratory manual. (Cold Spring Harbor, N.Y.: Cold Spring Harbor Lab.)

Hasselhoff, J., and Gerlach, W. L. (1988). Simple RNA enzymes with new and highly specific endoribonuclease activities. Nature, 334, 585–591.

Hedrick, S. M. et al. (1984). Isolation of cDNA clones encoding T cell-specific membrane-associated proteins. Nature, 308, 149–153.

Ito, Y., Azrolan, N., O'Connell, A., Walsh, A., and Breslow, J. L. (1990) Hypertriglyceridemia as a result of human apoCIII gene expression in transgenic mice. *Science*, 249, 790–793.

Johnson, P. F., Landschulz, W. H., Graves, B. J., and McKnight, S. L. (1987). Identification of a rat liver nuclear protein that binds to the enhancer core element of three animal viruses. *Genes and Development*, 1, 133–146.

Johnson, P. F. (1990). Transcriptional activators in hepatocytes. In *Cell Growth and Differentiation*, 1, 47–52.

Kadonaga, J. T., and Tjian, R. (1986). Affinity purification of sequence-specific DNA binding proteins. *Proc. Natl. Acad. Sci. USA*, 83, 5889–5893.

Kennedy, R. C. et al. (July, 1986). Anti-idiotypes and immunity. *Sci. Am.*, 255, 48–56.

Kozak, M. (1987). An analysis of 5'-noncoding sequences from 699 vertebrate messenger RNA's. *Nucleic Acids Res.*, 15, 8125–8143.

Krebs, E., Eisenman, R., Kuenzel, E., Litchfield, D., Lozeman, F., Lischer, B. and Sommercorn, J. (1988). Casein kinase II as a potentially important enzyme concerned with signal transduction. In *Molecular Biology of Signal Transduction*. (Cold Spring Harbor, N.Y.: Cold Spring Harbor Laboratory), p. 77–84.

Kumar, V., and Chambon, P. (1988). The estrogen receptor binds tightly to its responsive element as a ligand-induced homodimer. *Cell*, 55: 145–156.

Kuo, C. F., Xanthopoulos, K. G., and Darnell, J. E. Jr. (1990). Fetal and adult localization of C/EBP: evidence for combinatorial action of transcription factors in cell-specific gene expression. *Development*, 109, 473–481.

Lai, E., Prezioso, V. R., Smith, E., Litvin, O., Costa, R. H., and Darnell, J. E., Jr. (1990). HNF-3A, a hepatocyte-enriched transcription factor of novel structure is regulated transcriptionally. *Genes and Development*, 4, 1427–1436.

Landschulz, W. H., Johnson, P. F., Adashi, E. Y., Graves, B. J., and McKnight, S. L. (1988). Isolation of a recombinant copy of the gene encoding C/EBP. *Genes and Development*, 2, 786–800.

Lathe, E. (1985). Synthetic oligonucleotide probes deduced from amino acid sequence data: Theoretical and practical considerations. *J. Mol. Biol.*, 183, 1–12.

Leff, T., Reue, K., Melian, A., Culver, H., and Breslow, J. L. (1989). A regulatory element in the ApoCIII promoter that directs hepatic specific transcription binds to proteins in expressing and nonexpressing cell types. *The J. of Biol. Chem.*, 264, 16132–16137.

Lew, D. J., Decker, T., Strehlow, I. and Darnell, J. E. (1990). Overlapping elements in the GBP gene promoter mediate transcriptional induction by alpha and gamma-interferon. *Mol. Cell Biol.*, in press.

Li, Y., Shen, R.-F., Tsai, S. Y., and Woo, S. L. C. (1988). Multiple hepatic trans-acting factors are required for in vitro transcription of the human alpha-1-antitrypsin gene. *Mol. and Cell. Biol.*, 8, 4362–4369.

MacGregor, G. R., and Caskey, C. T. (1989). Construction of plasmids that express E. coli b-galactosidase in mammalian cells. *Nucleic Acids Res.*, 17, 2365.

Mader, S., Kumar, V., de Verneuil, H., and Chambon, P. (1989). Three amino acids of the oestrogen receptor are essential to its ability to distinguish an oestrogen from a glucocorticoid-responsive element. *Nature*, 338, 271–274.

Mangelsdorf, D. J., Ong, E. S., Dyck, J. A. and Evans, R. M. (1990). Nuclear receptor that identifies a novel retinoic acid response pathway. *Nature*, 345, 224–229.

Maniatis, T., Fritsch, E. F., and Sambrook, J. (1982). *Molecular cloning: A laboratory manual.* (Cold Spring Harbor, N.Y.: Cold Spring Harbor Lab.)

Marcus-Sekura, C. J. (1988). Techniques for using antisense oligonucleotides to study gene expression. *Anal. Biochem.*, 172, 289–295.

Matsudaira, P. (1987). Sequence from picomole quantities of proteins electroblotted onto polyvinylidene difluorid membranes. *The J. of Biol. Chem.*, 262, 10035–10038.

McKnight, G. S., and Palmiter, R. D. (1979). Transcriptional regulation of the ovalbumin and conalbumin genes by steroid hormones in chick oviduct. *J. Biol. Chem.*, 254, 9050–9058.

Mermod, N., O'Neill, E. A., Kelly, T. J. and Tjian, R. (1989). The proline-rich transcriptional activator of CTF/NF-1 is distinct from the replication and DNA binding domain. *Cell*, 58, 741–753.

Miyajiima, N., Kadowaki, Y., Fukushige, Shiminizu, S., Semba, K., Yamanashi, Y. H., Matsubara, K., Toyoshima, K., and Yamanoto, T. (1988). Identification of two novel members of erbA superfamily by molecular cloning: The gene products of the two are highly related to each other. *Nucleic Acids Res.*, 16:11057–11074.

Monaci, P., Nicosia, A., and Cortese, R. (1988). Two different liver-specific factors stimulate in vitro transcription from the human a1-antitrypsin promoter. *The EMBO J.*, 7, 2075–2087.

Mueller, C. R., Maire, P., and Schibler, U. (1990). DBP, a liver-enriched transcriptional activator, is expressed late in ontogeny and its tissue specificity is determined posttranscriptionally. *Cell*, 61, 279–291.

Pearson, W. R., and Lipman, D. J. (1988). Improved tools for biological sequence comparison. *Proc. Natl. Acad. Sci. USA*, 85, 2444–2448.

Puissant, C., and Houdebine, L. M. (1990). An improvement of the single-step method of RNA isolation by acid guanidinium thiocyanate-phenol-chloroform extraction. *BioTachniaues*, 8, 148–149.

Reue, K., Leff, T., and Breslow, J. L. (1988). Human apolipoprotein CIII gene expression is regulated by positive and negative Cis-acting elements and tissue-specific protein factors. *The J. of Biol. Chem.*, 263, 6857–6864.

Rosen, C. A., Sodroski, J. G. and Haseltine, W. A. (1985). The location of cis-acting regulatory sequences in the human T cell lymphotropic virus type III (HTLV-III/LAV) long terminal repeat. *Cell*, 41, 813–823.

Ruppert, S., Boshart, M., Bosch, F. X., Schmid, W., Fournier, R. E. K., and Schutz, G. (1990). Two genetically defined trans-acting loci coordinately regulate overlapping sets of liver-specific genes. *Cell*, 61, 895–904.

Ryseck, R. P., Macdonald-Bravo, H., Mattei, M. G., Ruppert, S., and Bravo, R. (1989). Structure, mapping and expression of a growth factor inducible gene encoding a putative nuclear hormonal binding receptor. *The EMBO J.*, 8, 3327–3335.

Saiki, R. K., Gelfand, D. H., Stoffel, S., Scharf, S. J., Higuchi, R., Horn, G. T., Mullis, K. B., and Erlich, H. A. (1988). Primer-directed enzymatic amplification of DNA with a thermostable DNA polymerase. *Science*, 239, 487–491.

Sanger, F., Nicklen, S., and Coulson, A. R. (1977). DNA sequencing with chain terminating inhibitors. *Proc. Natl. Acad. Sci. USA*, 74, 5463–5467.

Sambrook, J., Fritsch, E. F., and Maniatis, T. (1989). *Molecular cloning: A laboratory manual.* (Cold Spring Harbor, N.Y.: Cold Spring Harbor Laboratory).

Sargent, T. D. (1987). Isolation of differentially expressed genes. *Methods in Enzymol.*, 152, 423–447.

Schule, R., Umesono, K., Mangelsdorf, D. J., Bolado, J., Pike, J. W., and Evans, R. M. (1990). Jun-fos and receptors for vitamins A and D recognize a common response element in the human osteocalcin gene. *Cell*, 61, 497–504.

Seed, B. (1987). An LFA-3 cDNA encodes a phospholipid-linked membrane protein homologous to its receptor CD2. *Nature*, 329, 840–842.

Seed, B., and Aruffo, A. (1987). Molecular cloning of the CD2 antigen, the T-cell erythrocyte receptor, by a rapid immunoselection procedure. *Proc. Natl. Acad. Sci. USA*, 84, 3365–3369.

Tsai, S. Y., Carlstedt-Duke, J., Weigel, N. L., Dahlman, K., Gustafsson, J. A., Tsai, M. J., and O'Malley, B. W. (1988). Molecular interactions of steroid hormone receptor with its enhancer element: Evidence for receptor dimer formation. *Cell*, 55, 361–369.

Umesono, K., Giguere, V., Glass, C. K., Rosenfeld, M. G., and Evans, R. M. (1988). Retinoic acid and thyroid hormone induce gene expression through a common responsive element. *Nature*, 336, 262–265.

Umesono, K. and Evans, R. M. (1989). Determinants of target gene specificity for steroid/thyroid hormone receptors. *Cell*, 57, 1139–1146.

Vaulont, S., Puzenat, N., Kahn, A., and Raymondjean, M. (1989). Analysis by cell-free transcription of the liver-specific pyruvate kinase gene promoter. *Mol. and Cell. Biol.*, 9, 4409–4415.

Wang, L. H., Tsai, S. Y., Cook, R. G., Beattie, W. G., Tsai, M. J. and O'Malley, B. W. (1989). COUP transcription factor is a member of the steroid receptor superfamily. *Nature*, 340, 163–166.

Weinberger, C., Thompson, C. C., Ong, E. S., Lebo, R., Gruo, D. J., and Evans, R. M. (1986). The c/epb gene encodes a thyroid hormone receptor. *Nature*, 234, 641–646.

Wingender, E. (1990). Transcription regulating proteins and their recognition sequences. *Critical Reviews in Eukarvotic Gene Expression*, 1, 11–48.

Wysocki, L. J., and Sato, V. L. (1978). Panning for lymphocytes: A method for cell selection. *Proc. Natl. Acad. Sci. USA*, 75, 2844–2848.

Xanthopoulos, K. G., Mirkovitch, J., Decker, T., Kuo, C. F., and Darnell, J. E., Jr. (1989). Cell-specific transcriptional control of the mouse DNA-binding protein mC/EBP. *Proc. Natl. Acad. Sci. USA* 86, 4117–4121.

Yamasaki, K. et al. (1988). cloning and expression of the human interleukin-6 (BSF-2/IFNB2) receptor. *Science*, 241, 825–828.

Young, R. A. and Davis, R. W. (1983). Efficient isolation of genes by using antibody probes. *Proc. Natl. Acad. Sci. USA*, 80, 1194–1198.

SUMMARY OF THE INVENTION

The present invention comprises the purification and cloning of HNF-4 (hepatocyte nuclear factor 4), a factor originally detected in crude liver extracts as binding to a DNA element required for the transcription of the transthyretin (TTR) gene in hepatoma cells (Costa et al., 1989). An amino acid sequence comparison indicates that HNF-4 is a member of the superfamily of steroid/thyroid hormone receptors, ligand-dependent transcription factors which are known to play a role in differentiation and development (Evans, 1988; Green & Chambon, 1988; Beato, 1989). Whereas all of the other members to date fall into one of several subfamilies based on the nucleotide sequence of their recognition sites and the amino acid sequence of the zinc finger region (Umesono & Evans, 1989; Forman & Samuels, 1990), HNF-4 appears to represent a new subfamily.

More particularly, the present transcription factor is believed to play a regulatory role in the formation of lipid carrying proteins such as Apo CIII, as well as possible effects on Apo A1, Apo B, pyruvate kinase, α1 antitrypsin and glutamine synthetase. The cDNA sequence has been identified, and the invention relates to the DNA sequence, recombinant molecules based thereon, probes, sense and antisense RNA, and appropriately transformed host cells. Diagnostic and therapeutic applications are likewise contemplated.

(1A) SDS-PAGE Analysis of HNF-4Purification from Rat Liver Nuclei. Equivalent fractions of the starting material for each of the five last chromatographic steps and the peak fraction from the Mono Q column (Fxn 38) are shown in a Coomassie blue-stained gel. Oligo #1 and #2 are DNA affinity columns made from HNF-4P and APF-1 oligonucleotides, respectively. The band in Fxn 38 was estimated to be 54 kD based on the relative mobility of the Markers: 97, 66, 43 and 31 kD, top to bottom.

(1B) Characterization of the Binding Activity of Purified HNF-4Protein. The protein-DNA complexes from a mobility-shift assay (0.0625 $\mu$l Mono Q Fxn 38, 3 $\mu$g BSA, 0.5 $\mu$g poly(dl-dC) with seven $^{32}$P-labeled oligonucleotide probes (1 ng) with and without 50-fold excess competitor are shown. APF1, −151=−151 to −130, 4P=HNF4P, 4D=HNF4D as in Table 1. Nonspecific probes are from the mouse TTR promoter: −175=−175 to −151 (Costa et al., 1986), HNF3 (−111 to −85, Costa et al., 1989) and c/EBP (−186 kb, site 3, Costa et al., 1988).

(1C) Renaturation of HNF-4Protein. Fifty nanograms of Mono Q-purified HNF-4 was fractionated by SDS-PAGE and the protein eluted from a series of gel slices was tested for binding to the APF1 probe (0.5 ng) in a mobility-shift assay. Competitor was 50-fold excess unlabeled APF1 oligonucleotide. The protein gel lane shown was run in parallel to the dissected lane and is silver stained.

FIG. 2 —Characterization of Purified HNF-4

(2A) Footprint: Purified HNF-4 (Fxn 38) was used to footprint both strands of the −202 to −70 region of the mouse TTR promoter with copper phenanthroline. "F" and "B" are free and bound probe. "G" designates probe cleaved at G residues. The footprinted regions are shown in brackets; the arrow points to a hypersensitive site.

(2B) Phosphatase and Protease Studies: Purified HNF-4 (Fxn 38) was incubated at 37° C. (−) in the presence of calf intestine alkaline phosphatase (CIP), Protease V8 (V8), or Endoproteinase Lys C (lysC). The treated material was divided into four aliquots and tested in the mobility-shift assay with the designated probes.

Figure 3A:
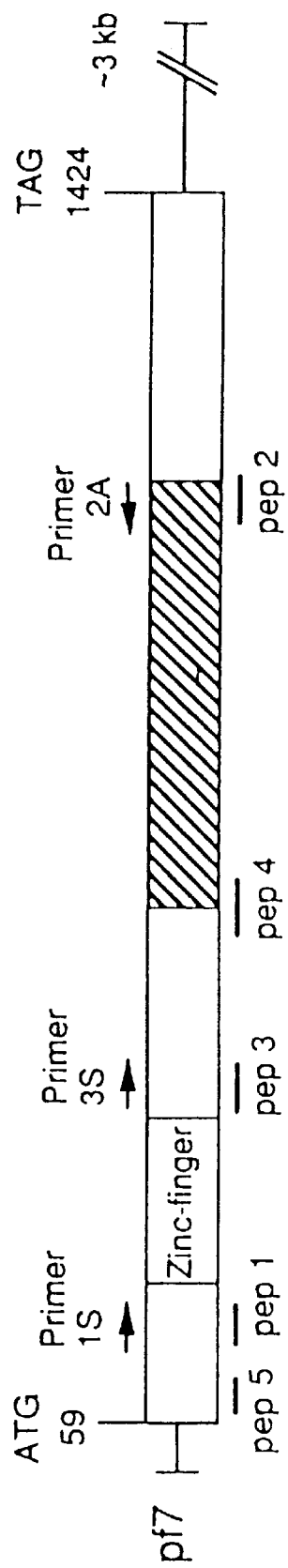

FIG. 3—Nucleotide Seauence of HNF-4 cDNA and Deduced Amino Acid Sequence of HNF-4Protein (3A) Schematic Representation of the Largest HNF-4 Clone, pf7. The positions of the peptides obtained from CNBr-cleavage of the purified protein (pep 1–5, plain lines) and the corresponding oligonucleotide primers which yielded products in PCR (arrows) (not drawn to scale) are shown. The open reading frame starting from the second in-frame methionine (see text) is delineated by the box. Numbers are the nucleotide positions from the beginning of the cDNA. The hatched area denotes the region used to probe a rat liver cDNA library for a full length clone. "Zinc finger" refers to the section of similarity to the steroid hormone receptors.

(3B) Partial Nucleotide Sequence (SEQ ID NO:1) and Deduced Amino Acid Sequence of HNF-4 cDNA. Sequence was obtained from the PCR products, pf7 and other cDNA isolates by the dideoxy method (Sanger et al., 1977). All regions were sequenced from at least two sources and were verified in the pf7 clone. The underlined amino acid sequences correspond to peptides 1.5. "+1" marks the probable initiator methionine. The bracket marks the knuckle of the first zinc finger and the (*) denotes the novel asp residue (see text). The sequence has been submitted to GenBank.

Figure 4:
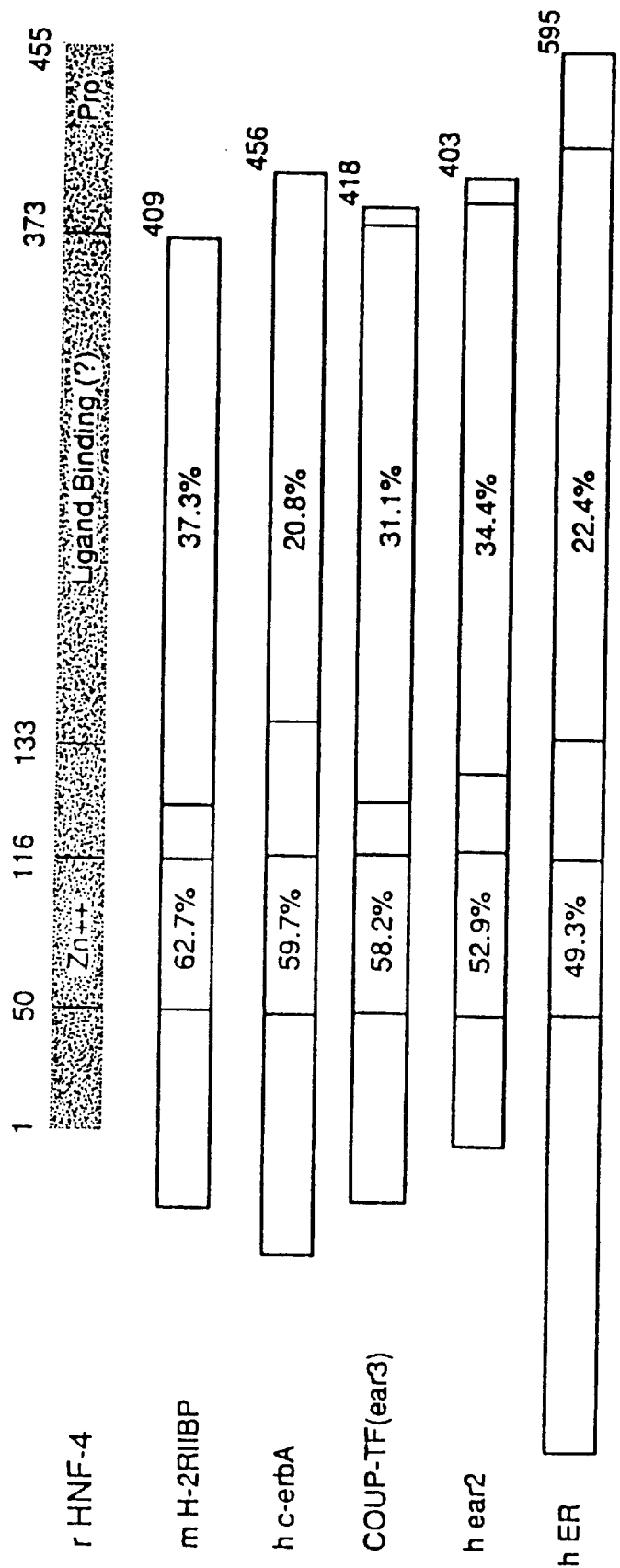

FIG. 4—Structural and Sequence Similarity Between HNF-4Protein and Steroid Hormone Receptors The primary amino acid sequences of rat HNF-4 was compared to members of the receptor superfamily using the FASTA program (Pearson & Lipman, 1988). Percentages denote amino acid identity within the zinc finger (Zn++) and ligand binding domains. "Pro" refers to a proline-rich domain. mH2-RIIBP is a mouse major histocompatibility class I regulatory protein (Hamada et al., 1989); h c-erbA is the human thyroid hormone receptor $T_3R_6$ (Weinberger et al., 1986 ); h ER is the human estrogen receptor (Green et al., 1986); COUP-TT(ear3) is the chicken ovalbumin upstream promoter transcription factor (Wang et al., 1989) and h ear 2 is a human v-erbA-related gene (Miyajima et al., 1988).

FIG. 5—In vitro Synthesized HNF-4Protein Binds to Its Recognition Site as a Dimer (5A) Schematic Representation of Truncated Forms of HNF-4 Protein Synthesized in vitro. pf7 DNA (in Bluescript SK(-)) was cut with the restriction enzymes indicated and transcribed in vitro with T3 RNA polymerase. The resulting mRNAs were translated with rabbit reticulate lysate (Promega) in the presence of $^3$H-leucine. The open box represents the 3 kb cDNA insert in pf7; the numbers are the nucleotide position of the start (ATG) and stop (TAG). The position of the cut site of the restriction enzymes and the length of the polypeptide in amino acids (aa) resulting from translation beginning at nucleotide 59 are given.

(5B) Mobility-Shift Assay of in vitro Synthesized HNF-4 Products. Reactions contained 0.5 ng $^{32}$P-labeled APF1 probe and 2 µg poly(dl-dC) in the presence of 25 ng unlabeled nonspecific (-) (-175 to -151 TTR) or specific (+) oligonucleotide (APF1) as competitor. Lanes 1-2: purified HNF-4 (Fxn 38); lanes 3-12: in vitro translation reactions (2 µl) as described in (A); lanes 13-14: Bovine Mosaid Virus (BMV) RNA added to the in vitro translation system as a negative control.

(5C) SDS-PAGE of in vitro Synthesized HNF-4Products. Autoradiogram of a 10% gel (treated with Enhance, NEN) containing 1 µl of translation reactions described in (5A). The positions of Coomassie-stained markers are shown on the left.

(5D) Mobility-Shift Assay Showing Dimer Formation. pf7 DNA cut with the restriction enzymes indicated was transcribed as in (5A). The resulting RNAs were mixed as noted and translated in vitro. The translation reactions were assayed as in (5B) in the presence of nonspecific competitor. The arrows indicate the complexes formed by heterodimeric protein; the arrow head marks the shift complex normally seen, presumably a homodimer.

Figure 6A:
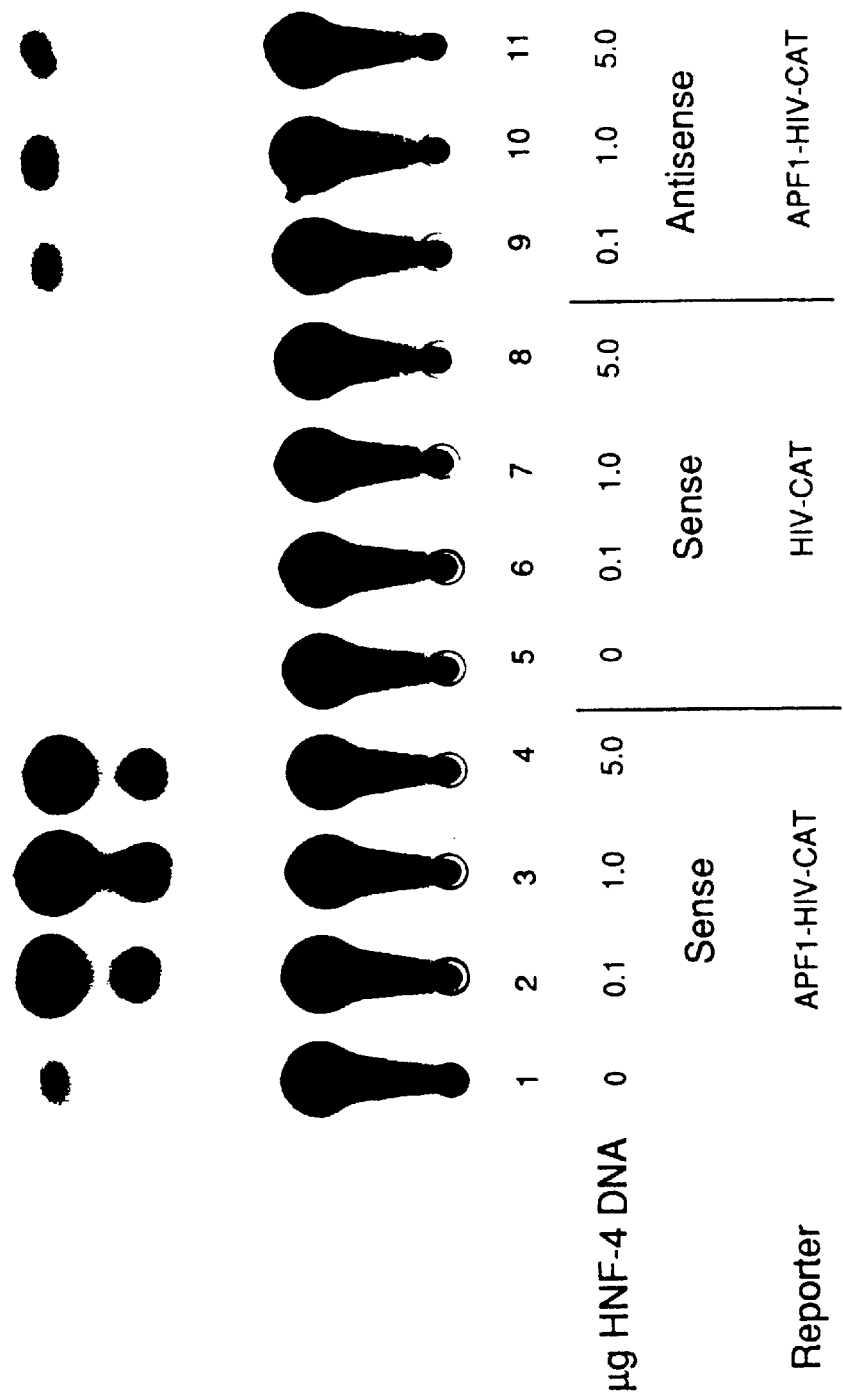
Figure 6B:
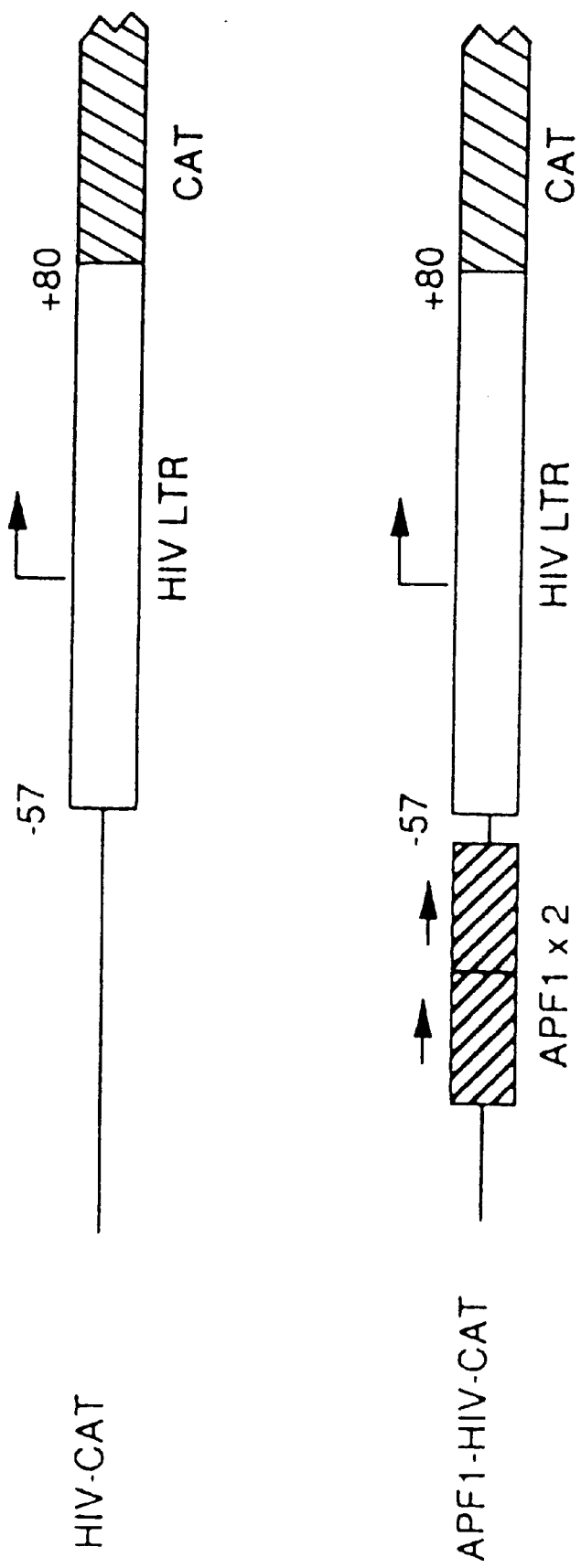

FIG. 6—Transcriptional Activation by HNF-4 cDNA

Top: autoradiogram of chloramphenicol acetyl transferase (CAT) assay. Bottom: schematic representation of reporter constructs. Expression vector DNA (0–5.0 µg) containing HNF-4 cDNA (the 3 kb insert of pf7) in either the sense or antisense direction was cotransfected into HeLa cells with a CAT reporter construct (2 µg), either lacking (HIV-CAT) or containing HNF-4 recognition sites (APF1-HIV-CAT). The long terminal repeat (LTR) of the human immunodeficiency virus (HIV) served as the basal promoter element. Densitometry of the autoradiogram indicated a 10–15 fold induction by HNF-4 cDNA (lane 2–4 compared to lanes 9–11).

Figure 7:
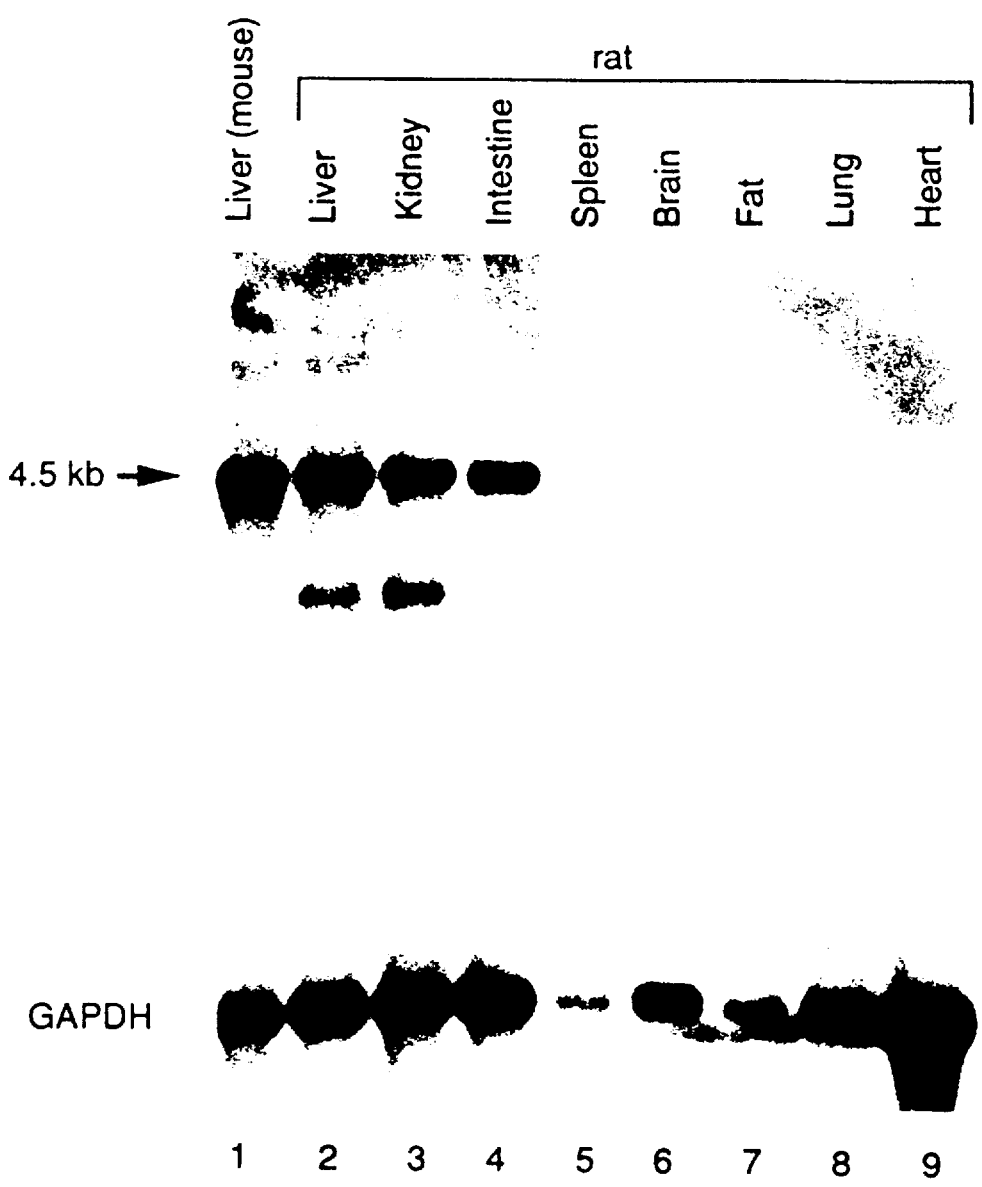

FIG. 7—Limited Tissue Distribution of HNF-4 mRNA

Northern blot analysis of poly(A)+ RNA from different rat and mouse tissues using an HNF-4 cDNA fragment as probe (top). A glyceraldehyde 3-phosphate dehydrogenase (GAPDH) probe served as a control (bottom).

Figure 8:
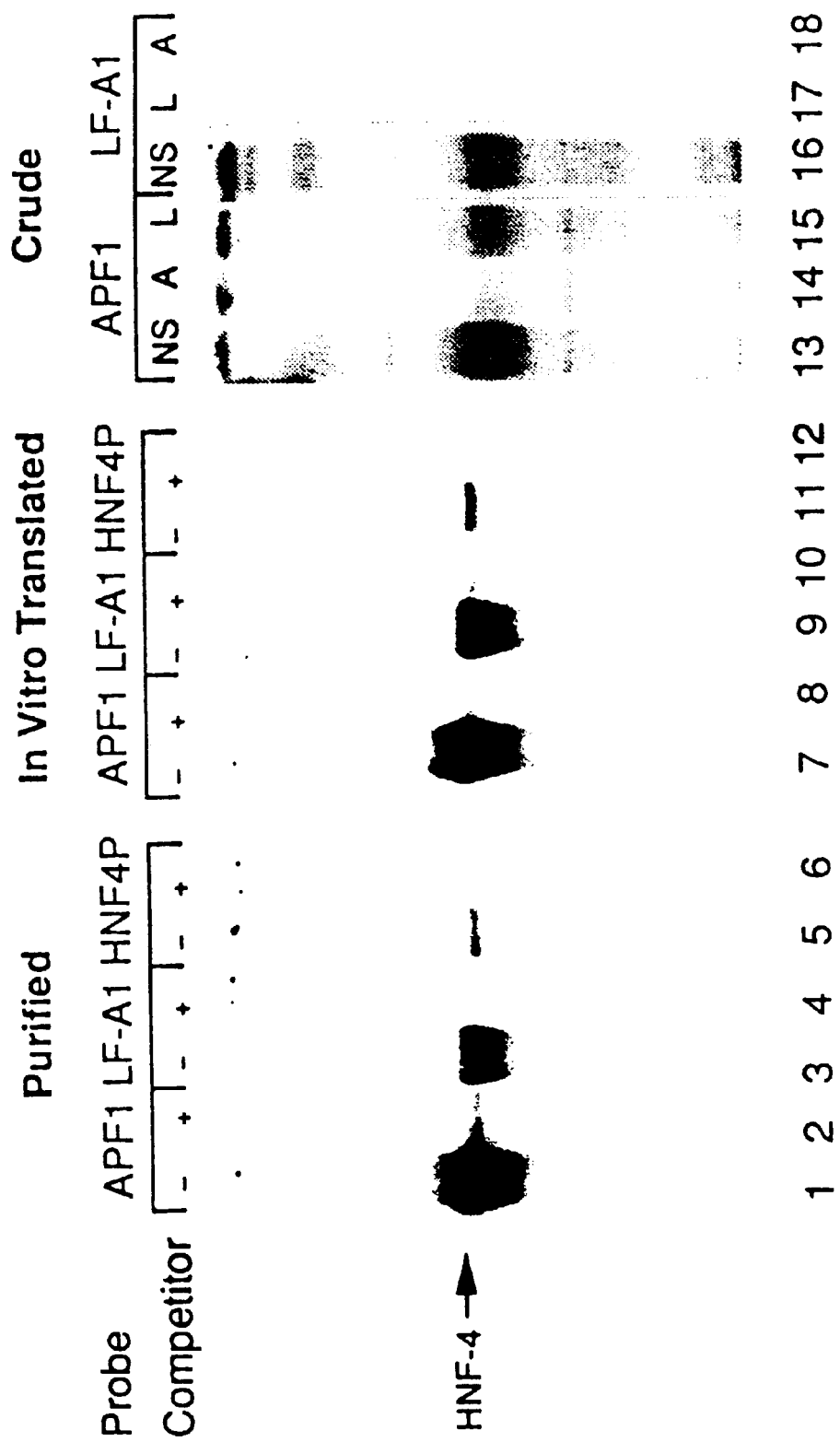

FIG. 8—HNF-4 Binds to an LF-A1 Site

Mobility-shift assay with either purified (MonoQ, Fxn 38, 0.03 µl) or in vitro translated HNF-F (Sph 1, FIG. 5, 2 µg poly(dl-dC) and 25 ng of unlabeled oligonucleotide, either nonspecific (-) (-175 to -151 TTR) or specific (+) oligonucleotide (APF1, LF-A1 or HNF4P) as competitor.

Figure 9:
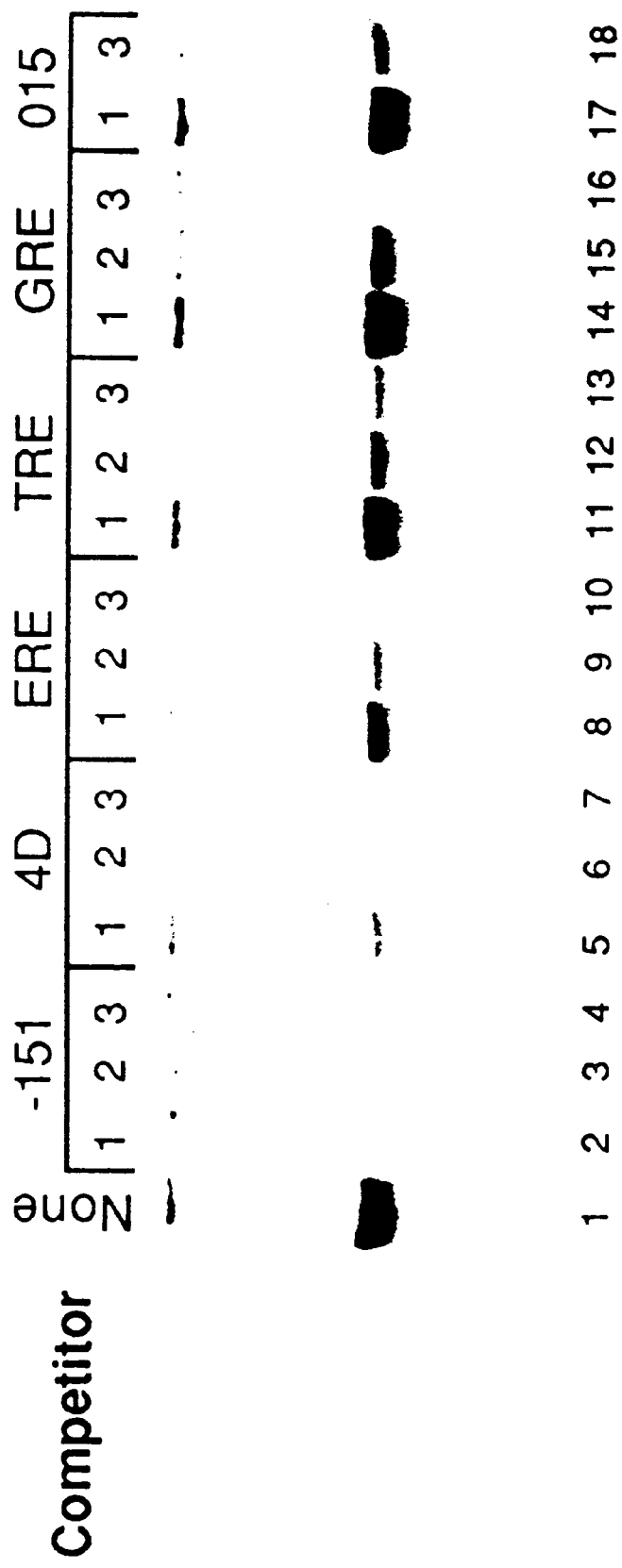

FIG. 9—HNF-4Does Not Significantly Bind ERE, TRE or GRE

Mobility-shift assay using purified HNF-4 (MonoQ, Fxn 38, 0.03 µl) in the presence of 3 µg BSA, 50 ng poly dl-dC, $^{32}$P-labeled, -151 to -130 TTR [probe (0.5 ng) and unlabeled oligonucletides as competitors as indicated: -151 -=-151-130 TTR, 4D =NHF4D and ERE, TRE and GRE are the estrogen, thyroid hormone and glucocorticoid response elements (see Table 1). 0.015 is an unrelated oligonucleotide, 5'-GATCCTCGGGAAAGGGAAACCG-AAACTGAAGCC-3'(SEQ ID NO:8). 1, 2 and 3 are 50-, 250- and 500-fold molar excess, respectively.

DETAILED DESCRIPTION

In accordance with this detailed description, the following definitions apply:

Expression control sequence—a DNA sequence that controls and regulates the transcription and translation of another DNA sequence.

Operatively linked—a DNA sequence is operatively linked to an expression control sequence when the expression control sequence controls and regulates the transcription and translation of that DNA sequence. The term "operatively linked" includes having an appropriate start signal (e.g., ATG) in front of the DNA sequence to be expressed and maintaining the correct reading frame to permit expression of the DNA sequence under the control of the expression control sequence and production of the desired product encoded by the DNA sequence. If a gene that one desires to insert into a recombinant DNA molecule does not contain an appropriate start signal, such a start signal can be inserted in front of the gene.

Antibody—an immunoglobulin molecule or functional fragment thereof, such as Fab, F(ab')$_2$ or dAB. An antibody preparation is reactive for a particular antigen when at least a portion of the individual immunoglobulin molecules in the preparation recognize (i.e., bind to) the antigen. An antibody preparation is nonreactive for an antigen when binding of the individual immunoglobulin molecules in the preparation to the antigen is not detectable by commonly used methods.

Standard hybridization conditions—salt and temperature conditions substantially equivalent to 5×SSC and 65° C. for both hybridization and wash.

DNA sequences—The DNA sequences of this invention refer to DNA sequences prepared or isolated using recombinant DNA techniques. These include cDNA sequences, DNA sequences isolated from their native genome, and synthetic DNA sequences. The term as used in the claims is not intended to include naturally occurring DNA sequences as they exist in nature.

HNF-4 (hepatocyte nuclear factor 4) is a protein enriched in liver extracts that binds to sites required for the transcription of the transthyretin (TTR) and apolipoprotein CIII (apoCIII) genes (Costa et al., 1989; Costa et al., 1990; Leff et al., 1989). HNF-4 protein (54 kD) has been purified and a cDNA clone isolated encoding the protein. HNF-4 is a member of the steroid hormone receptor superfamily with an unusual amino acid in the conserved "knuckle" of the first zinc finger (DGCKG). This and the fact that HNF-4 does not bind significantly to estrogen, thyroid hormone or glucocorticoid response elements indicate that HNF-4 may represent a new subfamily. HNF-4 binds to its recognition site as a dimer and activates transcription in a sequence-specific fashion in nonhepatic (HeLa) cells. HNF-4 mRNA is present in kidney and intestine as well as liver but is absent in other tissues. DNA binding data suggest that HNF-4 could be identical to liver factor A1 (LF-A1), a factor previously shown to regulate the transcription of the $\alpha$-1 antitrypsin, apolipoprotein A1 and pyruvate kinase genes.

As used herein, the word "ligand" means a substance which binds to a receptor, such as a hormone or growth substance. Inside a cell the ligand binds to a receptor protein, thereby creating a ligand/receptor complex, which in turn can bind to an appropriate hormone response element. Single ligands may have multiple receptors. For example, both the $T_3R_\alpha$ and the $T_3R_\beta$ bind thyroid hormone such as $T_3$. The ligand can be an agonist or an antagonist.

As used herein, the word "operative", in the phrase "operative hormone response element functionally linked to a ligand-responsive promoter and an operative reporter gene", means that the respective DNA sequences (represented by the terms "hormone response element", "ligand-responsive promoter" and "reporter gene") are operational, i.e., the hormone response element can bind with the DNA-binding domain of receptor protein (either wild-type or chimeric), the ligand-responsive promoter can control transcription of the reporter gene (upon approrpiate activation by a HRE/-receptor protein/ligand complex) and the reporter gene is capable of being expressed in the host cell. The phrase "functionally linked" means that when the DNA segments are joined, upon appropriate activation, the reporter gene (.e.g., CAT or luciferase) will be expressed. This expression occurs as the result of the fact that the "ligand responsive promoter" (which is downstream from the hormone response element, and "activated" when the HRE binds to an appropriate ligand-/receptor protein complex, and which, in turn then "controls" transcription of the reporter gene) was "turned on" or otherwise activated as a result of the binding of a ligand-/receptor protein complex to the hormone response element.

As used herein, the phrase "DNA-binding domain" of receptors refers to those portions of the receptor proteins (such as glucocorticoid receptor, thyroid receptor, mineralo-corticoid receptor, estrogen-related receptor and retinoic acid receptor) that bind to HRE sites on the chromatin DNA. The boundaries for these DNA-binding domains have been identified and characterized for the steroid hormone super-family. See FIG. 8; also see Giguere et al. (1986); Hollenberg et al. (1987); Green and Chambon (1987); and Miesfield et al. (1987), Evans (1988).

The present transcription factor is believed to play a regulatory role in the formation of lipid carrying proteins such as Apo CIII, as well as possible effects on Apo A1, Apo B, pyruvate kinase, $\alpha$1 antitrypsin and glutamine synthetase. The cDNA sequence has been identified, and the invention relates to the DNA sequence, recombinant molecules based thereon, probes, sense and antisense RNA, and appropriately transformed host cells. Diagnostic and therapeutic applications are likewise contemplated. of particular interest herein is the APF1 receptor and its gene, since these structures are useful for assessing the activity of drugs.

Numerous epidemiological studies have shown that altered plasma lipoprotein levels are associated with coronary heart disease risk. Elevated low-density lipoprotein (LDL) levels and decreased high-density lipoprotein (HDL) levels are associated with increased coronary heart disease. Studies conducted in many laboratories over the last 30 years have defined a rather complex set of events that determine plasma lipoprotein levels.

Apolipoprotein CIII is a constituent of VLDL and HDL and comprises ~50% of VLDL protein and 2% of HDL protein. Human plasma apoCIII concentrations are in the range of 0.12–0.14 mg/ml. ApoCIII is a glycoprotein containing 1 mol each of galactose, galactosamine, and either 0, 1, or 2 mol of sialic acid. The three resultant isoproteins recognizable by isoelectric focusing are designated CIII-0, CIII-1, and CIII-2 and comprise 14, 59, and 27% of plasma apo CIII, respectively. In vitro apocIII has been shown to inhibit the activities of both lipoprotein lipase and hepatic lipase. ApoCIII has also been shown to decrease the uptake of lymph chylomicrons by the perfused rat liver. These in vitro studies suggest that apo CIII might delay catabolism of triglyceride-rich lipoproteins. Recently, hypertriglyceridemic subjects were shown to have circulation lipoprotein and nonlipoprotein inhibitors of lipoprotein lipase. The lipoprotein-associated inhibition correlated best with apo CIII concentration. In the same study, apoCIII was shown to be a noncompetitive inhibitor of the activity of partially purified lipoprotein lipase. In addition, patients with combined apo A-I and apoCIII deficiency were shown to have low plasma triglyceride levels, and in vivo studies showed that they rapidly convert VLDL to LDL. In vitro lipolysis of their VLDL was inhibited by added apoCIII. Thus, it appears that primary abnormalities in the quantity or quality of apoCIII may effect plasma triglyceride levels, and the physiological role of apoCIII may be in the regulation of the catabolism of triglyceride-rich lipoproteins. Functional domains of apoCIII have been demonstrated. The COOH-terminal 39 amino acids bind phospholipid, whereas the $NH_2$-terminal 40 amino acids do not. Synthesis of apoCIII is mainly in liver and to a lesser degree in intestine.

It is apparent that there is a wide variety of medical uses for agonists and antagonists of HNF-4 and apoCIII. For example, diseases involving the cardiovascular system, such as atherosclerotic heart disease, hyperlipidemia and arteriosclerosis can be treated by interfering with the deposition of VLDL and cholesterol in the vessels.

Similarly, liver disease involving the presence of excessive lipid levels can be treated.

Other disease conditions in which the ligands to HNF-4 and agonists/antagonists to apoCIII will be apparent to those skilled in the medical arts, using such compounds in art-recognized doses.

Likewise, conditions such as obesity may be treated in this manner.

Ligands to HNF-4 may be evaluated which have pharmaceutical properties. One assay format which can be used which employs two genetic constructs. One is typically a plasmid that continuously expresses the receptor of interest when transfected into an appropriate cell line. CV-1 cells are most often used. The second is a plasmid which expresses a reporter, e.g., luciferase under control of a receptor/ligand complex. For example, if a compound which acts as a ligand for HNF-4 is to be evaluated, one of the plasmids would be a construct that results in expression of the HNF-4 receptor in an appropriate cell line, e.g., the CV-1 cells. The second would possess a promoter linked to the luciferase gene in which an HNF-4 response element is inserted. If the compound to be tested is an agonist for the HNF-4 receptor, the ligand will complex with the receptor and the resulting complex binds the response element and initiates transcription of the luciferase gene. In time the cells are lysed and a substrate for luciferase added. The resulting chemiluminescence is measured photometrically. Dose response curves are obtained and can be compared to the activity of known ligands.

Other reporters than luciferase can be used including CAT and other enzymes.

Viral constructs can be used to introduce the gene for the receptor and the reporter. The usual viral vector is an adenovirus. For further details concerning this preferred assay, see U.S. Pat. No. 4,981,784 issued Jan. 1, 1991 hereby incorporated by reference, and Evans et al., WO88/03168 published on May 5, 1988, also incorporated by reference.

HNF-4 antagonists can be identified using this same basic "agonist" assay. A fixed amount of an antagonist is added to the cells with varying amounts of test compound to generate a dose response curve. If the compound is an antagonist, expression of luciferase is suppressed.

The APF1 gene can also be incorporated into the assay described above. Agonist ligands can be screened by the continuous expression of receptors, and by evaluating ligand binding to the receptors, and thereafter quantitating the production of the reporter.

Genes for chimeric receptors can be used in the assay system. These chimeric receptors have hybrid functional characteristics based on the "origin" of the "parental" DNA-binding and ligand-binding domains incorporated within the chimeras. For example, if the DNA-binding domain in the chimeric receptor is a retinoic acid receptor DNA-binding domain (i.e., is obtained from wild-type retinoic acid receptor or is a mutant that contains the functional elements of retinoic acid DNA-binding domain), then the chimera will have DNA-binding properties characteristic of a retinoic acid receptor. The same is true of the ligand-binding domain. If the ligand-binding domain in the chimeric receptor binds to thyroid hormone, then the chimera will have ligand-binding properties characteristic of a thyroid hormone receptor. Most often this is done for a so-called orphan receptor, i.e., one where the natural ligand is unknown. The chimerics usually constructed are ones in which the ligand binding domain of a gene for a known receptor, for example, a glucocorticoid receptor, is replaced by the ligand binding domain of the orphan. The resulting construct generates a receptor with the ligand binding domain of the orphan and the DNA binding domain of the glucocorticoid receptor. Thus, the receptor can be used to control a glucocorticoid controlled gene. Ligands to the orphan are thereby screened in an otherwise well developed system. The HNF-4 gene can be used-in this manner.

Genes for the receptors in expression systems can also be employed which are capable of producing large amounts of a receptor which can be purified and used in binding assays.

These assays are done in a competitive format in which the suspect ligand competes for receptor with a quantity of a known, labeled ligand. These assays can be used to confirm that the ligand does bind the receptor, and as further confirmation that the results of the cis/trans assay are not artifacts. The systems used to express large amounts of receptors include virally infected cells in which the gene for the receptor is introduced by a viral construct by infection rather than by plasmid transfection. Adenoviruses are preferred. Also, a yeast based system can be used where the receptor gene is inserted into a plasmid suitable for yeast expression.

The gene for HNF-4 receptors may be inserted, for example, into a viral construct, and the viral vector with HNF-4 receptor genes can be used to overexpress receptors for HNF-4 as well as in the convection form of the assay noted above.

Expression of recombinant DNA molecules according to this invention may involve post-translational modification of a resultant polypeptide by the host cell. For example, in mammalian cells expression might include, among other things, glycosylation, lipidation or phosphorylation of a polypeptide, or cleavage of a signal sequence to produce a mature protein. Accordingly, as used herein, the term HNF-4 encompasses full-length polypeptides and modifications or derivatives thereof, such as glycosylated versions of such polypeptides, mature proteins, polypeptides retaining a signal peptide, truncated polypeptides having comparable biological activity, and the like.

mRNA can be isolated from cells expressing HNF-4, and used to create a cDNA library. Many methods are known for isolating mRNA and for producing cDNA from it. (See, e.g., Gubler and Hoffman, 1983 and Maniatis et al., 1982.)

The CDNA is then inserted into an appropriate vector. The vector pcDM8, described by Brian Seed (Seed, 1987) is representative. This plasmid has several advantages including a high copy number in *E.coli*, a eukaryotic promoter, and high level of expression in transient expression systems such as COS 7 cells. However, several other vector systems are available. (See, e.g., Cate et al., 1986.)

After constructing a cDNA library, the next step is to isolate from it clones containing HNF-4 cDNA sequences. There are currently many ways to isolate cDNA for a differentially expressed mRNA. These 3 include, for example, (1) plus/minus screening with labeled cDNA; (2) production of subtracted cDNA libraries; and (3) screening with subtractive cDNA probes. (Davis, 1986; Sargent, 1987; Davis et al., 1985, Hedrick et al., 1984; and Duguid et al., 1988.)

Different techniques can be used to identify clones that contained cDNA for HNF-4 sequences. In a first method, clones can be tested for expression of HNF-4 activity in an appropriate eukaryotic expression system. One can use a variety of direct expression techniques, including antibody screening of fusion proteins encoded by cDNA cloned in λGTll (Young and Davis, 1983; Young and Davis, 1984); or activity assay of oocyte-conditioned media after injection of mRNA from cloned cDNA, or from plasmid or phage DNA carrying SP6/T7 promoters. Alternatively, one can make libraries in plasmid, phage, and cosmid vectors containing a variety of promoter, selection and replication elements. Animal cells may be transfected with the library for transient or stable expression. Transfection can be accomplished by a variety of methods. For transient expression, investigators have used spheroplast fusion, DEAE dextran, and electroporation. For stable expression they have used calcium phosphate, spheroplast fusion, and electroporation.

Until recently, identification of cloned molecules by direct expression has required sensitive assays and has been restricted to lymphokines. However, cDNA cloning of single-chain cell-surface molecules in efficient transient expression vectors (see, e.g., Seed and Aruffo, 1987 and Seed, 1987), either by antibody "panning" technology (Wysocki and Sato, 1978) or by identification of functional molecules by FACS (Yamasaki et al., 1988), has expanded the range of cloned molecules that one can identify by direct expression.

Genomic DNA sequences, including transcriptional promoters, for HNF-4 can be isolated by screening genes. A human genomic library with $^{32}$P-labeled probes derived from the coding regions of the HNF-4 DNA sequences. This may yield clones that contain portions of the untranscribed and untranslated regions of the HNF-4 gene.

Transcriptional promoters have a number of uses. First, they are useful to construct vectors which can be used to induce expression of HNF-4. Such vectors may be useful, for example, in gene transfer assays, wherein the inducible promoter is positioned so that it drives transcription of a reporter gene such as chloramphenicol acetyltransferase (CAT), beta-galactosidase, luciferase, etc. This construct can then be introduced transiently or in stable form into an appropriate mammalian cell line. Potential inhibitors or stimulators of induction can then be assayed by measuring their effect on induction by any or all of the inducers listed above.

Hybridomas producing monoclonal antibodies which recognize HNF-4 can also be produced.

Investigators are also exploring radioimmunotherapy and immunotoxin therapy. Radioimmunotherapy involves the use of radioimmunoconjugates in which nuclides such as $^{125}$I, $^{90}$Y, $^{186}$Re and the like are bound to antibodies recognizing a particular surface antigen. Immunotoxins are antibodies conjugated with cell toxins, such as Pseudomonas exotoxin and the like. Upon injection, these conjugated antibodies target the toxic agents to cells expressing the antigen. In accordance with this invention, radioactive markers, nuclides and cellular toxins may be conjugated with HNF-4, or antibodies recognizing HNF-4, target cells expressing HNF-4 or ligands thereto.

An alternative method for isolating HNF-4 would employ fluorescent-antibody labeling. In this method, HNF-4 expressing cells are incubated with Moabs (monoclonal antibodies) and then the Moabs are labeled with, e.g., fluorescently tagged anti-mouse antibody. Cells binding the fluorescent antibodies may then be sorted with a fluorescence activated cell sorter (FACS). The DNA from the sorted cells may be used to transform a bacterial host such as E. coli. DNA from the resulting colonies may then be used to transform a bacterial host such as E. coli. DNA from the resulting colonies may then be used to transfect an appropriate cell line, and this procedure may be repeated until a single expressing clone is identified.

An expression library may also be created in E. coli. For example, a λ ZAP® (Stratagene)/HL-60 library may be constructed and used to express the inserted DNA in E. coli. After plating, the plaques can be directly screened with, e.g., radioactively labeled monoclonals (Young and Davis, 1983 and Young and Davis, 1984). The plaques to which the monoclonals bind can be picked and the DNA insert isolated from them.

Another method to identify HNF-4 ligands, not based on antibody recognition, is to transfect COS 7 cells with an approrpiate library, that may be subtracted, and then pan them directly into HNF-4 expressing cells. Once again, multiple rounds of panning may be required to enrich the library sufficiently to isolate the pertinent clones.

Another technique for isolating the DNA sequences involves screening a cDNA library with oligonucleotide probes. If sufficient HNF-4 protein is purified, for example by affinity chromatography using immobilized antibody, one may determine a partial amino acid sequence and synthesize oligonucleotide probes that correspond to at least a portion of the gene. These probes may then be used to screen the CDNA library. Alternatively, the oligonucleotides may be used as primers to generate long probes to be used in screening the library for genes.

Several uses for HNF-4 DNA sequences and molecules are contemplated as being part of the present invention. First, one may use HNF-4 to produce monoclonal antibody preparations that are reactive for these molecules. The Moabs may be used diagnostically or in turn as therapeutic agents to inhibit HNF-4 binding.

Second, one may use a soluble form of HNF-4 or fragments thereof as a binding inhibitor. The HNF-4 peptides would bind to the HNF-4 ligands and the HNF-4 ligand would bind to HNF-4 receptors. Both methods would thereby inhibit HNF-4 binding.

To produce recombinant soluble HNF-4 ligand, one could, for example, alter a DNA encoding those molecules to eliminate the transmembrane region. Thus, DNAs for soluble molecules would include all or part of the extracellular domain, perhaps attached to the cytoplasmic domain. This approach has already been validated using soluble CD4, the surface protein on T-cells that binds to the AIDS virus (Fisher et al., 1988). This approach also avoids the problems of antibody therapy, since the polypeptides used would be less likely to induce an immune response.

One problem investigators have encountered with soluble recombinant molecules is a short in vivo plasma half-lie (Capon et al., 1989). Because such molecules are quickly cleared from the system, large doses or frequent injections are necessary to have a therapeutic effect. Therefore, investigators have sought methods to increase the half-life of soluble molecules. A potential solution is to link the soluble molecule to another molecule known to have a longer half-life in the blood stream. Due to their long half life, immunoglobulin molecules are promising candidates. Capon et al. (1989) have described the linking of soluble CD4 to an immunoglobulin molecule using recombinant DNA techniques. In this approach, one replaces the variable region of an immunoglobulin molecule with the soluble protein, forming a protein/immunoglobulin fusion protein.

It is expected that the recombinant soluble immunoglobulin fusion proteins will have greater plasma half-life than the soluble protein alone. Such fusion proteins are preferably produced with recombinant constructs, fusing a DNA sequence encoding the soluble molecule to a DNA sequence encoding the constant domain of an immunoglobulin molecule. The recombinant DNA may then be expressed in an appropriate host cell, preferably an animal cell, to produce the fusion protein.

Immunoglobulin fusion proteins have another advantage. Because immunoglobulin molecules are normally bivalent (i.e., they have two binding sites), an immunoglobulin fusion protein would have two HNF-4s and so, two ligand binding sites. Therefore, one would expect them to have greater affinity or avidity for cells displaying HNF-4 ligands.

Third, one may use molecules binding to HNF-4 receptors (such as anti-HNF-4 antibodies, or markers such as the ligand or fragments of it) to detect the presence of disease. This involves, for example, making a molecule detectable by fluorescence or radioactivity, administering it to a patient and determining where in the body it accumulates. In this way one could also identify the type of disease.

Fourth, if HNF-4 binds to its ligand through a carbohydrate moiety or some other post-translational modification, one could use HNF-4 to identify the carbohydrate on the HNF-4 ligand to which it is bound.

Fifth, one could use HNF-4 as part of a system to screen small molecules for inhibitors. For example, one could create an assay system in which small molecules are tested for the ability to inhibit the interaction between HNF-4 and ligands thereto. Small molecule inhibitors identified in this way would provide drug candidates.

Sixth, one could use these molecules to identify endogenous proteins that inhibit HNF-4.

Seventh, one can generate fusion proteins. It is known that proteins are composed of several structural domains (Simmons et al., 1988). DNA sequences encoding various domains of each protein are fused using, for example, the genetic fusion techniques described for making immunoglobulin fusion proteins. The domains chosen are those having the ability to bind to ligands and HNF-4. Domains binding to known ligands would be preferable. The polypeptides produced on expression of these DNA sequences are useful because they would block adhesion of any cell having a ligand to either the HNF-4 receptor, the ligand or both.

Finally, one could use HNF-4 and HNF-4 ligand DNA sequences to produce nucleic acid molecules that intervene in HNF-4 or HNF-4 ligand expression at the translational level. This approach utilizes antisense nucleic acid and ribozymes to block translation of a specific mRNA, either by masking that mRNA with an antisense nucleic acid or cleaving it with a ribozyme. These methods will also be useful in treating disease conditions.

Antisense nucleic acids are DNA or RNA molecules that are complementary to at least a portion of a specific mRNA molecule. (See Weintraub, 1990; Marcus-Sekura, 1988.) In the cell, they hybridize to that mRNA, forming a double stranded molecule. The cell does not translate an mRNA in this double-stranded form. Therefore, antisense nucleic acids interfere with the expression of mRNA into protein. Oligomers of about fifteen nucleotides and molecules that hybridize to the AUG initiation codon will be particularly efficient, since they are easy to synthesize and are likely to pose fewer problems than larger molecules when introducing them into HNF-4-producing cells. Antisense methods have been used to inhibit the expression of many genes in vitro (Marcus-Sekura, 1988; Hambor et al., 1988).

Ribozymes are RNA molecules possessing the ability to specifically cleave other single stranded RNA molecules in a manner somewhat analogous to DNA restriction endonucleases. Ribozymes were discovered from the observation that certain mRNAs have the ability to excise their own introns. By modifying the nucleotide sequence of these RNAS, researchers have been able to engineer molecules that recognize specific nucleotide sequences in an RNA molecule and cleave it (Cech, 1988.). Because they are sequence-specific, only mRNAs with particular sequences are inactivated.

Investigators have identified two types of ribozymes, Tetrahymena-type and "hammerhead"-type. (Hasselhoff and Gerlach, 1988) Tetrahymena-type ribozymes recognize four-base sequences, while "hammerhead"-type recognize eleven- to eighteen-base sequences. The longer the recognition sequence, the more likely it is to occur exclusively in the target mRNA species. Therefore, hammerhead-type ribozymes are preferable to Tetrahymena-type ribozymes for inactivating a specific mMA species, and eighteen base recognition sequences are preferable to shorter recognition sequences.

The DNA sequences described herein may thus be used to prepare antisense molecules against, and ribozymes that cleave, mRNAs for HNF-4 and HNF-4 ligands.

Antisense molecules and ribozymes may be used in methods to treat disease by introducing into cells molecules that interfere with the expression of HNF-4. Since therapeutic agents can be delivered easily by intravenous injection, hepatocytes are attractive targets for such therapies, provided the antisense molecules or ribozymes can be delivered effectively.

Investigators have suggested two approaches which could be used to deliver these molecules to target cells. The first involves transfecting the target cell with a vector that expresses the anti-HNF-4 antisense nucleic acid or the HNF-4-specific ribozymes as an mRNA molecule (Hambor et al., supra). While this approach is very useful when dealing with cell lines in vitro, it may not be as effective in vivo. A second approach that is more promising for in vivo delivery involves loading liposomes with anti-HNF-4 antisense molecules, HNF-4-specific ribozymes or vectors which express them. These liposomes could also contain monoclonal antibodies to direct the liposome to the site of disease.

Another feature of this invention is the expression of the DNA sequences disclosed herein. As is well known in the art, DNA sequences may be expressed by operatively linking them to an expression control sequence in an appropriate expression vector and employing that expression vector to transform an appropriate unicellular host.

Such operative linking of a DNA sequence of this invention to an expression control sequence, of course, includes, if not already part of the DNA sequence, the provision of an initiation codon, ATG, in the correct reading frame upstream of the DNA sequence.

A wide variety of host/expression vector combinations may be employed in expressing the DNA sequences of this invention. Useful expression vectors, for example, may consist of segments of chromosomal, non-chromosomal and Synthetic DNA sequences. Suitable vectors include derivatives of SV40 and known bacterial plasmids, e.g., E. coli plasmids col El, pCR1, pBR322, pMB9 and their derivatives, plasmids such as RP4; phage DNAS, e.g., the numerous derivatives of phage λ, e.g., NM989, and other-phage DNA, e.g., M13 and Filamentous single stranded phage DNA; yeast plasmids such as the 2 μ plasmid or derivatives thereof; vectors useful in eukaryotic cells, such as vectors useful in insect or mammalian cells; vectors derived from combinations of plasmids and phage DNAS, such as plasmids that have been modified to employ phage DNA or other expression control sequences; and the like.

Any of a wide variety of expression control sequences—sequences that control the expression of a DNA sequence operatively linked to it—may be used in these vectors to express the DNA sequences of this invention. Such useful expression control sequences include, for example, the early and late promoters of SV40 or adenovirus, the lac system, the trp system, the TAC or TRC system, the major operator and promoter regions of phage λ, the. control regions of fd coat protein, the promoter for 3-phosphoglycerate kinase or other glycolytic enzymes, the promoters of acid phosphatase (e.g., Pho5), the promoters of the yeast a-mating factors, and other sequences known to control the expression of genes of prokaryotic or eukaryotic cells or their viruses, and various combinations thereof.

A wide variety of unicellular host cells are also useful in expressing the DNA sequences of this invention. These hosts may include well known eukaryotic and prokaryotic hosts, such as strains of E. coli, Pseudomonas, Bacillus, Streptomyces, fungi such as yeasts, and animal cells, such as CHO, Rl.1, B-W and L-M cells, African Green Monkey kidney cells (e.g., COS 1, COS 7, $BSC_1$, BSC40, and BMT10), insect cells (e.g., Sf9), and human cells and plant cells in tissue culture.

It will be understood that not all vectors, expression control sequences and hosts will function equally well to express the DNA sequences of this invention. Neither will all hosts function equally well with the same expression system. However, one skilled in the art will be able to select the proper vectors, expression control sequences, and hosts without undue experimentation to accomplish the desired expression without departing from the scope of this invention. For example, in selecting a vector, the host must be considered because the vector must function in it. The vector's copy number, the ability to control that copy number, and the expression of any other proteins encoded by the vector, such as antibiotic markers, will also be considered.

In selecting an expression control sequence, a variety of factors will normally be considered. These include, for example, the relative strength of the system, its controllability, and its compatibility with the particular DNA sequence or gene to be expressed, particularly as regards potential secondary structures. Suitable unicellular hosts will be selected by consideration of, e.g., their compatibility with the chosen vector, their secretion characteristics, their ability to fold proteins correctly, and their fermentation requirements, as well as the toxicity to the host of the product encoded by the DNA sequences to be expressed, and the ease of purification of the expression products.

Considering these and other factors a person skilled in the art will be able to construct a variety of vector/expression control.sequence/host combinations that will express the DNA sequences of this invention on fermentation or in large scale animal culture.

Antibodies against HNF-4 and ligands thereto will make possible another method for isolating other ligands. The method takes advantage of an antibody characteristic known as idiotypy. Each antibody contains a unique region that is specific for an antigen. This region is called the idiotype. Antibodies, themselves, contain antigenic determinants; the idiotype of an antibody is an antigenic determinant unique to that molecule. By immunizing an organism with antibodies, one can raise "anti-antibodies" that recognize them, including antibodies that recognize the idiotype. Antibodies that recognize the idiotype of another antibody are called anti-idiotypic antibodies. Some anti-idiotypic antibodies mimic the shape of the original antigen that the antibody recognizes and are said to bear the "internal image" of the antigen (Kennedy, 1986). When the antigen is a ligand, certain anti-idiotypes antibodies that bind to receptors including the receptor for insulin, angiotensin II, adenosine I, β-adrenalin, and rat brain nicotine and opiate receptors (Carlsson and Glad, 1989).

Taking advantage of this phenomenon, other HNF-4 ligands may be isolated using anti-idiotypic antibodies. Anti-idiotypes may be used to screen for molecules binding to the original antigen.

EXPERIMENTAL PROCEDURES

Extract preparation and chromatography were carried out at 4° C.

Preparation of Rat Liver Nuclear Extract

Crude rat liver nuclei extracts were prepared using the method of Gorski et al. (1986) modified as follows: approximately 50 gm of tissue were removed from 3 to 4 freshly sacrificed male rat (Sprague-Dawley, about 20 weeks old), homogenized in 30 ml of buffer A (10 mM HEPES pH 7.9, 25 mM KCl, 0.15 mM spermine, 0.5 mM spermidine, 1.0 mM EGTA, 1.0 mM EDTA, 1 mM dithiothreitol (DTT), 0.32 M sucrose), dounced 5 to 7 times (pestle A) and diluted with two volumes of Buffer b (as A except 2 M sucrose). 27 ml of the homogenate were layered on a 10-ml cushion of Buffer B and centrifuged in a Beckman SW27 rotor at 15 krpm for 45 min. The pelleted nuclei were rinsed once in buffer C (as buffer A except 20% glycerol in place of sucrose), dounced 5 times (pestle B) and brought to 0.41 M KCl with buffer D (as C except 1M KCl). The protein was extracted by gentle rocking at 4° C. for 45 minutes. The chromatin was pelleted by centrifugation at 180,000×g for 45 min. and the supernatant (crude nuclear extract, 3.5–5.0 mg/ml protein) was frozen immediately in liquid $N_2$ and stored at −80° C. DTT and protease inhibitors (phenylmethyl-sulfanyl fluoride, 0.5 mM; benzamidine HCl, 1 mM; leupeptin, 0.5 μg/ml; pepstatin, 1 μg/ml) were added to all buffers just prior to use.

Mobility-shift Assay and Purification of HNF-4

Gel mobility-shift (DNA binding) assays (Fried & Crothers, 1981) were carried out in 15 μl reactions in shift buffer (20 mM HEPES (pH 7.9), 40 mM KCl, 2 mM $MgCl_2$, 1 mM DTT, 0.5 mM EGTA, 4% Ficoll) and contained 1–2 μl protein extract and 0.5 ng double-stranded oligonucleotide probe labeled with $^{32}P$ by Kenow. Reactions were incubated at room temperature for 20 minutes. Poly (dl-dC), oligonucleotide competitor and bovine serum albumin (BSA) were added as indicated. Protein-bound DNA complexes (5 μl of shift reaction) were separated from free probe by electrophoresis on an 8% polyacrylamide gel in 25 mM Tris-borate, 0.25 mM EDTA at 4° C.

Chromatography fractions were assayed by the mobility-shift assay using either the APF-1 or HNF4P oligonucleotide as probe. Crude nuclear extract (up to 300 mg) was applied to a 60 ml heparin agarose (Sigma, Type 1) column equilibrated in buffer E (20 mM HEPES pH 7.9, 10% glycerol, 1 mM DTT, 0.1 mM EDTA, 0.1 Mm EGTA) containing 150 mM KCl. The column was developed with a 400 ml linear gradient from 0.2 to 0.8 M KCl. Fractions with HNF-4 activity (0.50–0.55 M KCl) were pooled, precipitated with ammonium sulfate (300 mg/ml final), dissolved in buffer F (as buffer E but with 0.05% Nonidet P-40 (NP-40)) containing 100 mM NaCl, dialyzed and loaded onto a 240 ml Sephacryl S300 (Pharmacia) column. Active fractions, eluting just after the void volume, were loaded onto a 5 ml double-stranded DNA cellulose (Sigma) column equilibrated in buffer F/100 mM NaCl. The column was developed with a three-step gradient: 150 mM, 300 mM and 1 M NaCl. Active fractions (eluting at 300 mM NaCl) were diluted to 100 mM NaCl and poly (dl-dC) and sonicated, denatured salmon sperm DNA were added to 10 μg/ml each. After 10 minutes on ice, the sample was loaded onto a 2 ml HNF4P oligonucleotide affinity column prepared as in Kadonaga and Tjian (1986) and equilibrated in buffer F/100 mM NaCl. The column was developed with a 20 ml linear gradient from 0.1 to 1.0 M NaCl. Active fractions, eluting at 0.18–0.3 M NaCl, were diluted to 0.1 M NaCl, supplemented with poly (dl-dC) and salmon sperm DNA to 3 µg/ml each. and passed over a 2 ml APF1 oligonucleotide affinity column as described above. The HNF-4 binding activity, eluting at 0.25 to 0.5 M NaCL, was dialyzed against buffer T (as buffer F but with 20 mM Tris HCl pH 8.0 and 20% glycerol) containing 100 mM NaCl and loaded onto a FPLC Mono Q HR 5/5 (Pharmacia) column. The column was developed with a linear gradient from 0.1 to 1.0 M NaCl. The peak fraction in one preparation (fraction 38) eluted at about 0.42 M NaCl. Purified HNF-4 refers to material passed over all five columns.

Renaturation of HNF-4

Approximately 50 ng of purified HNF-4 (based on binding activity to APF1 oligonucleotide) were mixed with SDS sample buffer, heated for 15 min. at 72° C. and fractionated on a 12.5 cm 10% SDS-polyacrylamide gel (Laemmli, 1970) pre-run with 0.1 mM sodium thioglycolate. Gel slices were cut out and the protein was eluted and renatured essentially as described by Briggs et al. (1986) except that 0.1 mg/ml BSA was added to the elution buffer and buffer G (as buffer E but with 0.1% NP-40) containing 100 mM NaCl and 3.5 mM $MgCl_2$ and 6M guanidine-HCl were used for renaturation. 5 µl of 35 µl recovered material was used in the mobility shift assay (0.05 µg poly (dl-dC).

DNA Footprinting Phosphatase and Protease Studies

A 137-bp DNA fragment containing −202 to −70 of the mouse TTR promoter (see Costa et al., 1986) was labeled with $^{32}$p by filling in with Klenow either at a BamH 1 site (7 bp from −202) or at an Xba 1 site (−70). Purified HNF-4 (enough to shift 2 ng of APF1 oligonucleotide) was incubated in a 30 µl shift reaction with 10 ng of the −202/−70 TTR probe in the absence of poly dl-dC and electrophoresed on a 5% polyacrylamide gel. After treating the gel with 1,10-phenanthroline copper ion as described in Kuwabara and Sigman (1987), the bound and free probes (identified by autoradiography of the wet gel) were cut out, embedded in agarose and the DNA was recovered by electroelution onto DEAE membrane (NA-45 (Schleicher & Schuell)). The cleaved probes were analyzed on an 8 M urea/10% polyacrylamide gel.

For the phosphatase reaction, purified HNF-4 (MonoQ fxn 38, 4 ng) was incubated for 20 min. at 37° C. in a 20 µl, reaction either with or without calf intestine alkaline phosphatase (CIP, 2.5 µl at 1U/µl Boehringer Mannheim) in 0.25×shift buffer lacking KCl and EGTA but containing 0.005% NP-40 and 0.25 µg/ul BSA. The reaction without enzyme contained 2.5 µl of the CIP storage buffer (30 mM triethanolamine pH 7.6, 3 M NaCl, 1 mM $MgCl_2$, 0.1 mM $ZnCl_2$). For the protease reactions, purified HNF-4 (fxn 38, 62.5 ng) was incubated for 1.5 hours at 37° C. in a 10 µl reaction with Protase V8 (5 ng) or Endoproteinase LysC (5 ng) (both from Boehringer Mannheim) in 0.5×butter T containing 100 mM NaCl. One-fifth of each reaction was tested in the mobility-shift assay (BSA at 3 µg/15 µl reaction, no poly (dl-dC) with each of four $^{32}$P-labeled oligonucleotide probes (APF1, −151 to −130, HNF4P, HNF4D).

Cyanogen Bromide Cleavage and Protein Sequencing

Approximately 10 µg (200 pmoles) of purified HNF-4 (fxn 38) was brought to 1.3 M guanidine HCL (ultra pure, ICN) and 0.03% β-mercaptoethanol (Sigma) and loaded onto a reverse-phase HPLC column (Aquaporebutyl 30×2.1 mm, 7 µm, Brownlee labs) equilibrated in buffer H (5% 1-propanol in 10 mM trifluoroacetic acid, TFA). The column was developed with a 9 ml-gradient from 5% to 59% 1-propanol in 10 mM TFA at a flow rate of 0.15 ml/min. Fractions containing HNF-4 (47% to 50% propanol) were pooled, dried, and treated with 5 µg/ml CNBr in 50% formic acid for 24 hours. The CNBr-generated peptides were separated by HPLC using the conditions given above. Fractions containing peptides were either sequenced directly on an Applied Biosystems gas phase (Model 470) sequenator (pep 1, pep 2 and pep 5) or further purified on a 16.5% SDS polyacrylamide gel and processed for sequencing as in Matsudaira (1987) (pep 3 and pep 4).

Isolation of HNF-4 cDNA Clones

Oligonucleotide primers corresponding to the least degenerate regions of pep 1, pep 2 and pep 3 were synthesized: Primer 1S (from sense direction of pep 1) was 5'CC(C/A)tcc(C/G)AXGGNGCNAAYYTNAA-3'(SEQ ID NO:2) where N=A+G+T+C, X=A+G,Y=C+T. Primer 1A (antisense of pep 1) was 5'-TTAggTTNGCNCCYT (G/C)N (G/C)XNGG-3'(SEQ ID NO:3). Primer 2S (sense of pep 2) was 5'-CATCTAGAATtGAgCAgAT(Y/A)CA(G/A)TTY-AT(Y/A)AA-3'(SEQ ID NO:4). Primer 2A (antisense of pep 2) was 5'AACGTCAGAgcTT(X/T)AT(G/A)AAYTG-(X/T)ATYTGYTC-3'(SEQ ID NO:5). Primer 3S (sense of pep 3) was 5'-GAgGCtGTNCAXAAYGAX(C/A)GNGA-3' (SEQ ID NO:6). Primer 3A (antisense of pep 3) was 5'-TC(Y/G)C(G/T)cTCXTTYTGNACNGCYTC-(SEQ ID NO:7). Lower case letters indicate codon usage according to Lathe (1985); underlined regions indicate an Xho 1 restriction site used for subcloning. The primers were used in the polymerase chain reaction (PCR) (Saiki et al., 1988) in pairwise combinations (Primer 1S+2A, 1S+3A, etc.) following the protocol by Perkin-Elmer Cetus. 50 µl reactions containing 0.5 to 4 µg of each primer (1S and 1A, 4 µg; 2S and 2A, 0.5 µg; 3S, 1 µg; 3A, 1.5 µg) and 10 µl of rat liver cDNA library in λ Zap II (from Strategene, $1.5×10^6$ independent recombinants, amplified and used at $4×10^{10}$ pfu/ml) underwent 30 cycles in a DNA Thermal Cycler (Perkin Elmer Cetus). Each cycle consisted of 1 min. at 94° C., 1 min. at 57° C., 2.5 min. (plus 5 sec/cycle) at 72° C. PCR products were cloned into the polylinker region of Bluescript KS(+) (Stratagene) and sequenced using the Sequenase kit from U.S. Biochemicals. dITP reactions were performed on regions where the sequence was ambiguous.

The nonamplified rat liver cDNA library (Stratogene) was screened for full length clones as described in Maniatis et al. (1982) except: the nitrocellulose filters were autoclaved to bind the DNA; no formamide was used in the prehybridization buffer; and hybridization and washings were done at 50° C. The probe was the subcloned PCR product obtained with Primers 3S and 2A labeled with $^{32}$p by random priming (Feinberg & Vogelstein, 1983).

Transactivation Assay

The HIV-CAT reporter construct (~5 kb) contained −57 to +80 of the human immunodeficiency virus (HIV) long terminal repeat (LTR) (Rosen et al., 1985) immediately 5' to the bacterial chloramphenicol acetyl transferase (CAT) gene linked to the SV40 splice and poly(a) sites (from pSV2 CAT, Gorman et al., 1982) in pGEM-1 (Promega) (construction described in Lew, Decker, Stehlow, Darnell, in preparation). The APF1-HIV-CAT reporter construct consisted of two APF1 oligonucleotides in direct repeat cloned into the Sma 1 site of the pGEM polylinker (17 bp form the HIV LTR) of HIV-CAT. The HNF-4 expression vectors (sense, pLEN4S, and antisense, pLEN4A) were constructed by cloning the entire 3 kb HNF-4 cDNA of pf7 into the BamH 1 site of pLEN (courtesy of Cal-Bio Inc.) pLEN is a ~5 kb expression vector containing the SV40 enhancer (1120-bp, Hind III fragment), the human metallothionein promoter (836-bp, Hind III-BamH1 fragment) and human growth hormone 3' untranslated region (~550-bp, BamH I-EcoR I (fragment) in pUC8.

DNA transfections and β-galactosidase and CAT assays were performed essentially as in Sambrook et al. (1989). DNA was transfected into HeLa cells, grown in Dulbecco's-Modified Eagle's medium (DMEM, Gibco) plus 10% bovine calf serum (BCS, Hyclone), using the calcium phosphate method. A precipitate of HNF-4 expression vector (pLEN4S or PLEN4A, 0 to 5 μg), 1 μg pCMV-β(gal) (internal control, MacGregor & Caskey, 1989), 2 μg reporter construct (HIV-CAT or APF1-HIV-CAT) and 50 μg denatured sonicated salmon sperm DNA were added to cells 60–80% confluent in a 100-mm dish. After 15 hours. at 37° C., the cells were treated with a glycerol shock (15%) and incubated for 48 hours at 37° C. in DMEM plus 10% BCS and 10 mM sodium butyrate (to enhance expression from the SV40 enhancer, Gorman et al., 1983). Extracts were prepared, normalized to β-galactosidase activity and assayed for CAT activity (20-hr. incubation at 37° C.).

Northern Blot Analysis

Total RNA was extracted from male rat (Sprague-Dawley) tissue using the acid phenol method of Chomezynski and Sacchi (1987) as modified by Puissant and Houdebine (1990). Poly A+ RNA was selected on oligo-dT cellulose columns and electrophoresed (5 μg/lane) in a 1% agarose formaldehyde gel as described in Sambrook et al. (1989). The RNA was transferred to Immobilon-N (Millipore) and probed according to the protocol provided by the manufacturer. HNF-4 mRNA was detected with a random-primed cDNA fragment containing nucleotides 616 to 1114 (the hatched area in FIG. 3, top). The high stringency wash was with 0.2×SSC, 0.1% SDS at 600° C. for 15 minutes. The autoradiograph with the HNF-4 probe was exposed for 3 days with two intensifying screens. Ribosomal RNA (28S and 18S, 4.9 and 1.9 kb, respectively) was used as size markers.

Table 1

The sequence and origin of the top strand of the oligonucleotides used are given. The underlined nucleotides were added for convenience. Complementary bottom strands had four-base overhands at their 5' ends. The bold type highlights the region of consensus and shows matches in the hormone response elements. ERE is from the Xenopous vitellogenin $A_2$ (Klein-Hitpaβ et al., 1986), TRE and GRE are palindromic variants of the response elements in the rat growth hormone (Glass et al., 1988) and tyrosine aminotransferase (Strahle et al., 1987) genes, respectively. Arrows indicate conserved palindromic regions.

TABLE 1

Oligonucleotides Used in This study

| | Gene | Sequence | Position | |
|---|---|---|---|---|
| -151 to -130 | TTR | 5'-<u>TCGA</u>GGCAAGGTTCATATTTGTGTAG-3' | (SEQ ID NO:9) | -151 to -130 (mouse) |
| HNF4P | TTR | 5'-<u>TCGA</u>CCCTAGGCAAGGTTCATATGGCC-3' | (SEQ ID NO:10) | -156 to -138 (mouse) |
| HNF4D | TTR | 5'-<u>TCGA</u>CTCTCTGCAAGGGTCATCAGTAC-3' | (SEQ ID NO:11) | -1.86 kb (mouse) |
| APF1 | apoCIII | 5'-<u>TCGA</u>GCGCTGGGCAAAGGTCACCTGC-3' | (SEQ ID NO:12) | -66 to -87 (human) |
| LF-A1 | a1-AT | 5'-<u>ACGA</u>AACAGGGGCTAAGTCCACTGGCTG-3' | (SEQ ID NO:13) | -101 to -128 (human) |
| HNF-4 Consesus | | GGCAAAGGTCAT | (SEQ ID NO:14) | |
| | | T  T G TC  C | (SEQ ID NO:14) | |
| Hormone Response Elements | | | | |
| ERE (estrogen) | | 5'-<u>AGCT</u>CTCAGGTCACTGTGACCTGA-3' | (SEQ ID NO:15) | |
| TRE (thyroid) | | 5'-<u>AGCT</u>CTCAGGTCATGACCTGA-3' | (SEQ ID NO:16) | |
| GRE (glucocorticoid) | | 5'-<u>AGCT</u>CTCAGAACACTGTGTTCTGA-3' | (SEQ ID NO:17) | |

RESULTS

Purification and Characterization of HNF-4Protein

Table 1 lists the different oligonucleotides used in the purification and characterization of the HNF-4 binding protein. Oligonucleotide -151 to -130 contains the HNF-4 site (-151 to -140) required for TTR expression in transfection assays as well as a weak HNF-3 site (-130 to -140) (Costa et al., 1989); HNF4P is similar to -151 to -130 but does not contain the HNF-3 site; HNF4D is from a distal site in the TTR promoter (approximately -1.9 kb) which was shown to enhance the transcription of TTR marginally (Costa et al., 1988; 1989) and which is bound less well by protein in crude liver extracts than HNF4P. APF1 and LF-A1 are oligonucleotides derived from the promoter regions of the human apolipoprotein CIII (apoCIII) and α1-antitrypsin (α1-AT) genes, respectively. Cross competition studies done previously (Costa et al., 1990) showed that the factor that binds to the HNF-4 site in the TTR promoter also binds to APF1.

HNF-4 binding protein was purified from rat liver nuclear extract by six chromatography steps including sequence-specific DNA affinity columns made with either multimeric HNF4P or APF1 oligonucleotides. Each step was assayed by the mobility-shift assay using a double-stranded probe (HNF4P or APF1). An SDS gel of the starting material of the last five columns plus the final purified fraction (Fxn 38, FIG. 1A) showed a single Coomassie-stained band of 54 kD nominal molecular weight that co-purified with the mobility-shift activity. In one preparation, approximately 700 mg nuclear protein from 41 rats yielded 30–40 $\mu$g of the 54 kD protein with an overall recovery of 10–15% based on the mobility-shift activity. By comparing protein concentration and DNA-binding activity (APF1 probe) for each step of the purification, the cumulative gain in specific activity was estimated to be 5000 to 10,000-fold.

To show that the 54 kD species was the HNF-4 binding protein, the purified material was subjected to preparative SDS-PAGE, the gel was cut into slices and the proteins were eluted from each slice, renatured and assayed for HNF-4 binding activity. One such renaturation experiment in which only the 45 to 65 kD region was assayed showed that the major band migrating at 54 kD (primarily slice 3) contained HNF-4 binding activity (FIG. 1B). Other experiments (not shown) verified that the regions below 45 kD and above 65 kD did not contain binding activity.

Figure 1A:
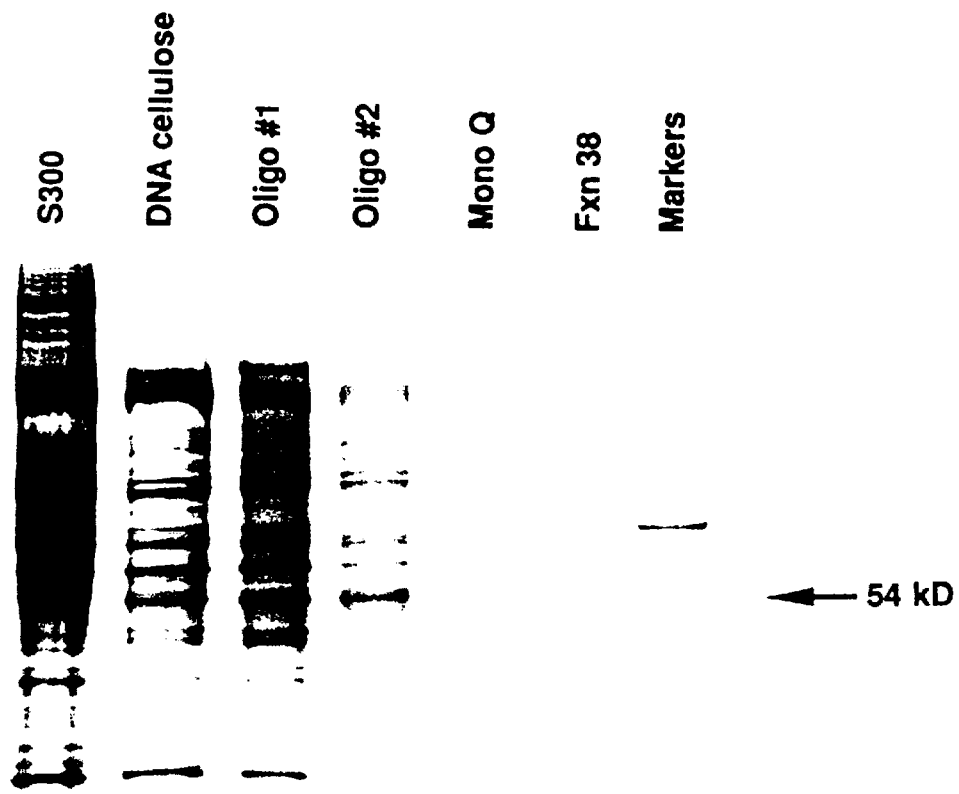
FIG. 1—Purification and Identification of HNF-4
Figure 1B:
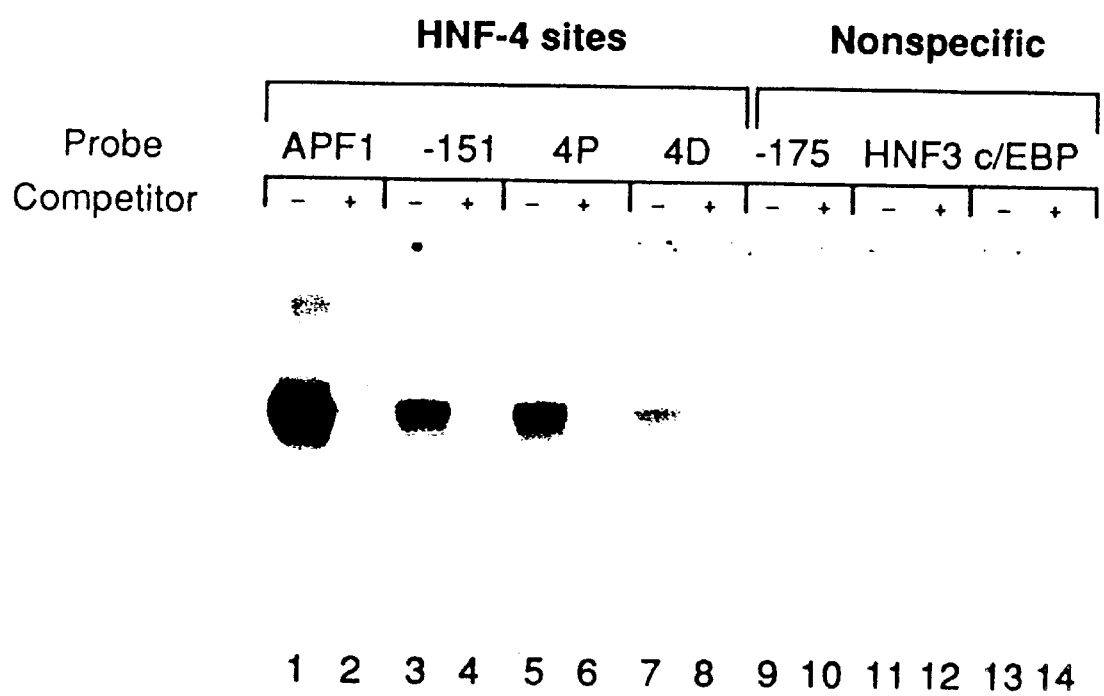

The affinity column containing the apoCIII site, APF1 (oligo #2, FIG. 1A) was used in the purification scheme after the column with the TTR site, HNF4P (oligo #1, FIG. 1A). Therefore, to be certain that the final purified material still bound the TTR site, four different probes containing slightly different HNF-4 sites (APF-1, −151 to −130, HNF4P, HNF4D) and three probes lacking sequence similarity to the HNF-4 recognition site (−175 to −151, HNF3 and C/EBP) were labeled to the same specific activity and tested in the mobility-shift assay with the purified protein. The purified material bound to all four HNF-4 sites and product identical shift bands (FIG. 1B). The different relative affinities of the purified material for the various probes (APF1>−151 to −130=HNF4P>HNF4D) is the same as that found in crude liver nuclear extracts (not shown). As expected, the purified material did not bind to any of the unrelated oligonucleotides (FIG. 1B, lanes 9–14).

Figure 2A:
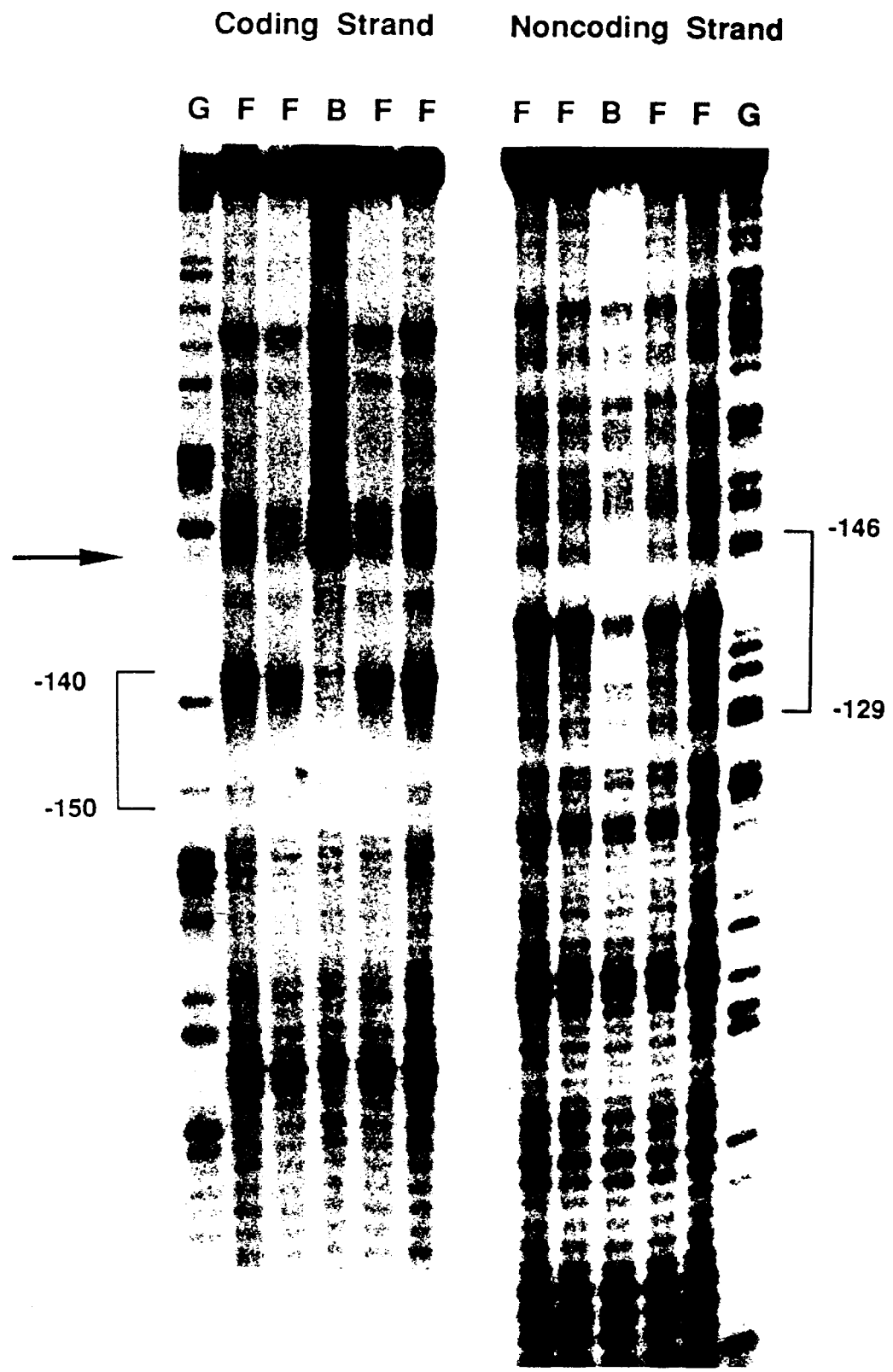

To verify that the protein we purified was the one originally described by Costa et al. (1989), the purified protein was shown to protect the region from −140 to −150 of the coding strand in the TTR promoter from cleavage by copper phenanthroline (FIG. 2A). This is the same region originally defined as the HNF-4 site by transient transfection assays with deletion mutants and by methylation interference experiments with crude liver extracts (Costa et al., 1989).

Figure 1C:
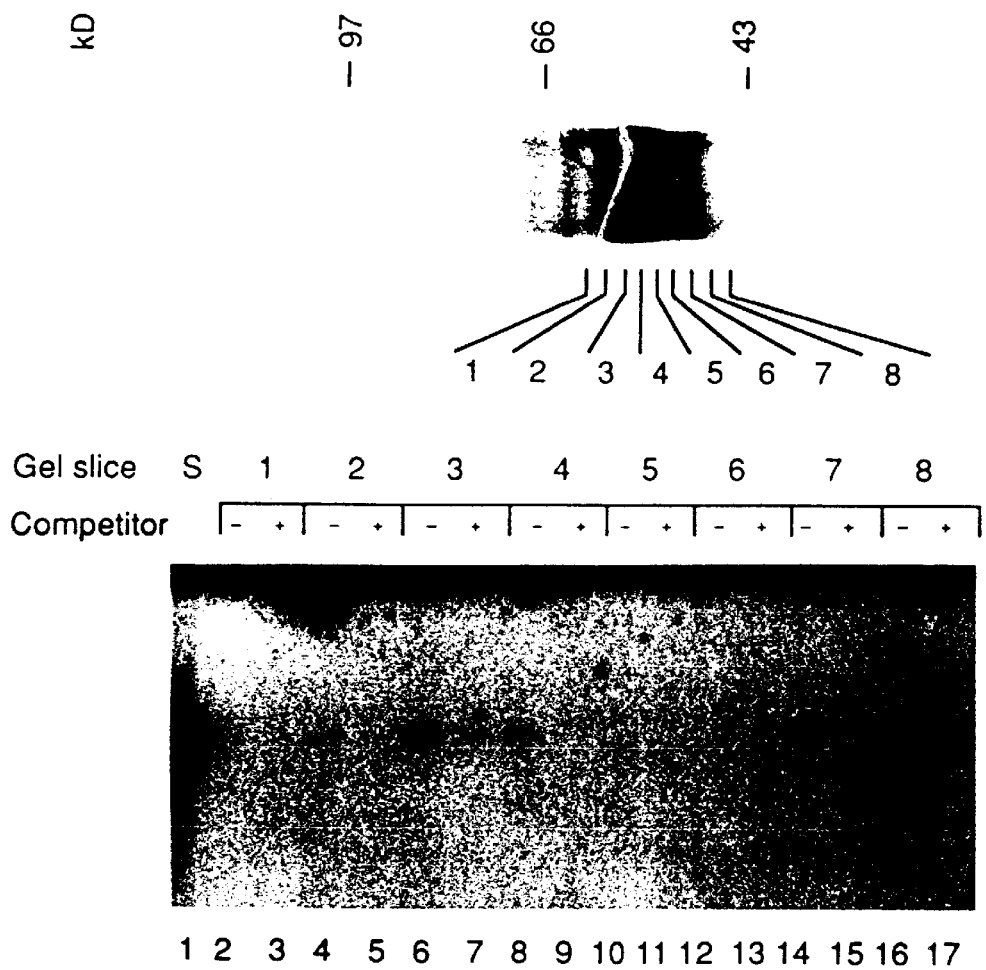
Figure 2B:
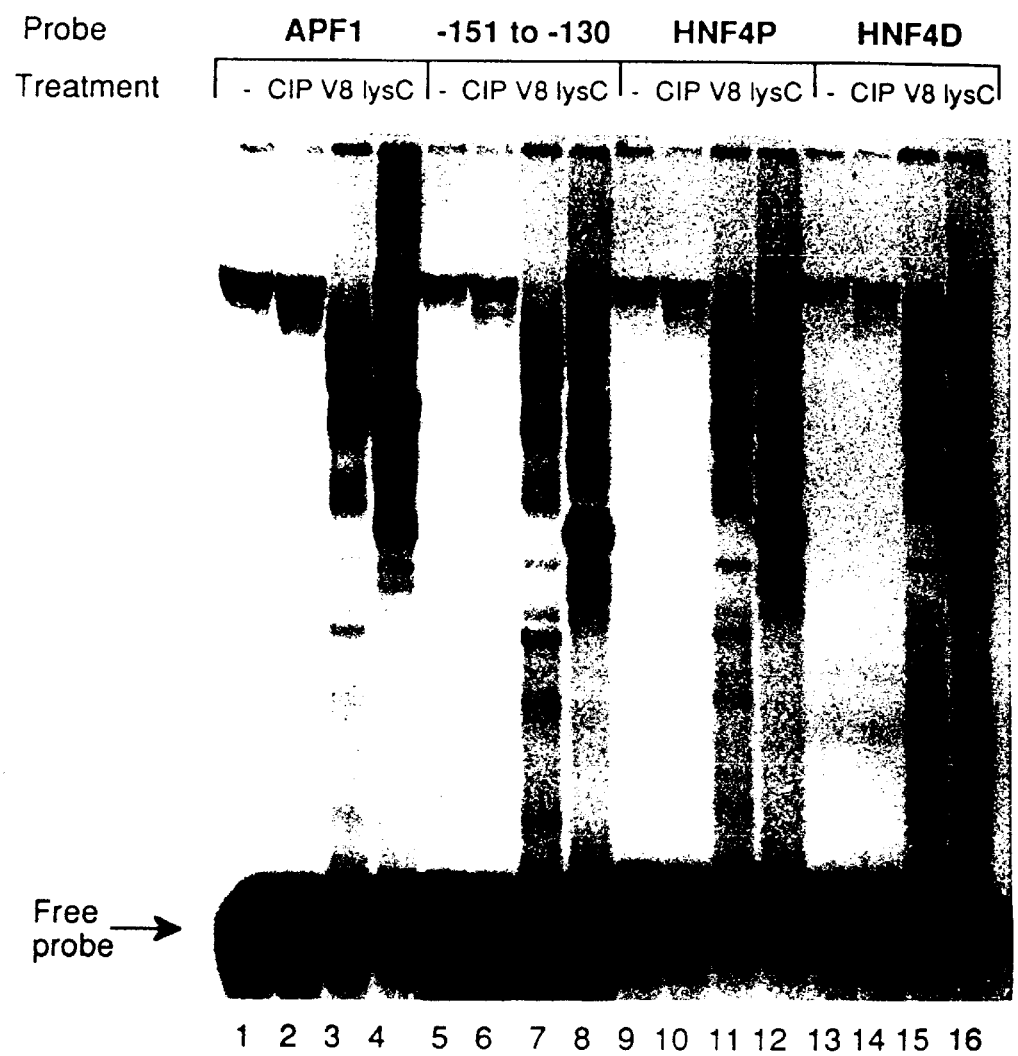

The appearance of minor bands migrating slightly faster than the major band at 54 kD in some silver-stained SDS gels (evident as a broad band in FIG. 1C) and the fact that the purified material bound several somewhat different probes raised the concern that there might be more than one DNA binding protein present in the purified material. To examine this possibility, Mono Q fraction 38 was treated with a modifying reagent (phosphatase or one of several proteases), divided into aliquots and subjected to the mobility-shift assay using the four HNF-4 probes described above. The results, displayed in FIG. 2B, show that a given treatment (calf intestine alkaline phosphatase (CIP), Protease V8 (V8), Endoproteinase Lys-C (lysC)) created essentially the same pattern of shifted bands regardless of the probe used. Had the purified material contained a mixture of different polypeptides, different peptide fragments, and therefore different shift bands, should have resulted. Therefore, we concluded that there was a single polypeptide in the purified material that bound to the various probes.

Isolation of HNF-4 cDNA Clones

In order to isolate the cDNA encoding HNF-4 protein, a partial amino acid sequence of the protein purified from the rat liver was obtained. Since the intact protein was found to be N-terminally blocked, the purified material (Mono, fxn 38; 10 $\mu$g) was subjected to reverse-phase high pressure liquid chromatography (HPLC) and the major peak, containing the 54 kD protein, was cleaved with cyanogen bromide. The resulting peptides were separated by HPLC and sequenced.

Five peptide sequences were obtained (pep 1–5). Sense (S) and antisense (A) primers 23 nucleotides long with degeneracies ranging from 36 to 4096 were made to three of the peptides (pep 1, pep 2, pep 3). The primers were used in pairwise combinations (primers 1S and 2A, 1A and 2S, etc.) in a polymerase chain reaction (PCR) with an amplified rat liver cDNA library a the template. Only the combinations of primers 1S and 2A and primers 3S and 2A resulted in products easily discernible by ethidiumbromide staining of an agarose gel (1.0 and 0.5 kilobase, kb, respectively). After subcloning and sequencing, the large product (1S+2A) was found to contain the smaller product (3S+2A) (FIG. 3, top). The deduced amino acid sequence from the large product also contained a region very similar to the two zinc fingers found in steroid hormone receptors. The shorter PCR product, which did not contain the zinc fingers, was used to screen 3.6×10$^5$ primary recombinants in the rat liver library. Of 22 positive clones at the second round of screening, nine were fully characterized and found to be overlapping.

The partial nucleotide sequence of the largest cDNA insert (pf7, FIG. 3 bottom) contains a long open reading frame of 1365 base pairs (bp) starting with an initiator methionine at nucleotide 59. There is another in-frame ATG codon beginning at nucleotide 32 but comparison with the consensus sequence for translation initiation (GCC A/G CCATGG, Kozak, 1987) and SDS-PAGE analysis of in vitro translation products (not shown) suggest that the ATG codon at nucleotide 59 is the major initiator for translation. All five peptide sequences derived from the purified HNF-4 protein appeared in the predicted amino acid sequence (FIG. 3 bottom) confirming that the purified HNF-4 preparation did indeed contain only one major polypeptide. The 1365-bp open reading frame encodes a protein 455 amino acids long with molecular weight of 50.6 kD. The polyadenylation signal was not found.

A search of GenBank revealed that HNF-4 is a novel protein but that it has a structure analogous to that of the steroid/thyroid hormone receptors (see FIG. 4). HNF-4 contains a region with two potential zinc fingers between amino acids 50 and 116 which is 40 to 63% identical to the zinc finger (DNA binding) domain of other members of the steroid receptor superfamily. The proposed regulatory protein for the mouse major histocompatibility class I proteins (H-2RIIBP (Hamada et al., 1989) had the greatest similarity (62.7% identity) and the human thyroid hormone receptor (c-erbA; $T_3T_\beta$) (Weinberger et al., 1986) was the second most similar (59.7% identity) in this region. While the zinc finger domain of HNF-4 is flanked by regions with no similarity to any known protein, there is a large hydrophobic region in the C-terminal half of the protein (amino acids 133 to 373) which has definite similarity to the ligand binding domain of some of the other receptors (20–37% identity). Again, HNF-4 is most similar to H-2RIIBP (37.3% identity) but as with H-2RIIBP, it is not known if HNF-4 requires a ligand let alone what the ligand might be.

The HNF-4 protein has two other distinctive features: a proline-rich region (23%) at the C-terminus (amino acids 400–477) which could be an activator domain (Mermod et al., 1989) and three serine/threonine-rich regions (30–38%) scattered throughout the molecule (amino acids 15 to 44, 129 to 161, and 398 to 426) which could be sites for phosphorylation (Krebs et al., 1988). Whether or not HNF-4 is modified has not been established yet, but the possibility of some post translational modification is suggested by the somewhat aberrant mobility of the protein isolated from rat liver in the SDS gel (54 kD versus 50.6 kD predicted from amino acid sequence) as well as the appearance of minor bands migrating slightly faster than the major band in SDS gels.

In vitro Expression of HNF-4 DNA

Figure 5A:
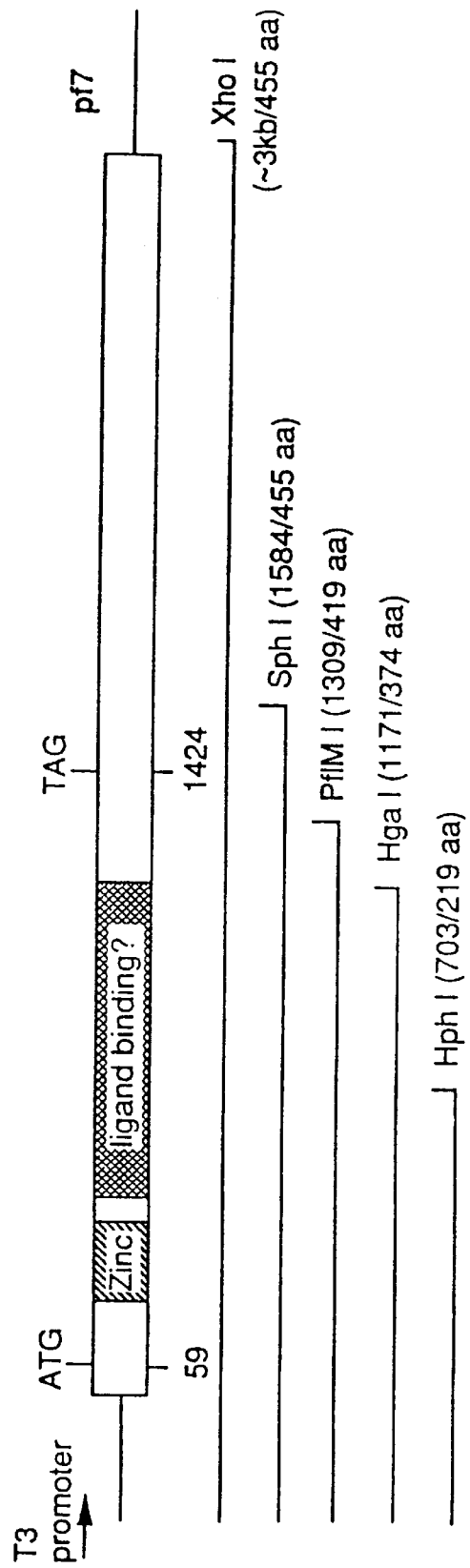
Figure 5B:
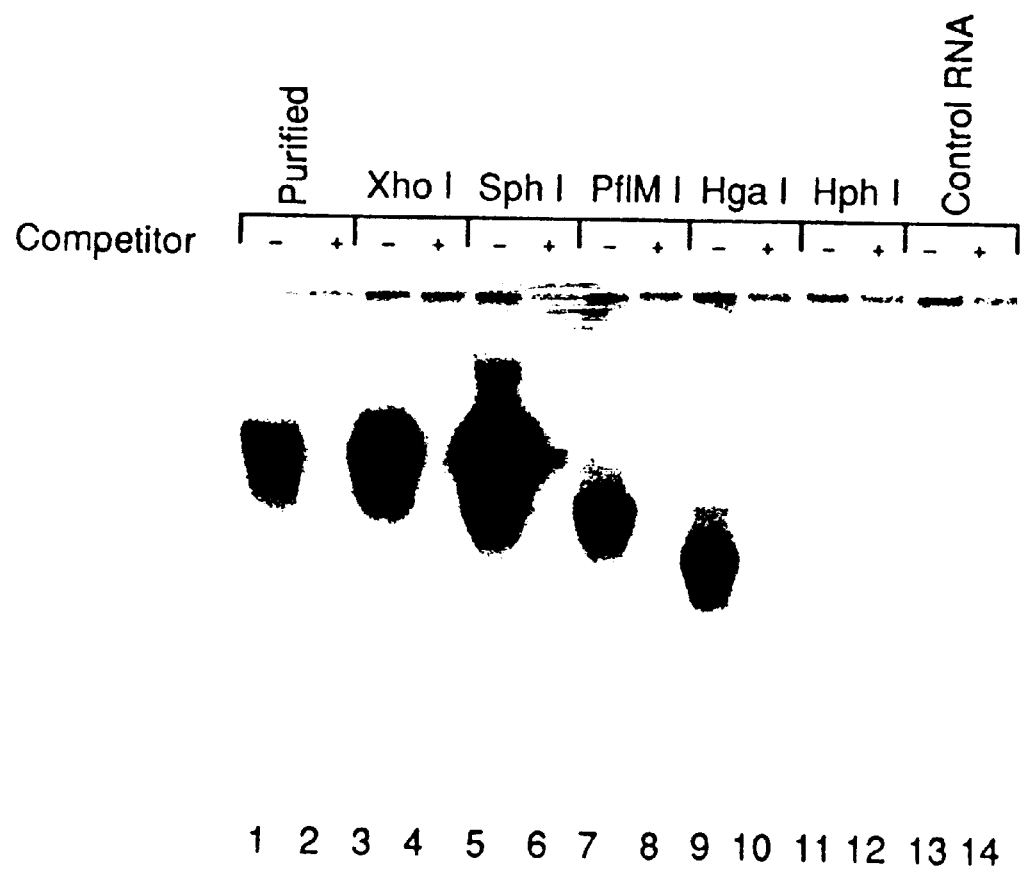
Figure 5C:
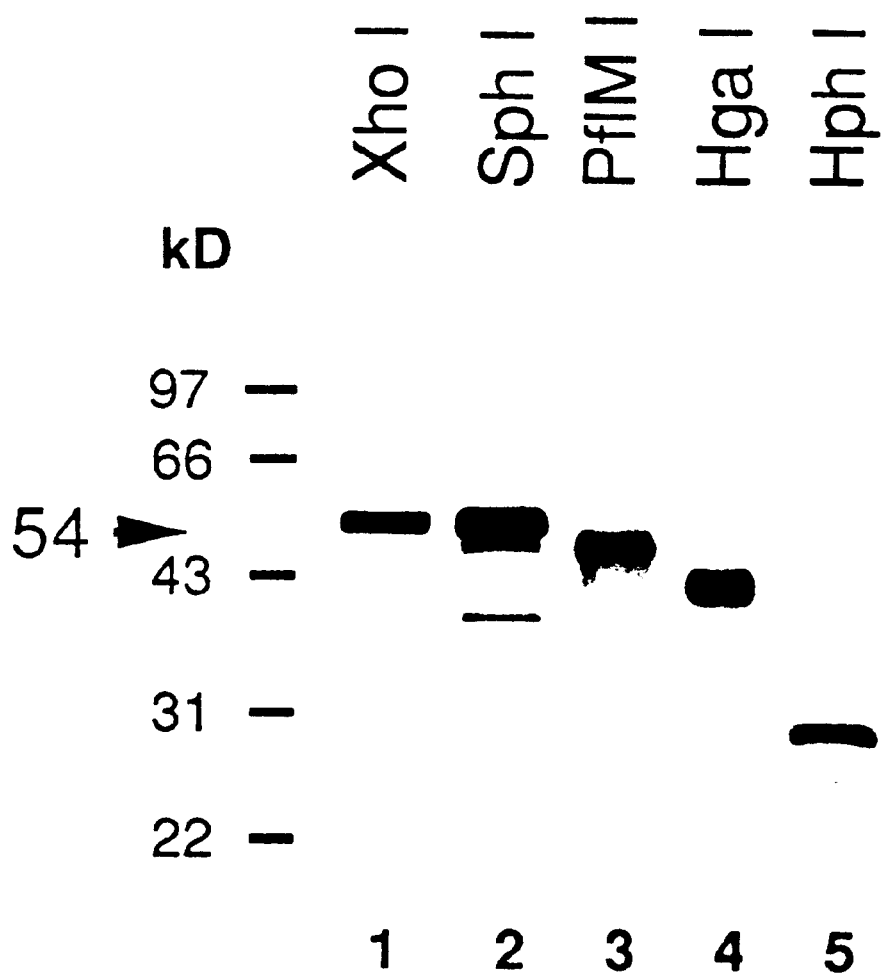
Figure 5D:
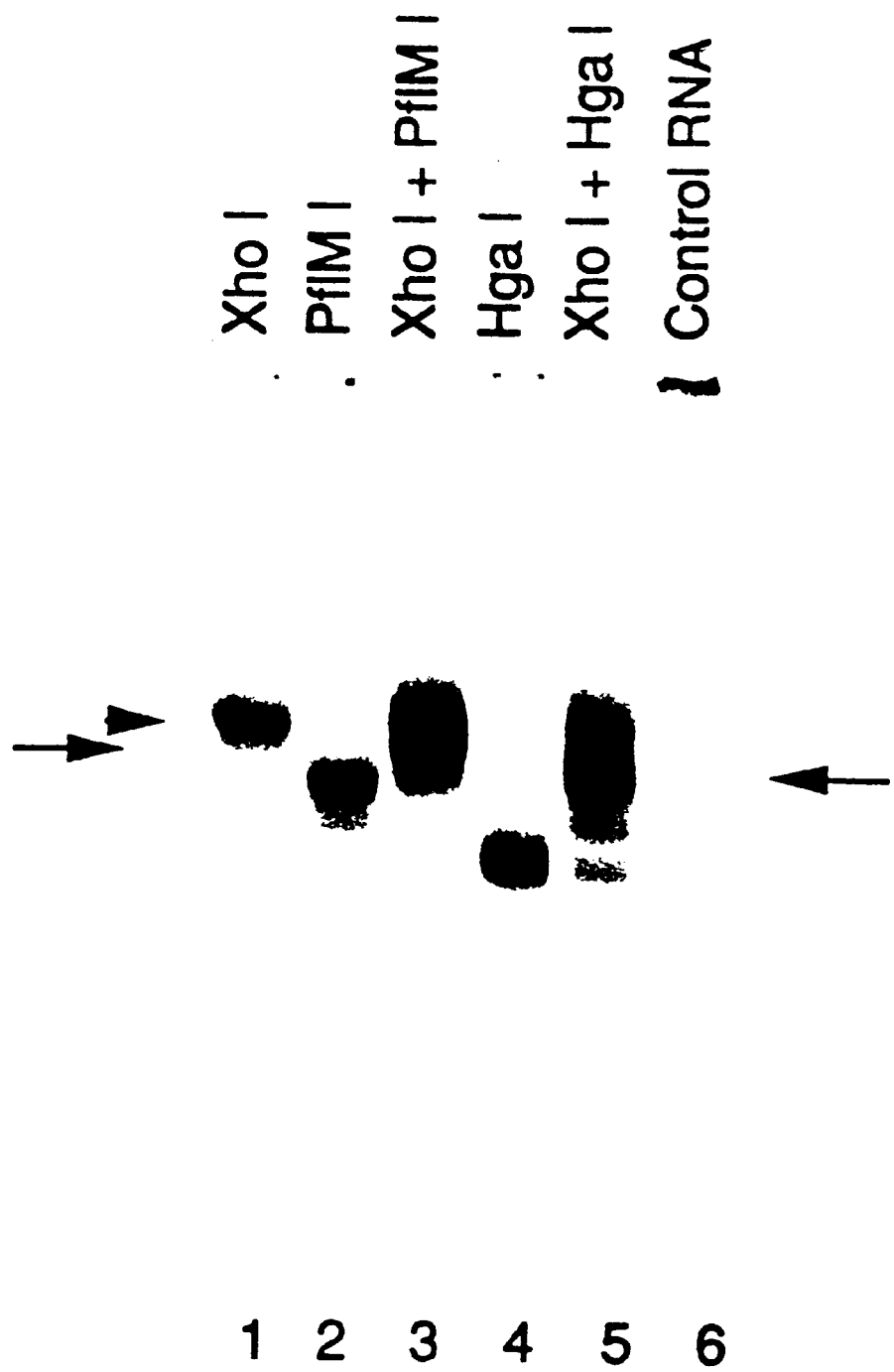

To verify that the cDNA clone pf7 encoded the HNF-4 binding protein, T7 RNA polymerase transcripts were produced and translated in vitro and the resulting protein was tested in the mobility-shift assay. The protein synthesized in vitro bound the APF-1 oligonucleotide in a sequence-specific manner (lanes 3 and 4, FIG. 5B) with the shifted complex migrating at a position identical to that of the complex formed with the material purified from rat liver (compare lane 3 to 1, FIG. 5B). The position of the stop codon was confirmed by cutting the pf7 cDNA at unique restriction sites either before (PflM 1, nucleotide 1309) or after (Sph I, nucleotide 1584) the proposed stop codon (nucleotide 1424) and then synthesizing the protein in vitro and preforming a mobility-shift assay. The product of the template cut with Sph I produced a complex similar to that produced by the full-length cDNA (Xho I), but the PflM I-cut template yielded a faster moving complex (lanes 3, 5, 7; FIG. 5B). Analysis of the protein products on an SDS gel showed that the product from the Sph I-cut template was the same size as that from the full length template (compare lane 2 to 1, FIG. 5C) and that both migrated at a position roughly equivalent to that of the purified rat nuclear protein—54 kD. The product of the PflM I-cut template migrated faster, confirming the prediction that it should be 36 amino acids (4000 daltons) shorter (lane 3, FIG. 5C). Plasmid template cut with Hga I (at nucleotide 1171) produced an even shorter protein product (by 45 amino acids, 5175 daltons) (lane 4, FIG. 5C) which gave rise to a faster migrating shift complex (lane 9, FIG. 5B). When the truncated in vitro translation products were tested for DNA binding to an oligonucleotide containing another HNF-4 site, HNF4P, identical results were obtained (gel not shown). The results of the in vitro translation experiments confirm that the pf7 cDNA encodes a protein that binds to the HNF-4 recognition site in a fashion analogous to that of the purified protein.

HNF-4 Binds to Its Recognition Site as a Dimer

Further examination of translation products produced from truncated cDNA templates showed that a polypeptide containing amino acids 1 to 219 (Hph I-cut, lane 5, FIG. 5C) did not bind DNA even though the entire zinc finger region, the DNA binding domain of the receptors, was present (lane II, FIG. 5B). Thus, the region between amino acid 219 and 374, the possible ligand binding domain, might be required for binding of the HNF-4 protein to its recognition site. Since amino acids in the ligand binding domain of the estrogen receptor are known to be necessary for receptor dimerization and subsequent DNA binding (Kumar & Chambon, 1988; Fawell et al., 1990), we determined whether HNF-4 binds to its recognition site as a monomer or as a dimer. The full length cDNA (Xho I) was co-translated in vitro with either of the two truncated products that bind DNA (PflM I and Hga I) and the products were tested in the mobility-shift assay. When the full length and truncated transcripts were translated together, complexes of intermediate mobility were produced with both the APF-1 probe (lanes 3 and 5, FIG. 5D) and the −151 to −130 TTR probe (not shown). These intermediate bands were most likely produced by heterodimers between the full length and truncated proteins which suggests that the shift complex that was monitored consists of a homodimeric protein bound to the probe. Since no shift complexes corresponding to monomers were detected with either the in vitro translated or the purified protein and since the transcript lacking the proposed domain (Hph I) did not bind the probe at all, we conclude that protein dimerization is required for HNF-4 to bind to its recognition site.

Transcriptional Activation by Cloned HNF-4

Since deletion of the HNF-4 binding site in the TTR promoter severely reduced transcription of transfected templates (Costa et al., 1989), we determined whether HNF-4 produced from the cloned cDNA would activate transcription of a target gene. An expression vector containing HNF-4 cDNA was cotransfected into HeLa cells with constructs containing a reporter gene, chloramphenicol acetyl transferase (CAT), which either did or did not contain HNF-4 recognition sites (APF1-HIV-CAT and HIV-CAT, respectively). The results are shown in FIG. 6. The HNF-4 expression vector containing the cDNA in the sense orientation stimulated CAT production from the reporter constructs only when the HNF-4 sites were present (compare lanes 2–4 to lanes 6–8, FIG. 6). The vector containing the cDNA in the antisense orientation, on the other hand, did not activate CAT expression above background (compare lanes 9–11 to lane 1, FIG. 6). Thus, we concluded that, under the conditions of these experiments, HNF-4 protein can activate transcription of a target gene. Furthermore, since the cells in which the activation occurred were non-hepatic in origin, no liver-specific post-translational modifications seem to be necessary for HNF-4 function.

Tissue Distribution of HNF-4 mRNA is Limited

HNF-4 binding activity was first found in liver. Since then, it has also been found in kidney and intestine but not in spleen or brain (Costa et al., 1990). To see if the tissue distribution of the HNF-4 binding activity reflected that of HNF-4 mRNA and to determine the size of the HNF-4 mRNA, a Northern blot analysis was performed. As shown in FIG. 7, the HNF-4 mRNA is present as a single species in rat liver, kidney and intestine but is absent in spleen, brain, white fat, lung and heart. This result supports the conclusion that HNF-4 is neither present exclusively in liver nor present in all tissues.

The size of the mRNA was the same, ~4.5 kB, in all rat tissues as well as in mouse liver (lane 1, FIG. 7). This is consistent with the fact that the pf7 clone isolated from the rat liver cDNA library contains a cDNA insert approximately 3 kb long but does not contain a polyadenylation site. A weak signal at approximately 2.3 kb was also seen (lanes 2, 3—FIG. 7). It varied in amount between blots; its relation to the major signal, if any, is not known.

HNF-4 Binds to an LF-A1 Site

LF-A1 is a liver-enriched factor that binds to a site required for transcription of human α1-antitrypsin (Monaci et al., 1988; HNF-2 in Li et al., 1988) certain apolipoproteins and other genes expressed in hepatocytes (Hardon et al., 1988; Vaulont et al., 1989). Since the LF-A1 sites are similar in sequence to the HNF-4 binding sites (see Table 1), we used the mobility-shift assay to test the affinity of the HNF-4 protein for one of the LF-A1 sites (FIG. 8). HNF-4 protein, either purified from rat liver or translated in vitro from the HNF-4 cDNA, bound the LF-A1 probe very well, producing a shift complex indistinguishable from those formed with the APF1 and HNF4P probes (compare lane 3 and 9 to 1 and 5 and 7 and 11, respectively—FIG. 8). In fact, the LF-A1 probe gave a stronger signal than the HNF4P probe (all probes were labeled to the same specific activity). To see whether the major protein species that binds the LF-A1 site in crude extracts is the same as that which binds the probe to purify HNF-4 protein, the mobility-shift assay was carried out with crude rat liver nuclear extracts. The results show that the major shift complex that was formed with the LF-A1 probe migrated at a position identical to that formed with the APF1 probe (compare lane 16 to 13, FIG. 8). In addition, the LF-A1 and APF1 complexes were specifically completed by each other (lanes 15 and 18, FIG. 8) and, as with the purified and in vitro produced HNF-4 protein,t he LF-A1 site appeared to have a somewhat lower affinity for the factor than the APF1 site. Thus, it appears that HNF-4 could be identical to LF-A1.

HNF-4 does not Significantly Bind ERE, TRE or GRE

Since the zinc finger region of HNF-4 is very similar to that of the thyroid and thyroid hormone receptors and since the APF1 site contains half of the palindrome found in those response elements (AGGTCA), we tested the HNF-4 protein for binding to estrogen, glucocorticoid and thyroid hormone response elements (ERE, GRE, TRE, respectively, see Table 1) by competition of these sites for labeled APF-1 probe. None of the three hormone response elements significantly blocked complex formation with the APF1 probe (gel not shown). since HNF-4 protein has a very high affinity for the APF1 site, we increased the sensitivity of the assay by using as a probe an oligonucleotide for which HNF-4 has a lower binding affinity, −150 to −130 TTR (see FIG. 1B). The results, shown in FIG. 9, indicate that the GRE and the TRE did not compete the complex formation by the −151 to −130 TTR probe significantly better than a completely unrelated oligonucleotide (015; lanes 11–18). On the other hand, the ERE did compete slightly better than the unrelated oligonucleotide (compare lanes 8 and 19 to 17 and 18) but not nearly as well as the oligonucleotide containing the weakest HNF-4 site known to date (HNF4D) (compare lanes 8–10 to 5–7). Since all these competitions were in high molar excess (50-, 250- and 500-fold), we conclude that HNF-4 does not bind either the GRE, TRE or ERE to a degree which would be likely to be relevant in vivo.

DISCUSSION

The invention in its primary aspect comprises the protein purification of and the cloning and sequencing of a cDNA for a new tissue-restricted mammalian transcription factor termed hepatocyte nuclear factor 4 (HNF-4). HNF-4 was so named because its presence was first detected in liver extracts but not in extracts from several other tissues and its recognition site was distinct from that of three previously described proteins found mainly in the liver (Costa et al., 1989).

HNF-4—a Novel Member of the Steroid Hormone Receptor Superfamily

The deduced amino acid sequence of the HNF-4 protein indicates that it is a member of the steroid/thyroid hormone receptor superfamily, an ever increasing group of ligand-dependent transcription factors which possess a high degree of similarity in their DNA binding (zinc finger) domains. While HNF-4 is similar in sequence to the other factors in the zinc-finger domain, it could be a member of a new subfamily. The members of the superfamily have been classified according to the amino acid sequence in the knuckle of the first zinc finger (between $C_3$ and $C_4$) (referred to as the P Box), a region important in recognizing the sequence of the half site of the palindrome in hormone response elements (Danielson et al., 1989; Mader et al., 1989; Umesono & Evans, 1989; Forman & Samuels, 1990). For example, members of the thyroid hormone receptor (TR) subfamily contain amino acids EGCKG and bind to a TRE while members of the estrogen receptor (ER) subfamily contain amino acids EGCKA and bind to an ERE. The sequence of HNF-4 in this region (DGCKG) is most similar to that of the TR subfamily except that it contains an aspartic acid (D) in place of a glutamic acid (E) following $C_3$. This could explain why HNF-4 does not bind to a TRE (FIG. 9) even though it is almost identical (9/12 residues) to the HNF-4 consensus site. The significance, if any, of the very marginal binding of HNF-4 to the ERE (FIG. 9) is not known. While HNF-4 is the only factor published to date with the DGCKG sequence, considering the sizes of the other subfamilies, we anticipate that more will be found in the future (see receptors compiled in Umesono & Evans, 1989; Forman & Samuels, 1990; hap, de The et al., 1987; H-2 RIIBP, Hamada et al., 1989; N10, Ryseck et al., 1989).

Like the well-characterized receptor proteins (estrogen, Kumar & Chambon, 1988; Fawell et al., 1990; thyroid hormone and retinoic acid, Forman et al., 1989; glucocorticoid Tsai et al., 1988), HNF-4 protein binds to its recognition site as a homodimer (FIG. 5D), even though that site lacks obvious dyad symmetry. Receptor dimerization in the other receptors has been localized to a series of heptad repeats of hydrophobic residues in the ligand-binding domain (Forman et al., 1989; Fawell et al., 1990; Forman & Samuels, 1990). The corresponding region in HNF-4 is also required for DNA binding (FIG. 5B) and contains at least twelve heptad repeats. Homodimer formation raises the possibility of heterodimer formation between HNF-4 and other transcription factors, as has been seen between the thyroid hormone and retionic acid receptors (Forman et al., 1989; Glass et al., 1989).

Since TTR expression is not dependent on hormone regulation, we did not anticipate that HNF-4 would fall into this ligand-dependent superfamily. However, its membership in this family and its limited homology to the ligand binding domains of other receptors with known ligands, raises the possibility that HNF-4 has an as yet unidentified ligand. Considering the number and variety of genes that HNF-4 controls (discussed below), the possibility of a ligand for HNF-4 is of considerable interest. Nonetheless, since so many other members of the superfamily fall into this category of "orphan receptors"—proteins for which no ligand has been identified (e.g., COUP-TF, Wang et al., 1989, ear2, Miyajima et al., 1988; ERR, Giguere et al., 1988; H-2 RIIBP, Hamada et al., 1989; N10, Ryseck et al., 1989), one must also entertain the possibility that these receptors have no ligands. Since the ligand binding domain overlaps with the dimerization domain, similarity in this region could have been maintained only for the purpose of dimerization and not for the purpose of binding a ligand.

HNF-4, LF-A1 and AF-1

LF-A1 is a liver-enriched factor originally identified in the α1-antitrypsin gene promoter (Li et al., 1988; Monaci et al., 1988) as a site conferring positive transcription regulation in vivo and in vitro. LF-A1 sites have been found also in the regulatory regions of the apolipoprotein A1 gene, haptoglobin-related genes (Hardon et al., 1988) and the pyruvate kinase L-type gene (Vaulont et al., 1989). In this paper we present DNA binding data that suggest that HNF-4 could be identical to LF-A1. However, since there are several examples of more than one factor binding to a given enhancer element, particularly among the hormone receptors (reviewed in Wingender, 1990; Ahe et al., 1985; Mueller et al., 1990; Schule et al., 1990; Umesono et al., 1988), positive identification of HNF-4 as LF-A1 must await further purification of LF-A1.

An example of a factor that appears to be distinct from HNF-4 but which has the same binding specificity as HNF-4, is AF-1 (apolipoprotein factor 1) which regulates the human apoCIII and apoB100 genes (Reue et al., 1988; Leff et al., 1989). While AF-1 purified from mouse liver binds to the −151 to −130 TTR oligonucleotide and footprints, the same region of the apoCIII promoter as does the purified HNF-4 protein, the tissue specificity and chromatographic properties of the two factors appears to be disparate (T. Leff, F. M. Sladek, unpublished observations). Regardless of whether HNF-4 is identical to or distinct from LF-A and AF-1, since HNF-4 binds to their recognition sites with relatively high affinity in vitro, one must consider the possibility that HNF-4 might also act on these sites in vivo. HNF-4 could be one of several potentially competing DNA binding proteins that interact with a series of related sites from a variety of genes transcribed in the liver.

HNF-4 and Liver-specific Gene Expression

A primary objective of the present invention is to identify transcription factors that are themselves transcriptionally controlled in the liver. HNF-4 appears to be such a factor: HNF-4 can activate transcription in cells that are not of hepatic origin (FIG. 6) indicating that no liver-specific modifications are required for HNF-4 function, and HNF-4 mRNA is absent in many tissues (FIG. 7). These results, taken together with the demonstration that the rate of HNF-4 gene transcription is high in the liver but negligible in other tissues (Xanthopoulos, Prezioso, Chen, Sladek, Darnell, in preparation), indicate that HNF-4, like HNF-3 (Lai et al., 1990) and C/EBP (Xanthopoulos et al., 1989), is a transcriptionally controlled transcription factor. Antecedent regulatory genes in a regulatory cascade can now be sought with confidence by studying the factors that regulate the genes that encode these regulatory proteins.

The investigation of tissue specific expression has ruled out, to a greater or lesser degree, two simple hypotheses which were entertained. First, there is no universal liver-specific transcription factor or group of transcription factors: HNF-1, C/EBP, HNF-3 and HNF-4 all have binding sites on several genes but none is a "master" positive-acting factor. Indeed, all of these factors are present in tissues other than liver and some are even in tissues not of the same germline as the liver (HNF-1, also in kidney and spleen, Baumeueter et al., 1990; C/EB, brain, fat, intestine, lung and skin, Birkenmeier et al., 1989; Xanthopoulos et al., 1989; Kuo et al., 1990; Ruppert et al., 1990; HNF-3A, intestine in small amounts; HNF-4, kidney and intestine, FIG. 7). In addition to varying in their tissue distribution, these factors have protein structures that classify them as members of four distinct groups of regulators, none of which is found exclusively in the liver (HNF-1, homeo domain; C/EBP, leucine zipper; HNF-3, unclassified; HNF-4, steroid hormone receptors). Second, we cannot immediately understand the logic that unites the group of genes that a particular factor may help regulate. For example, HNF-4 apparently acts positively on genes encoding apolipoproteins, which are involved in cholesterol homeostasis, transthyretin, which carries thyroid hormone and Vitamin A in the serum, as well as α1-antitrypsin, a protease inhibitor, pyruvate kinase, which plays a role in glycolysis, and glutamine synthetase, which acts in amino acid biosynthesis (C. F. Kuo, F. M. Sladek, unpublished observations). Why this factor is involved in regulating this varied assortment of genes is far from obvious.

The invention has been described in detail, setting forth the preferred embodiments. However, alternative embodiments are contemplated as falling within the invention. consequently, the scope of the claims is not to be limited by the teachings contained herein.

What is claimed is:

1. A competitive assay for binding activity to recombinant HNF-4 receptors, comprising:

(a) reacting a suspected ligand with a recombinant HNF-4 receptor in the presence of a known quantity of a labeled competing ligand; and (b) comparing the amount of bound label in the presence of the suspected ligand to that observed in its absence, wherein the HNF-4 receptor is a chimeric receptor comprising the ligand binding domain of a HNF-4 receptor and a DNA binding domain of another receptor which has a known ligand.

2. The assay of claim 1, wherein the DNA binding domain is from a glucocorticoid receptor.

3. The assay of claim 1, wherein the DNA binding domain is from an estrogen receptor.

4. The assay of claim 1, wherein the DNA binding domain is from a retinoic acid receptor.

5. The assay of claim 1, wherein the HNF-4 receptor is a chimeric receptor comprising a fragment of the ligand binding domain of the HNF-4 receptor, and the DNA binding domain of another receptor which has a known ligand, and wherein the fragment of the ligand binding domain retains ligand binding activity.

* * * * *